(12) United States Patent
Cheung et al.

(10) Patent No.: US 9,879,031 B2
(45) Date of Patent: Jan. 30, 2018

(54) COMPOUNDS AS DIACYLGLYCEROL ACYLTRANSFERASE INHIBITORS

(71) Applicant: GlaxoSmithKline LLC, Wilmington, New Castle, DE (US)

(72) Inventors: Mui Cheung, King of Prussia, PA (US); Raghuram S. Tangirala, Secunderabad (IN)

(73) Assignee: GLAXOSMITHKLINE LLC, Wilmington, New Castle, DE (US)

( * ) Notice: Subject to any disclaimer, the term of this patent is extended or adjusted under 35 U.S.C. 154(b) by 0 days.

(21) Appl. No.: 15/646,279

(22) Filed: Jul. 11, 2017

(65) Prior Publication Data

US 2017/0305928 A1    Oct. 26, 2017

Related U.S. Application Data

(63) Continuation of application No. 15/370,051, filed on Dec. 6, 2016, now Pat. No. 9,738,658, which is a continuation of application No. 14/087,122, filed on Nov. 22, 2013.

(30) Foreign Application Priority Data

Nov. 23, 2012  (IN) .......................... 3593/DEL/2012
Mar. 14, 2013  (IN) ............................ 750/DEL/2013

(51) Int. Cl.
*C07D 209/40* (2006.01)
*C07D 498/04* (2006.01)
*C07D 519/00* (2006.01)

(52) U.S. Cl.
CPC ......... *C07D 498/04* (2013.01); *C07D 519/00* (2013.01)

(58) Field of Classification Search
CPC ... C07D 209/40; C07D 498/04; C07D 519/00
See application file for complete search history.

(56) References Cited

U.S. PATENT DOCUMENTS

| 8,859,536 | B2 | 10/2014 | Qin et al. |
| 9,040,517 | B2 | 5/2015 | Cheung et al. |
| 9,273,069 | B2 | 3/2016 | Cheung et al. |
| 9,540,400 | B2 | 1/2017 | Qin et al. |
| 2009/0036425 | A1 | 2/2009 | Dow et al. |
| 2009/0076275 | A1 | 3/2009 | Bolin et al. |
| 2010/0075962 | A1 | 3/2010 | Lee et al. |
| 2010/0113782 | A1 | 5/2010 | Bolin et al. |
| 2010/0204119 | A1 | 8/2010 | Aspnes et al. |
| 2011/0251173 | A1 | 10/2011 | Birch et al. |

FOREIGN PATENT DOCUMENTS

| IN | 1452/DEL/2011 | 11/2012 |
| WO | WO 2009/040410 A1 | 4/2009 |
| WO | WO 2012/162129 A1 | 11/2012 |

OTHER PUBLICATIONS

Dow, et al. ACS Medicinal Chemistry Letters, 2: 407-412 (2011).

*Primary Examiner* — Bruck Kifle
(74) *Attorney, Agent, or Firm* — Duke M. Fitch; Kathryn A. Lutomski; Edward R. Gimmi

(57) ABSTRACT

This invention relates to important intermediates in the preparation of a compound which is an inhibitor of acyl coenzyme A: diacylglycerol acyltransferase 1 (DGAT-1).

3 Claims, No Drawings

COMPOUNDS AS DIACYLGLYCEROL ACYLTRANSFERASE INHIBITORS

FIELD OF INVENTION

This invention relates to novel compounds which are inhibitors of acyl coenzyme A: diacylglycerol acyltransferase 1 (DGAT-1), to pharmaceutical compositions containing them, to processes for their preparation, and to their use in therapy, alone or in combination with weight management therapies or other triglyceride lowering therapy, for the prevention or treatment of diseases related to DGAT-1 dysfunction or where modulation of DGAT-1 activity may have therapeutic benefit including but not limited to obesity, obesity related disorders, genetic (Type 1, Type 5 hyperlipidemia) and acquired forms of hypertriglyceridemia or hyperlipoproteinemia-related disorders, caused by but not limited to lipodystrophy, hypothyroidism, medications (beta blockers, thiazides, estrogen, glucocorticoids, transplant) and other factors (pregnancy, alcohol intake), hyperlipoproteinemia, chylomicronemia, dyslipidemia, non-alcoholic steatohepatitis, diabetes, insulin resistance, metabolic syndrome, cardiovascular outcomes, angina, excess hair growth (including syndromes associated with hirsutism), nephrotic syndrome, fibrosis such as myocardial, renal and liver fibrosis, hepatitis C virus infection and acne or other skin disorders.

BACKGROUND OF THE INVENTION

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, hypertension, and arteriosclerosis. It is also known that increased body weight due to obesity can place a burden on joints, such as knee joints, causing arthritis, pain, and stiffness.

Because overeating and obesity have become such a problem in the general population, many individuals are now interested in losing weight, reducing weight, and maintaining a healthy body weight and desirable lifestyle. One approach to treating obesity is to reduce food intake and/or hyperlipidemia. It has been suggested that molecules which are developed to prevent the accumulation of triglyceride would not only reduce obesity but also have the additional beneficial effect of reducing insulin resistance, a primary factor contributing to the development of diabetes.

Acyl coenzyme A: diacylglycerol acyltransferase 1 (DGAT-1) is one of two known DGAT enzymes that catalyze the final step in mammalian triglyceride synthesis. DGAT-1 is an enzyme that is implicated in the development of both diabetes and insulin resistance. Studies of DGAT-1 deficient mice show that DGAT-1 deficiency protects against insulin resistance and obesity, see Chen, H. C. et al., *J Clin Invest.*, 109(8), 1049-1055 (2002). Therefore, inhibitors of DGAT-1 should be useful for the treatment of metabolic disorders, e.g. obesity, Type 2 diabetes, and insulin resistance syndrome (or metabolic syndrome) and other associated or related diseases and conditions.

SUMMARY OF THE INVENTION

This invention relates to compounds of Formula (I) or pharmaceutically acceptable salts thereof:

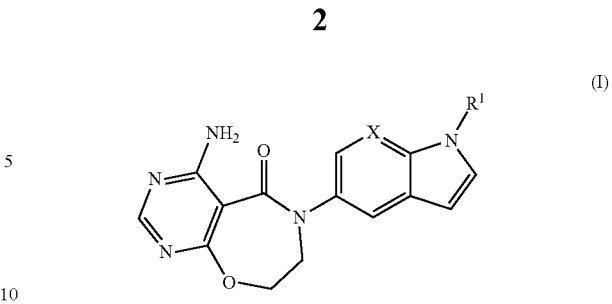

wherein:

X is CH, $CR^2$, or N;

$R^1$ is $(C_1$-$C_4)$alkyl, $(C_3$-$C_7)$cycloalkyl, 4- to 6-membered heterocycloalkyl, phenyl, or 5- or 6-membered heteroaryl, wherein said $(C_1$-$C_4)$alkyl is optionally substituted by hydroxyl, $(C_1$-$C_4)$alkoxy, —$CO_2H$, or —$CO_2(C_1$-$C_4)$alkyl, and wherein said phenyl or 5- or 6-membered heteroaryl is optionally substituted by —$O(C_1$-$C_2)$alkylO— or optionally substituted with one to three substituents independently selected from halogen, cyano, oxo, hydroxyl, $(C_1$-$C_4)$alkoxy, halo$(C_1$-$C_4)$alkoxy, $(C_3$-$C_7)$cycloalkoxy, phenyl$(C_1$-$C_2)$alkoxy, $(C_1$-$C_4)$alkyl, halo$(C_1$-$C_4)$alkyl, hydroxy$(C_1$-$C_4)$alkyl, —$CO_2H$, and —$CO_2(C_1$-$C_4)$alkyl; and $R^2$ is halogen, $(C_1$-$C_4)$alkyl, halo$(C_1$-$C_4)$alkyl, $(C_3$-$C_7)$cycloalkyl, 4- to 6-membered heterocycloalkyl, —NHC(O)$(C_1$-$C_4)$alkyl, or —NHC(O)$(C_3$-$C_7)$cycloalkyl;

provided that the compound is not 4-amino-6-(1-propyl-1H-indol-5-yl)-7,8-dihydropyrimido[5,4-f][1,4]oxazepin-5(6H)-one, 4-amino-6-(1-cyclopropyl-1H-pyrrolo[2,3-b]pyridin-5-yl)-7,8-dihydropyrimido[5,4-f][1,4]oxazepin-5(6H)-one, 3-(5-(4-amino-5-oxo-7,8-dihydropyrimido[5,4-f][1,4]oxazepin-6(5H)-yl)-1H-indol-1-yl)propanoic acid, 4-amino-6-(1-(3-methoxypropyl)-1H-indol-5-yl)-7,8-dihydropyrimido[5,4-f][1,4]oxazepin-5(6H)-one, 4-amino-6-(1-methyl-1H-indol-5-yl)-7,8-dihydropyrimido[5,4-f][1,4]oxazepin-5(6H)-one, 4-amino-6-(1-(2-methoxyethyl)-1H-indol-5-yl)-7,8-dihydropyrimido[5,4-f][1,4]oxazepin-5(6H)-one, 4-amino-6-(1-isopropyl-1H-indol-5-yl)-7,8-dihydropyrimido[5,4-f][1,4]oxazepin-5(6H)-one, 4-amino-6-(1-propyl-1H-pyrrolo[2,3-b]pyridin-5-yl)-7,8-dihydropyrimido[5,4-f][1,4]oxazepin-5(6H)-one, 4-amino-6-(1-(2-methoxyethyl)-1H-pyrrolo[2,3-b]pyridin-5-yl)-7,8-dihydropyrimido[5,4-f][1,4]oxazepin-5(6H)-one, 4-amino-6-(1-cyclohexyl-1H-pyrrolo[2,3-b]pyridin-5-yl)-7,8-dihydropyrimido[5,4-f][1,4]oxazepin-5(6H)-one, 4-amino-6-(1-isopropyl-1H-pyrrolo[2,3-b]pyridin-5-yl)-7,8-dihydropyrimido[5,4-f][1,4]oxazepin-5(6H)-one, 4-amino-6-(1-(2-hydroxyethyl)-1H-pyrrolo[2,3-b]pyridin-5-yl)-7,8-dihydropyrimido[5,4-f][1,4]oxazepin-5(6H)-one, 4-amino-6-(1-cyclopropyl-1H-indol-5-yl)-7,8-dihydropyrimido[5,4-f][1,4]oxazepin-5(6H)-one, 4-amino-6-(1-phenyl-1H-indol-5-yl)-7,8-dihydropyrimido[5,4-f][1,4]oxazepin-5(6H)-one, 4-amino-6-(1-(4-(trifluoromethyl)phenyl)-1H-pyrrolo[2,3-b]pyridin-5-yl)-7,8-dihydropyrimido[5,4-f][1,4]oxazepin-5(6H)-one, 4-amino-6-(1-(4-fluorophenyl)-1H-pyrrolo[2,3-b]pyridin-5-yl)-7,8-dihydropyrimido[5,4-f][1,4]oxazepin-5(6H)-one, 4-amino-6-(1-(3-chlorophenyl)-1H-pyrrolo[2,3-b]pyridin-5-yl)-7,8-dihydropyrimido[5,4-f][1,4]oxazepin-5(6H)-one, 4-amino-6-(1-(3-chlorophenyl)-1H-indol-5-yl)-7,8-dihydropyrimido[5,4-f][1,4]oxazepin-5(6H)-one, 6-amino-4-(7-(2-methoxyphenyl)-7H-pyrrolo[2,3-b]pyridin-3-yl)-3,4-dihydropyrimido[5,4-f][1,4]oxazepin-5(2H)-one, 4-amino-6-(1-(2-methoxyphenyl)-1H-indol-5-yl)-7,8-dihydropyrimido[5,4-f][1,4]oxazepin-5(6H)-one, 4-amino-6-(1-phenyl-1H-pyrrolo[2,3-b]pyridin-5-yl)-7,8-dihydropyrimido[5,4-f][1,4]oxazepin-5(6H)-one, 4-amino- 6-(1-(2-fluorophenyl)-1H-pyrrolo[2,3-b]pyridin-5-yl)-7,8-dihydropyrimido[5,4-f][1,4]oxazepin-5(6H)-one, 4-amino-6-(1-(3,4-difluorophenyl)-1H-indol-5-yl)-7,8-dihydropyrimido[5,4-f][1,4]oxazepin-5(6H)-one, 4-amino-6-(1-(3,4-difluorophenyl)-1H-pyrrolo[2,3-b]pyridin-5-yl)-7,8-dihydropyrimido[5,4-f][1,4]oxazepin-5(6H)-one, 4-amino-6-(1-(2-fluorophenyl)-1H-indol-5-yl)-7,8-dihydropyrimido[5,4-f][1,4]oxazepin-5(6H)-one, 4-amino-6-(1-(4-(trifluoromethyl)phenyl)-1H-indol-5-yl)-7,8-dihydropyrimido[5,4-f][1,4]oxazepin-5(6H)-one, 4-amino-6-(1-(4-chlorophenyl)-1H-pyrrolo[2,3-b]pyridin-5-yl)-7,8-dihydropyrimido[5,4-f][1,4]oxazepin-5(6H)-one, 4-amino-6-(1-(3-(trifluoromethyl)phenyl)-1H-indol-5-yl)-7,8-dihydropyrimido[5,4-f][1,4]oxazepin-5(6H)-one, 4-amino-6-(1-(3-(trifluoromethyl)phenyl)-1H-pyrrolo[2,3-b]pyridin-5-yl)-7,8-dihydropyrimido[5,4-f][1,4]oxazepin-5(6H)-one, 4-amino-6-(1-(thiazol-2-yl)-1H-indol-5-yl)-7,8-dihydropyrimido[5,4-f][1,4]oxazepin-5(6H)-one, 4-amino-6-(1-(6-(trifluoromethyl)pyridin-3-yl)-1H-indol-5-yl)-7,8-dihydropyrimido[5,4-f][1,4]oxazepin-5(6H)-one, 4-amino-6-(1-(pyridin-2-yl)-1H-indol-5-yl)-7,8-dihydropyrimido[5,4-f][1,4]oxazepin-5(6H)-one, 4-amino-6-(1-(pyridin-2-yl)-1H-pyrrolo[2,3-b]pyridin-5-yl)-7,8-dihydropyrimido[5,4-f][1,4]oxazepin-5(6H)-one, 4-amino-6-(1-(pyrazin-2-yl)-1H-pyrrolo[2,3-b]pyridin-5-yl)-7,8-dihydropyrimido[5,4-f][1,4]oxazepin-5(6H)-one, 4-amino-6-(1-(pyrazin-2-yl)-1H-indol-5-yl)-7,8-dihydropyrimido[5,4-f][1,4]oxazepin-5(6H)-one, 4-amino-6-(1-(5-(trifluoromethyl)pyridin-2-yl)-1H-indol-5-yl)-7,8-dihydropyrimido[5,4-f][1,4]oxazepin-5(6H)-one, 4-amino-6-(1-(5-(trifluoromethyl)pyridin-2-yl)-1H-pyrrolo[2,3-b]pyridin-5-yl)-7,8-dihydropyrimido[5,4-f][1,4]oxazepin-5(6H)-one, 4-amino-6-(1-(thiazol-2-yl)-1H-pyrrolo[2,3-b]pyridin-5-yl)-7,8-dihydropyrimido[5,4-f][1,4]oxazepin-5(6H)-one, 4-amino-6-(1-(6-(trifluoromethyl)pyridin-3-yl)-1H-pyrrolo[2,3-b]pyridin-5-yl)-7,8-dihydropyrimido[5,4-f][1,4]oxazepin-5(6H)-one, 4-amino-6-(1-(6-methylpyridin-3-yl)-1H-indol-5-yl)-7,8-dihydropyrimido[5,4-f][1,4]oxazepin-5(6H)-one, 4-amino-6-(1-(4-(difluoromethyl)phenyl)-1H-indol-5-yl)-7,8-dihydropyrimido[5,4-f][1,4]oxazepin-5(6H)-one, 4-amino-6-(1-(4-(difluoromethyl)phenyl)-1H-pyrrolo[2,3-b]pyridin-5-yl)-7,8-dihydropyrimido[5,4-f][1,4]oxazepin-5(6H)-one, or 4-amino-6-(1-(4-(trifluoromethyl)pyridin-2-yl)-1H-pyrrolo[2,3-b]pyridin-5-yl)-7,8-dihydropyrimido[5,4-f][1,4]oxazepin-5(6H)-one.

This invention also relates to a pharmaceutical composition comprising a compound of Formula (I) and a pharmaceutically acceptable excipient.

This invention also relates to a method of treating obesity comprising administering to a human in need thereof an effective amount of a compound of Formula (I) or a pharmaceutically acceptable salt thereof.

DETAIL DESCRIPTION OF THE INVENTION

This invention relates to compounds of the Formula (I) as defined above.

In another embodiment, this invention relates to compounds of Formula (I) wherein X is CH or $CR^2$. In a specific embodiment, this invention relates to compounds of Formula (I) wherein X is CH. In another specific embodiment, this invention relates to compounds of Formula (I) wherein X is N.

In another embodiment, this invention relates to compounds of Formula (I) wherein $R^2$ is $(C_3-C_7)$cycloalkyl, 4- to 6-membered heterocycloalkyl, or —NHC(O)$(C_3-C_7)$cycloalkyl. In a specific embodiment, this invention relates to compounds of Formula (I) wherein $R^2$ is cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, —NHC(O)cyclopropyl, —NHC(O)cyclobutyl, —NHC(O)cyclopentyl, or —NHC(O)cyclohexyl. In a more specific embodiment, this invention relates to compounds of Formula (I) wherein $R^2$ is cyclopropyl, morpholinyl, or —NHC(O)cyclopropyl.

In another specific embodiment, this invention relates to compounds of Formula (I) wherein $R^2$ is cyclopropyl, cyclobutyl, cyclopentyl, cyclohexyl. In a more specific embodiment, this invention relates to compounds of Formula (I) wherein $R^2$ is cyclopropyl.

In another specific embodiment, this invention relates to compounds of Formula (I) wherein $R^2$ is azetidinyl, oxetanyl, pyrrolidinyl, piperidinyl, piperazinyl, morpholinyl, thiomorpholinyl, or tetrahydropyranyl. In a more specific embodiment, this invention relates to compounds of Formula (I) wherein $R^2$ is morpholinyl.

In another specific embodiment, this invention relates to compounds of Formula (I) wherein $R^2$ is —NHC(O)cyclopropyl, —NHC(O)cyclobutyl, —NHC(O)cyclopentyl, or —NHC(O)cyclohexyl. In a more specific embodiment, this invention relates to compounds of Formula (I) wherein $R^2$ is —NHC(O)cyclopropyl.

In another embodiment, this invention relates to compounds of Formula (I) wherein $R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, bromine, methyl, ethyl, trifluoromethyl, oxo, hydroxyl, methoxy, ethoxy, isopropyloxy, isobutyloxy, difluoromethoxy, trifluoromethoxy, and cyclopentyloxy. In another embodiment, this invention relates to compounds of Formula (I) wherein $R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, methyl, trifluoromethyl, oxo, hydroxyl, methoxy, ethoxy, isopropyloxy, isobutyloxy, difluoromethoxy, trifluoromethoxy, and cyclopentyloxy. In a specific embodiment, this invention relates to compounds of Formula (I) wherein $R^1$ is n-propyl, isopropyl, 2-hydroxy-2-methyl-prop-1-yl, cyclobutyl, oxetanyl, tetrahydropyranyl, 2-ethylphenyl, 2,3-dichlorophenyl, 3,5-dichlorophenyl, 2-hydroxyphenyl, 2-methoxyphenyl, 2-ethoxyphenyl, 2-isopropyloxyphenyl, 3-isobutyloxyphenyl, 3-difluoromethoxyphenyl, 2-trifluoromethoxyphenyl, 3-trifluoromethoxyphenyl, 2-methoxy-4-methylphenyl, 2-methoxy-4-trifluoromethylphenyl, 3-chloro-2-methoxyphenyl, 2-bromo-3-methoxyphenyl, 2-cyclopentyloxyphenyl, 5-methyl-1,3,4-oxadiazol-2-yl, 5-methyl-1,3,4-triazol-2-yl, 6-methylpyridin-3-yl, 2-methoxy-6-methylpyridin-3-yl, 1-methyl-6-oxo-1,6-dihydropyridin-3-yl, 2-methylpyrimidin-5-yl, 2-ethylpyrimidin-5-yl, 2-methoxypyrimidin-5-yl, or 5-methylpyrazin-2-yl. In another specific embodiment, this invention relates to compounds of Formula (I) wherein $R^1$ is n-propyl, isopropyl, 2-hydroxy-2-methyl-prop-1-yl, cyclobutyl, oxetanyl, 2,3-dichlorophenyl, 3,5-dichlorophenyl, 2-hydroxyphenyl, 2-methoxyphenyl, 2-ethoxyphenyl, 2-isopropyloxyphenyl, 3-isobutyloxyphenyl, 3-difluoromethoxyphenyl, 2-trifluoromethoxyphenyl, 3-trifluoromethoxyphenyl, 2-methoxy-4-trifluoromethylphenyl, 2-cyclopentyloxyphenyl, 5-methyl-1,3,4-oxadiazol-2-yl, 6-methylpyridin-3-yl, 1-methyl-6-oxo-1,6-dihydropyridin-3-yl, or 2-methylpyrimidin-5-yl.

In another embodiment, this invention relates to compounds of Formula (I) wherein $R^1$ is $(C_1-C_4)$alkyl which is optionally substituted by hydroxyl, $(C_1-C_4)$alkoxy, —$CO_2H$, or —$CO_2(C_1-C_4)$alkyl. In another embodiment, this invention relates to compounds of Formula (I) wherein $R^1$ is $(C_1-C_4)$alkyl or hydroxy$(C_1-C_4)$alkyl. In a specific embodiment, this invention relates to compounds of Formula (I) wherein $R^1$ is n-propyl, isopropyl, or 2-hydroxy-2-methyl-prop-1-yl.

In another embodiment, this invention relates to compounds of Formula (I) wherein $R^1$ is $(C_3-C_7)$cycloalkyl or 4- to 6-membered heterocycloalkyl. In a specific embodiment, this invention relates to compounds of Formula (I) wherein $R^1$ is cyclopropyl, cyclobutyl, cyclopentyl, cyclohexyl, azetidinyl, oxetanyl, pyrrolidinyl, piperidinyl, piperazinyl, morpholinyl, thiomorpholinyl, or tetrahydropyranyl. In another specific embodiment, this invention relates to compounds of Formula (I) wherein $R^1$ is cyclobutyl, oxetanyl, or tetrahydropyranyl. In a more specific embodiment, this invention relates to compounds of Formula (I) wherein $R^1$ is cyclobutyl or oxetanyl.

In another embodiment, this invention relates to compounds of Formula (I) wherein $R^1$ is phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, each of which is optionally substituted by —$O(C_1-C_2)$alkylO— or optionally substituted with one to three substituents independently selected from halogen, cyano, oxo, hydroxyl, $(C_1-C_4)$alkoxy, halo$(C_1-C_4)$alkoxy, $(C_3-C_7)$cycloalkoxy, phenyl$(C_1-C_2)$alkoxy, $(C_1-C_4)$alkyl, halo$(C_1-C_4)$alkyl, hydroxy$(C_1-C_4)$alkyl, —$CO_2H$, and —$CO_2(C_1-C_4)$alkyl. In another embodiment, this invention relates to compounds of Formula (I) wherein $R^1$ is phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, each of which is optionally substituted with one or two substituents independently selected from chlorine, bromine, methyl, ethyl, trifluoromethyl, oxo, hydroxyl, methoxy, ethoxy, isopropyloxy, isobutyloxy, difluoromethoxy, trifluoromethoxy, and cyclopentyloxy. In another embodiment, this invention relates to compounds of Formula (I) wherein $R^1$ is phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, each of which is optionally substituted with one or two substituents independently selected from chlorine, methyl, trifluoromethyl, oxo, hydroxyl, methoxy, ethoxy, isopropyloxy, isobutyloxy, difluoromethoxy, trifluoromethoxy, and cyclopentyloxy.

In another embodiment, this invention relates to compounds of Formula (I) wherein $R^1$ is phenyl which is optionally substituted by —$O(C_1-C_2)$alkylO— or optionally substituted with one to three substituents independently selected from halogen, cyano, oxo, hydroxyl, $(C_1-C_4)$alkoxy, halo$(C_1-C_4)$alkoxy, $(C_3-C_7)$cycloalkoxy, phenyl$(C_1-C_2)$alkoxy, $(C_1-C_4)$alkyl, halo$(C_1-C_4)$alkyl, hydroxy$(C_1-C_4)$alkyl, —$CO_2H$, and —$CO_2(C_1-C_4)$alkyl. In another embodiment, this invention relates to compounds of Formula (I) wherein $R^1$ is phenyl which is optionally substituted by —$O(C_1-C_2)$alkylO— or optionally substituted with one or two substituents independently selected from fluorine, chlorine, hydroxyl, $(C_1-C_4)$alkoxy, halo$(C_1-C_4)$alkoxy, $(C_3-C_7)$cycloalkoxy, $(C_1-C_4)$alkyl, and halo$(C_1-C_4)$alkyl. In another embodiment, this invention relates to compounds of Formula (I) wherein $R^1$ is phenyl which is optionally substituted with one or two substituents independently selected from chlorine, bromine, methyl, ethyl, trifluoromethyl, hydroxyl, methoxy, ethoxy, isopropyloxy, isobutyloxy, difluoromethoxy, trifluoromethoxy, and cyclopentyloxy. In another embodiment, this invention relates to compounds of Formula (I) wherein $R^1$ is phenyl which is optionally substituted with one or two substituents independently selected from chlorine, methyl, trifluoromethyl, hydroxyl, methoxy, ethoxy, isopropyloxy, isobutyloxy, difluoromethoxy, trifluoromethoxy, and cyclopentyloxy. In a specific embodiment, this invention relates to compounds of Formula (I) wherein $R^1$ is 2-ethylphenyl, 2,3-dichlorophenyl, 3,5-dichlorophenyl, 2-hydroxyphenyl, 2-methoxyphenyl, 2-ethoxyphenyl, 2-isopropyloxyphenyl, 3-isobutyloxyphenyl, 3-difluoromethoxyphenyl, 2-trifluoromethoxyphenyl, 3-trifluoromethoxyphenyl, 2-methoxy-4-methylphenyl, 2-methoxy-4-trifluoromethylphenyl, 3-chloro-2-methoxyphenyl, 2-bromo-3-methoxyphenyl, or 2-cyclopentyloxyphenyl. In another specific embodiment, this invention relates to compounds of Formula (I) wherein $R^1$ is 2,3-dichlorophenyl, 3,5-dichlorophenyl, 2-hydroxyphenyl, 2-methoxyphenyl, 2-ethoxyphenyl, 2-isopropyloxyphenyl, 3-isobutyloxyphenyl, 3-difluoromethoxyphenyl, 2-trifluoromethoxyphenyl, 3-trifluoromethoxyphenyl, 2-methoxy-4-trifluoromethylphenyl, or 2-cyclopentyloxyphenyl.

In another embodiment, this invention relates to compounds of Formula (I) wherein $R^1$ is furanyl, thienyl, pyrrolyl, imidazolyl, pyrazolyl, triazolyl, tetrazolyl, thiazolyl, oxazolyl, isoxazolyl, oxadiazolyl, thiadiazolyl, or isothiazolyl, each of which is optionally substituted with one or two substituents independently selected from hydroxyl, $(C_1-C_4)$alkoxy, halo$(C_1-C_4)$alkoxy, $(C_3-C_7)$cycloalkoxy, $(C_1-C_4)$alkyl, and halo$(C_1-C_4)$alkyl. In another embodiment, this invention relates to compounds of Formula (I) wherein $R^1$ is furanyl, thienyl, pyrrolyl, imidazolyl, pyrazolyl, triazolyl, tetrazolyl, thiazolyl, oxazolyl, isoxazolyl, oxadiazolyl, thiadiazolyl, or isothiazolyl, each of which is optionally substituted with one or two substituents independently selected from methyl, trifluoromethyl, hydroxyl, methoxy, ethoxy, isopropyloxy, isobutyloxy, difluoromethoxy, trifluoromethoxy, and cyclopentyloxy. In a specific embodiment, this invention relates to compounds of Formula (I) wherein $R^1$ is 5-methyl-1,3,4-oxadiazol-2-yl or 5-methyl-1,3,4-triazol-2-yl. In another specific embodiment, this invention relates to compounds of Formula (I) wherein $R^1$ is 5-methyl-1,3,4-oxadiazol-2-yl.

In another embodiment, this invention relates to compounds of Formula (I) wherein $R^1$ is pyridinyl, pyridazinyl, pyrazinyl, or pyrimidinyl, each of which is optionally substituted with one or two substituents independently selected from oxo, hydroxyl, $(C_1-C_4)$alkoxy, halo$(C_1-C_4)$alkoxy, $(C_3-C_7)$cycloalkoxy, $(C_1-C_4)$alkyl, and halo$(C_1-C_4)$alkyl. In another embodiment, this invention relates to compounds of Formula (I) wherein $R^1$ is pyridinyl, pyridazinyl, pyrazinyl, or pyrimidinyl, each of which is optionally substituted with one or two substituents independently selected from methyl, trifluoromethyl, hydroxyl, oxo, methoxy, ethoxy, isopropyloxy, isobutyloxy, difluoromethoxy, trifluoromethoxy, and cyclopentyloxy. In a specific embodiment, this invention relates to compounds of Formula (I) wherein $R^1$ is 6-methylpyridin-3-yl, 2-methoxy-6-methylpyridin-3-yl, 1-methyl-6-oxo-1,6-dihydropyridin-3-yl, 2-methylpyrimidin-5-yl, 2-ethylpyrimidin-5-yl, 2-methoxypyrimidin-5-yl, or 5-methylpyrazin-2-yl. In another specific embodiment, this invention relates to compounds of Formula (I) wherein $R^1$ is 6-methylpyridin-3-yl, 1-methyl-6-oxo-1,6-dihydropyridin-3-yl, or 2-methylpyrimidin-5-yl.

In a particular embodiment, this invention relates to compounds of Formula (I) or pharmaceutically acceptable salts thereof wherein:

X is CH or $CR^2$;

$R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, bromine, methyl, ethyl, trifluoromethyl, oxo, hydroxyl, methoxy, ethoxy, isopropyloxy, isobutyloxy, difluoromethoxy, trifluoromethoxy, and cyclopentyloxy; and $R^2$ is cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, —NHC(O)cyclopropyl, —NHC(O)cyclobutyl, —NHC(O)cyclopentyl, or —NHC(O)cyclohexyl.

In a particular embodiment, this invention relates to compounds of Formula (I) or pharmaceutically acceptable salts thereof wherein:

X is CH or $CR^2$;

$R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, methyl, trifluoromethyl, oxo, hydroxyl, methoxy, ethoxy, isopropyloxy, isobutyloxy, difluoromethoxy, trifluoromethoxy, and cyclopentyloxy; and $R^2$ is cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, —NHC(O)cyclopropyl, —NHC(O)cyclobutyl, —NHC(O)cyclopentyl, or —NHC(O)cyclohexyl.

In a particular embodiment, this invention relates to compounds of Formula (I) or pharmaceutically acceptable salts thereof wherein:

X is CH; and $R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, methyl, trifluoromethyl, oxo, hydroxyl, methoxy, ethoxy, isopropyloxy, isobutyloxy, difluoromethoxy, trifluoromethoxy, and cyclopentyloxy.

In a particular embodiment, this invention relates to compounds of Formula (I) or pharmaceutically acceptable salts thereof wherein:

X is N;

$R^1$ is $(C_1-C_4)$alkyl, hydroxy$(C_1-C_4)$alkyl, cyclopropyl, cyclobutyl, cyclopentyl, cyclohexyl, azetidinyl, oxetanyl, pyrrolidinyl, piperidinyl, piperazinyl, morpholinyl, thiomorpholinyl, tetrahydropyranyl, phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said phenyl, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl is optionally substituted with one or two substituents independently selected from chlorine, methyl, trifluoromethyl, oxo, hydroxyl, methoxy, ethoxy, isopropyloxy, isobutyloxy, difluoromethoxy, trifluoromethoxy, and cyclopentyloxy.

This invention also relates to compounds that are exemplified in the Experimental section.

Specific compounds of this invention include:

4-amino-6-(1-(oxetan-3-yl)-1H-indol-5-yl)-7,8-dihydropyrimido[5,4-f][1,4]oxazepin-5(6H)-one;

4-amino-6-(1-(3-(trifluoromethoxy)phenyl)-1H-indol-5-yl)-7,8-dihydropyrimido[5,4-f][1,4]oxazepin-5(6H)-one;

4-amino-6-(1-cyclobutyl-1H-pyrrolo[2,3-b]pyridin-5-yl)-7,8-dihydropyrimido[5,4-f][1,4]oxazepin-5(6H)-one;

4-amino-6-(1-(2-hydroxy-2-methylpropyl)-1H-indol-5-yl)-7,8-dihydropyrimido[5,4-f][1,4]oxazepin-5(6H)-one;

4-amino-6-(1-(2-(trifluoromethoxy)phenyl)-1H-indol-5-yl)-7,8-dihydropyrimido[5,4-f][1,4]oxazepin-5(6H)-one;

4-amino-6-(1-(2-methoxy-4-(trifluoromethyl)phenyl)-1H-indol-5-yl)-7,8-dihydropyrimido[5,4-f][1,4]oxazepin-5(6H)-one;

4-amino-6-(1-(3-(difluoromethoxy)phenyl)-1H-indol-5-yl)-7,8-dihydropyrimido[5,4-f][1,4]oxazepin-5(6H)-one;

4-amino-6-(1-(3-isobutoxyphenyl)-1H-indol-5-yl)-7,8-dihydropyrimido[5,4-f][1,4]oxazepin-5(6H)-one;

4-amino-6-(1-(2-isopropoxyphenyl)-1H-indol-5-yl)-7,8-dihydropyrimido[5,4-f][1,4]oxazepin-5(6H)-one;

4-amino-6-(1-(3,5-dichlorophenyl)-1H-indol-5-yl)-7,8-dihydropyrimido[5,4-f][1,4]oxazepin-5(6H)-one;

4-amino-6-(1-(3,5-dichlorophenyl)-1H-pyrrolo[2,3-b]pyridin-5-yl)-7,8-dihydropyrimido[5,4-f][1,4]oxazepin-5(6H)-one;

4-amino-6-(1-(2,3-dichlorophenyl)-1H-indol-5-yl)-7,8-dihydropyrimido[5,4-f][1,4]oxazepin-5(6H)-one;
4-amino-6-(1-(2-methylpyrimidin-5-yl)-1H-indol-5-yl)-7,8-dihydropyrimido[5,4-f][1,4]oxazepin-5(6H)-one;
4-amino-6-(1-(6-methylpyridin-3-yl)-1H-pyrrolo[2,3-b]pyridin-5-yl)-7,8-dihydropyrimido[5,4-f][1,4]oxazepin-5(6H)-one;
4-amino-6-(1-(1-methyl-6-oxo-1,6-dihydropyridin-3-yl)-1H-indol-5-yl)-7,8-dihydropyrimido[5,4-f][1,4]oxazepin-5(6H)-one;
4-amino-6-(1-(2-hydroxyphenyl)-1H-indol-5-yl)-7,8-dihydropyrimido[5,4-f][1,4]oxazepin-5(6H)-one;
4-amino-6-(1-(2-(cyclopentyloxy)phenyl)-1H-indol-5-yl)-7,8-dihydropyrimido[5,4-f][1,4]oxazepin-5(6H)-one;
4-amino-6-(1-(2-hydroxyphenyl)-1H-pyrrolo[2,3-b]pyridin-5-yl)-7,8-dihydropyrimido[5,4-f][1,4]oxazepin-5(6H)-one;
4-amino-6-(1-(2-(cyclopentyloxy)phenyl)-1H-pyrrolo[2,3-b]pyridin-5-yl)-7,8-dihydropyrimido[5,4-f][1,4]oxazepin-5(6H)-one;
4-amino-6-(1-(2-ethoxyphenyl)-1H-indol-5-yl)-7,8-dihydropyrimido[5,4-f][1,4]oxazepin-5(6H)-one;
4-amino-6-(1-(5-methyl-1,3,4-oxadiazol-2-yl)-1H-indol-5-yl)-7,8-dihydropyrimido[5,4-f][1,4]oxazepin-5(6H)-one;
4-amino-6-(7-cyclopropyl-1-propyl-1H-indol-5-yl)-7,8-dihydropyrimido[5,4-f][1,4]oxazepin-5(6H)-one;
N-(5-(4-amino-5-oxo-7,8-dihydropyrimido[5,4-f][1,4]oxazepin-6(5H)-yl)-1-(2-methoxy phenyl)-1H-indol-7-yl)cyclopropanecarboxamide;
4-amino-6-(1-isopropyl-7-morpholino-1H-indol-5-yl)-7,8-dihydropyrimido[5,4-f][1,4]oxazepin-5(6H)-one;
N-(5-(4-amino-5-oxo-7,8-dihydropyrimido[5,4-f][1,4]oxazepin-6(5H)-yl)-1-isopropyl-1H-indol-7-yl)cyclopropanecarboxamide;
4-amino-6-(7-cyclopropyl-1-(6-methylpyridin-3-yl)-1H-indol-5-yl)-7,8-dihydropyrimido[5,4-f][1,4]oxazepin-5(6H)-one;
4-amino-6-(1-(2-ethylpyrimidin-5-yl)-1H-indol-5-yl)-7,8-dihydropyrimido[5,4-f][1,4]oxazepin-5(6H)-one;
4-amino-6-(1-chloro-2-methoxyphenyl)-1H-indol-5-yl)-7,8-dihydropyrimido[5,4-f][1,4]oxazepin-5(6H)-one;
4-amino-6-(1-(2-methoxy-4-methylphenyl)-1H-indol-5-yl)-7,8-dihydropyrimido[5,4-f][1,4]oxazepin-5(6H)-one;
4-amino-6-(1-(tetrahydro-2H-pyran-4-yl)-1H-indol-5-yl)-7,8-dihydropyrimido[5,4-f][1,4]oxazepin-5(6H)-one;
4-amino-6-(1-(2-methoxy-6-methylpyridin-3-yl)-1H-indol-5-yl)-7,8-dihydropyrimido[5,4-f][1,4]oxazepin-5(6H)-one;
4-amino-6-(1-(2-methoxypyrimidin-5-yl)-1H-indol-5-yl)-7,8-dihydropyrimido[5,4-f][1,4]oxazepin-5(6H)-one;
4-amino-6-(1-(2-ethylphenyl)-1H-indol-5-yl)-7,8-dihydropyrimido[5,4-f][1,4]oxazepin-5(6H)-one;
4-amino-6-(1-(5-methylpyrazin-2-yl)-1H-indol-5-yl)-7,8-dihydropyrimido[5,4-f][1,4]oxazepin-5(6H)-one;
4-amino-6-(1-(5-methyl-4H-1,2,4-triazol-3-yl)-1H-indol-5-yl)-7,8-dihydropyrimido[5,4-f][1,4]oxazepin-5(6H)-one; and
4-amino-6-(1-(2-bromo-3-methoxyphenyl)-1H-indol-5-yl)-7,8-dihydropyrimido[5,4-f][1,4]oxazepin-5(6H)-one;
or pharmaceutically acceptable salts thereof.

A person of ordinary skills in the art recognizes that compounds of the present invention may have alternative names when different naming software is used.

This invention also relates to compounds of Formula (I) or any of the exemplified compounds, or their pharmaceutically acceptable salts thereof, for use in therapy. In particular, for use in the treatment of diseases mediated by Acyl coenzyme A: diacylglycerol acyltransferase 1 (DGAT-1), such as obesity, obesity related disorders, genetic (Type 1, Type 5 hyperlipidemia) and acquired forms of hypertriglyceridemia or hyperlipoproteinemia-related disorders, hyperlipoproteinemia, chylomicronemia, dyslipidemia, non-alcoholic steatohepatitis, diabetes, insulin resistance, metabolic syndrome, cardiovascular outcomes, angina, excess hair growth (including syndromes associated with hirsutism), nephrotic syndrome, fibrosis such as myocardial, renal and liver fibrosis, hepatitis C virus infection and acne or other skin disorders. In particular, this invention relates to compounds of Formula (I), or any of the exemplified compounds, or their pharmaceutically acceptable salts thereof, for use in the treatment of obesity.

This invention also relates to compounds of Formula (I) or any of the exemplified compounds, or their pharmaceutically acceptable salts thereof, for use as a medicament. This invention also relates to compounds of Formula (I) or any of the exemplified compounds, or their pharmaceutically acceptable salts thereof, in the manufacture of a medicament for the treatment of obesity.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$ or $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "($C_1$-$C_4$)alkyl" refers to an alkyl moiety containing from 1 to 4 carbon atoms. Exemplary alkyls include, but are not limited to methyl, ethyl, n-propyl, isopropyl, n-butyl, isobutyl, s-butyl, and t-butyl.

When the term "alkyl" is used in combination with other substituent groups, such as "halo($C_1$-$C_4$)alkyl" or "hydroxy($C_1$-$C_4$)alkyl", the term "alkyl" is intended to encompass a divalent straight or branched-chain hydrocarbon radical, wherein the point of attachment is through the alkyl moiety. "halo($C_1$-$C_4$)alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo($C_1$-$C_4$)alkyl" groups useful in the present invention include, but are not limited to, —$CHF_2$ (difluoromethyl), —$CF_3$ (trifluoromethyl), —$CCl_3$ (trichloromethyl), 1,1-difluoroethyl, 2,2,2-trifluoroethyl, and hexafluoroisopropyl. Examples of "hydroxy($C_1$-$C_4$)alkyl" groups useful in the present invention include, but are not limited to, hydroxymethyl, hydroxyethyl, and hydroxyisopropyl.

As used herein, the term "cycloalkyl" refers to a non-aromatic, saturated, cyclic hydrocarbon ring containing the specified number of carbon atoms. The term "($C_3$-$C_7$)cycloalkyl" refers to a non-aromatic cyclic hydrocarbon ring having from three to seven ring carbon atoms. Exemplary "($C_3$-$C_7$)cycloalkyl" groups useful in the present invention include, but are not limited to, cyclopropyl, cyclobutyl, cyclopentyl, cyclohexyl, and cycloheptyl.

"Alkoxy" refers to a group containing an alkyl radical, defined hereinabove, attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, isobutoxy, and t-butoxy.

The term "halo($C_1$-$C_4$)alkoxy" refers to a straight- or branched-chain hydrocarbon radical, having at least 1 and up to 4 carbon atoms with one or more halogen atoms, which may be the same or different, attached to one or more carbon atoms, which radical is attached through an oxygen linking atom. Exemplary "halo($C_1$-$C_4$)alkoxy" groups useful in the present invention include, but are not limited to, —OCHF$_2$ (difluoromethoxy), —OCF$_3$ (trifluoromethoxy), and —OCH(CF$_3$)$_2$ (hexafluoroisopropoxy).

"Cycloalkoxy" refers to a group containing a cycloalkyl radical, defined hereinabove, attached through an oxygen linking atom. The term "($C_3$-$C_7$)cycloalkoxy" refers to a non-aromatic, saturated, cyclic hydrocarbon ring having from three to seven ring carbon atoms attached through an oxygen linking atom. Exemplary "($C_3$-$C_7$)cycloalkoxy" groups useful in the present invention include, but are not limited to, cyclopropyloxy, cyclobutyloxy, cyclopentyloxy, cyclohexyloxy, and cycloheptyloxy.

As used herein, "halogen" or "halo" refers to F, Cl, Br, or I. "Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

As used herein, "4- to 6-membered heterocycloalkyl" represents a group or moiety comprising a non aromatic, monovalent monocyclic radical, which is saturated or partially unsaturated, containing 4, 5, or 6 ring atoms, which includes one or two heteroatoms selected independently from oxygen, sulfur, and nitrogen. Illustrative examples of 4- to 6-membered heterocycloalkyl groups useful in the present invention include, but are not limited to azetidinyl, oxetanyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, and 1,3-dithianyl.

As used herein, "5- or 6-membered heteroaryl" represents a group or moiety comprising an aromatic monovalent monocyclic radical, containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Illustrative examples of 5- or 6-membered heteroaryl groups useful in the present invention include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

As used herein, the term "optionally" means that the subsequently described event(s) may or may not occur, and includes both event(s) that occur and event(s) that do not occur.

The term "independently" means that where more than one substituent is selected from a number of possible substituents, those substituents may be the same or different. The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions.

Pharmaceutical Compositions

The invention further provides a pharmaceutical composition (also referred to as pharmaceutical formulation) comprising a compound of Formula (I) or a pharmaceutically acceptable salt thereof, and one or more excipients (also referred to as carriers and/or diluents in the pharmaceutical arts). The excipients are pharmaceutically acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula (I) or a pharmaceutically acceptable salt thereof, with at least one excipient.

Pharmaceutical compositions may be in unit dose form containing a predetermined amount of active ingredient per unit dose. Such a unit may contain a therapeutically effective dose of the compound of Formula (I) or a pharmaceutically acceptable salt thereof, or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules, powders or granules, solutions or suspensions in aqueous or non-aqueous liquids, edible foams or whips, oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as a syrup, starch paste, acadia mucilage, or solutions of cellulosic or polymeric materials and forcing through a screen. As an alternative to granulating, the powder mixture can be run through a tablet machine, resulting in imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

The present invention provides a method of treatment in a mammal, especially a human, suffering from obesity, diabetes, hypertension, depression, anxiety, drug addiction, substance addiction, or a combination thereof. Such treatment comprises the step of administering a therapeutically effective amount of a compound of Formula (I) or a pharmaceutically acceptable salt thereof, to said mammal, particularly a human. Treatment can also comprise the step of administering a therapeutically effective amount of a pharmaceutical composition containing a compound of Formula (I) or a pharmaceutically acceptable salt thereof, to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition. While it is possible that, for use in therapy, a therapeutically effective amount of a compound of Formula (I) or a pharmaceutically acceptable salt thereof, may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or a pharmaceutically acceptable salt thereof, will be given for the treatment in the range of about 0.1 to 100 mg/kg body weight of recipient (patient, mammal) per day and more usually in the range of 0.1 to 10 mg/kg body weight per day. Acceptable daily dosages may be from about 0.1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) per se. Similar dosages should be appropriate for treatment of the other conditions referred herein for treatment. In general, determination of appropriate dosing can be readily arrived at by one skilled in medicine or the pharmacy art.

Additionally, the present invention provides the use of a compound of the invention in combination with weight management therapies or other triglyceride lowering therapy. In particular, the present invention provides a combination of a compound of Formula (I) or a pharmaceutically acceptable salt thereof, or a pharmaceutical composition thereof with at least one other therapeutically active agent, including another anti-obesity drug and/or an anti-diabetes drug. Such other therapeutically active agent can include, for example, metformin (Glucophage®), CB1 receptor antagonists, GLP-1 agonists, opioid antagonists, and neurotransmitter reuptake inhibitors. When a compound of the invention is employed in combination with another anti-obesity drug or anti-diabetes drug, it is to be appreciated by those skilled in the art that the dose of each compound or drug of the combination may differ from that when the drug or compound is used alone. Appropriate doses will be readily appreciated and determined by those skilled in the art. The appropriate dose of the compound of Formula (I) or a pharmaceutically acceptable salt thereof, and the other therapeutically active agent(s) and the relative timings of administration will be selected in order to achieve the desired combined therapeutic effect, and are within the expertise and discretion of the attending doctor or clinician.

Compounds Preparation

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-5 by those skilled in the art. In the following description, the groups are as defined above for compounds of Formula (I) unless otherwise indicated. Starting materials are commercially available or are made from commercially available materials using methods known to those skilled in the art.

Compounds of Formula (I) may be prepared as illustrated in Scheme 1. An appropriately substituted 5-bromo indole or azaindole derivative A can be treated with an aptly substituted alkyl (or cycloalkyl or heterocycloalkyl) or a phenyl (or heteroaryl) coupling precursor such as a bromide, iodide, or triflate under suitable conditions to effect the corresponding alkylation or arylation to afford the indole or azaindole derivative B. Indole or azaindole B can be subjected to amination under Buchwald conditions using an appropriately protected ethanolamine in the presence of reagents such as palladium acetate, a ligand such as X-Phos, and a base such as cesium carbonate in toluene at 110° C. Intermediate C thus obtained can then be coupled to 4,6-dichloropyrimidine-5-carbonyl chloride to afford D. Desilylation of intermediate D under standard TBAF conditions leads to E which is then subjected to ring closure by heating the reaction mixture in acetonitrile at 80° C. in the presence of a base such as triethylamine to give F. Substitution of the chloro residue in intermediate F with an amino group by treatment with ammonia at room temperature results in compounds of Formula (I) (1a).

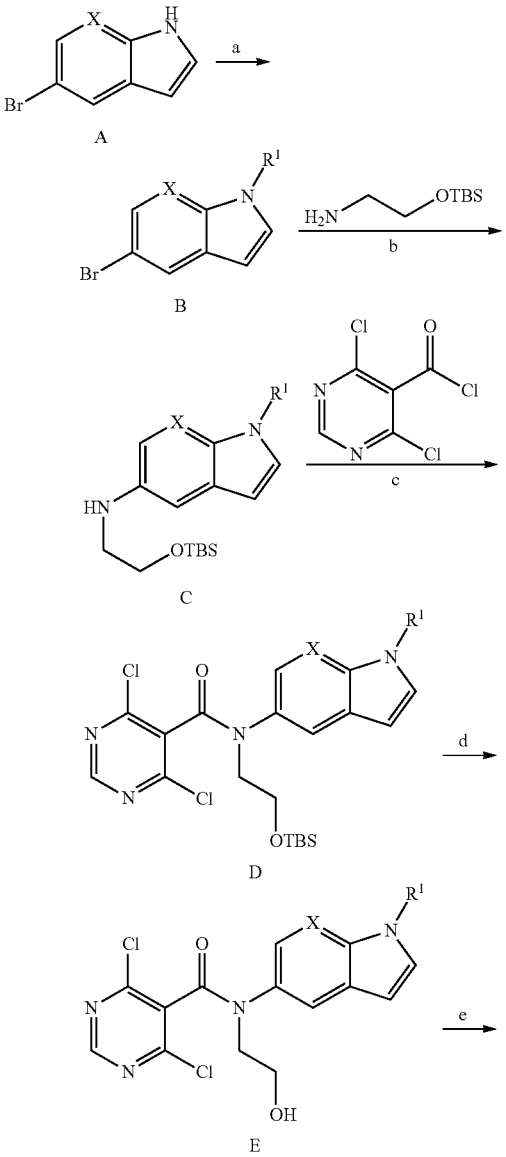

Scheme 1.

19
-continued

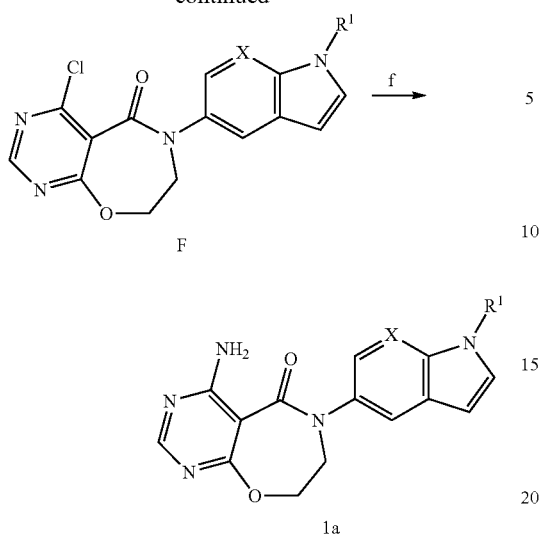

Reagents and conditions: a) R¹—Br or R¹—OTf, Cs₂CO₃, DMF, 70° C. OR R¹—I/R¹—Br, CuBr, Cu(OAc)₂, K₂CO₃, NaOH, DMF, 105° C. OR R¹—I/R¹—Br, CuBr, Cu(OAc)₂, K₂CO₃, NaOH, DMF, 130° C.; b) Pd(OAc)₂, Cs₂CO₃, X-Phos, toluene. 110° C.; c) DCM, Et₃N, RT; d) TBAF, THF, RT; e) CH₃CN, Et₃N, 80° C.; f) NH₃, dioxane, RT.

Compounds of Formula (I) may also be prepared as illustrated in Scheme 2. An appropriately substituted 5-bromo indole or azaindole derivative A can be treated with 1-(benzyloxy)-2-bromobenzene to effect the corresponding arylation affording compound G. Compound G can be subjected to amination under Buchwald conditions using an appropriately protected ethanolamine in the presence of reagents such as palladium acetate, a ligand such as X-Phos, and a base such as cesium carbonate in toluene at 110° C. Intermediate H thus obtained can then be coupled to 4,6-dichloropyrimidine-5-carbonyl chloride to afford I. Desilylation of intermediate I under standard TBAF conditions leads to J which is then subjected to ring closure by heating the reaction mixture in acetonitrile at 80° C. in the presence of a base such as triethylamine to give K. Substitution of the chloro residue in intermediate K with an amino group by treatment with ammonia at room temperature results in the amino pyrimidine L. The masked phenol in L is then revealed under palladium on carbon catalyzed hydrogenolysis conditions to give the phenol M which now can be alkylated with suitable alkyl bromides R—Br under standard conditions to give compounds of Formula (I) (1b).

Scheme 2.

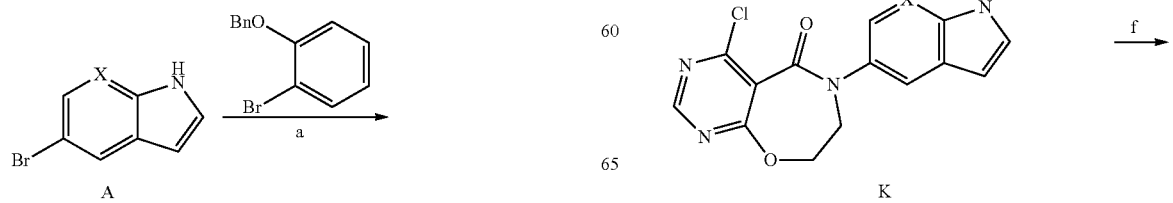

20
-continued

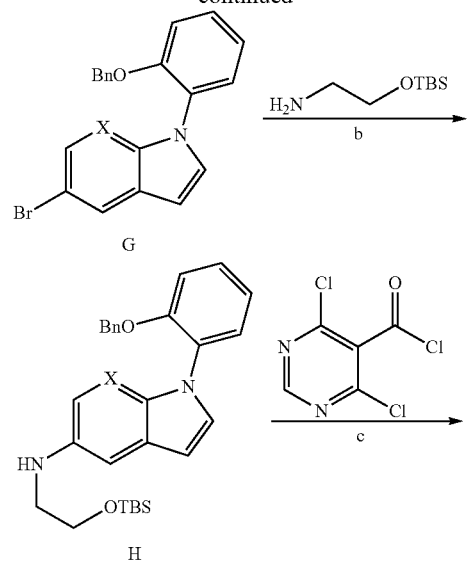

-continued

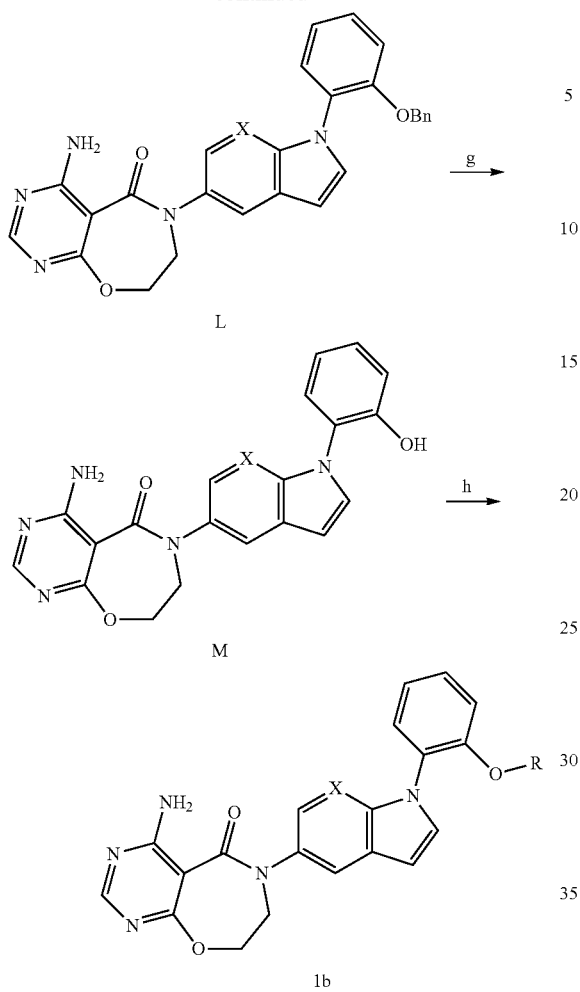

Reagents and conditions: a) CuBr, ethane-1,2-diamine, K₂CO₃, DMF, 100° C.; b) Pd(OAc)₂, Cs₂CO₃, X-Phos, toluene, 100° C.; c) DCM, Et₃N, RT; d) 3N HCl—MeOH, RT; e) CH₃CN, Et₃N, 80° C.; f) NH₃, dioxane, RT; g) MeOH, HCO₂NH₃, Pd/C, reflux; h) R—Br, DMF, Cs₂CO₃, RT.

Compounds of Formula (I) may also be synthesized as illustrated in Scheme 3. An appropriately substituted 5-bromo indole or azaindole derivative A is treated first with phosgene at 0° C. to convert it into a reactive acyl intermediate which then is treated with a suitably substituted acyl hydrazine in the presence of triethylamine at room temperature to afford the diacyl hydrazine N. The conversion of N to oxadiazole derivative O can be achieved by treatment with POCl₃ in refluxing toluene. Aryl bromide O can be subjected to amination under Buchwald conditions using an appropriately protected ethanolamine in the presence of reagents such as palladium acetate, a ligand such as X-Phos, and a base such as cesium carbonate in toluene at 110° C. Intermediate P thus obtained can then be coupled to 4,6-dichloropyrimidine-5-carbonyl chloride to afford Q. Desilylation of intermediate Q under standard acidic conditions leads to R which is then subjected to ring closure by heating the reaction mixture in acetonitrile at 80° C. in the presence of a base such as triethylamine to give S. Substitution of the chloro residue in intermediate S with an amino group by treatment with ammonia at room temperature results in compounds of Formula (I) (1c).

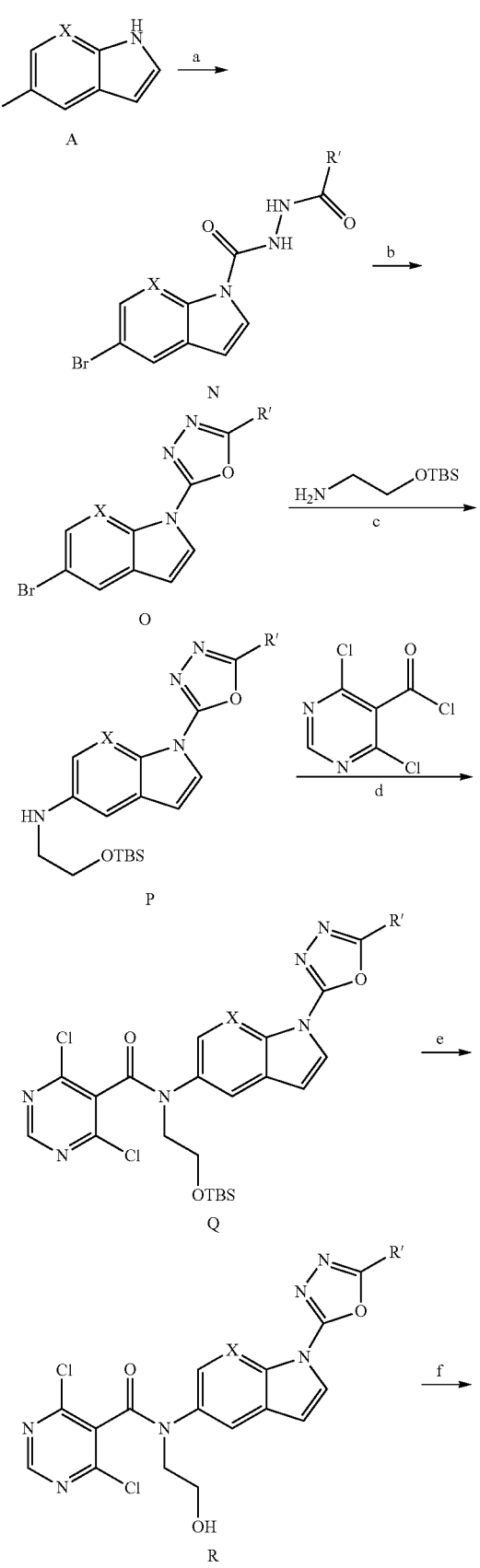

-continued

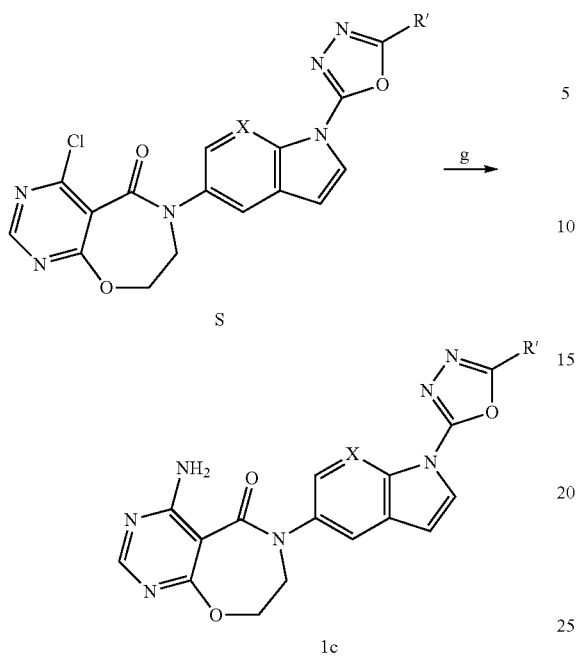

Reagents and conditions: a) 20% COCl₂ in toluene, TEA, THF, 0° C.; then NH₂NHCOR, TEA, RT; b) POCl₃, toluene, 110° C.; c) Pd(OAc)₂, X-Phos, Cs₂CO₃, toluene, 110° C.; d) Et₃N, DCM, RT; e) 3% HCl—MeOH, RT; f) Et₃N, CH₃CN, 80° C.; g) NH₃, dioxane, RT.

Compounds of Formula (I) may also be synthesized as illustrated in Scheme 4. The nitro indoline derivative T is brominated in the first step using bromine in acetic acid to afford the meta-brominated product U. Indoline U is now oxidized to the more stable indole V which is then alkylated (or arylated accordingly) with an appropriate bromide reagent R¹—Br in the presence of cesium carbonate and DMF to give indole W. The bromine in W can now undergo coupling reaction with an appropriate boronic acid (or boronate ester) under standard Suzuki conditions (or an amine under Buchwald conditions) to give 7-substituted indole derivative AA. The nitro group is reduced to the corresponding amine by hydrogenolysis in the presence of palladium on carbon to afford AB Aniline AB can then be alkylated with a suitably substituted bromide under heating conditions to afford intermediate C which can be converted to compounds of Formula (I) (1d) as described in Scheme 1.

Scheme 4.

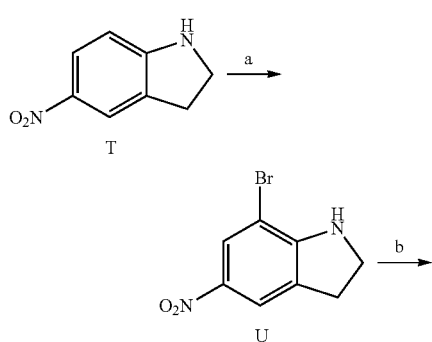

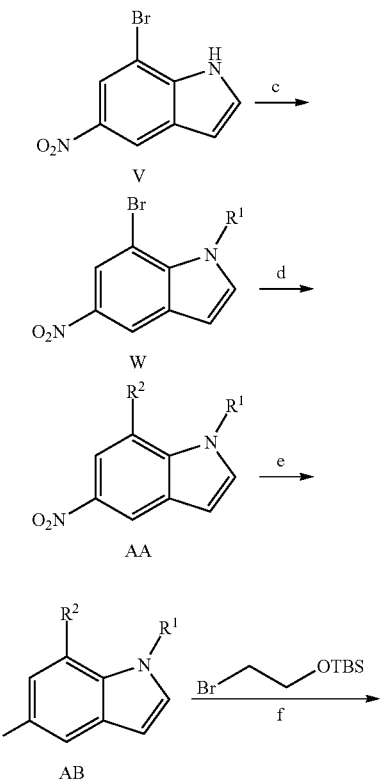

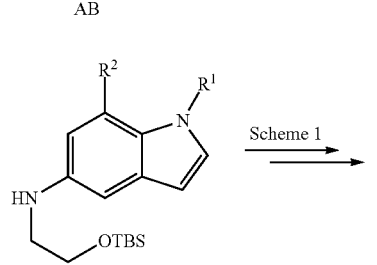

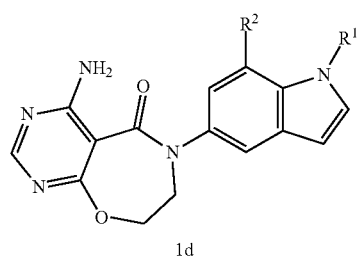

Reagents and conditions: a) Br₂, AcOH, 0° C.; b) DDQ, EtOH, IPA, 80° C.; c) R¹—Br, Cs₂CO₃, DMF, 70° C.; d) R²—B(OH)₂, Cs₂CO₃, PdCl₂(dppf), toluene-H₂O, 100° C.; e) Pd/C, EtOH, H₂, RT; f) K₂CO₃, CH₃CN, 80° C.

Compounds of Formula (I) may also be synthesized as illustrated in Scheme 5. Indole AC can be acylated by treatment with an appropriate acid chloride R''COCl to give indole AD. N-Alkylation or arylation provides intermediate AE. Coupling of bromoindole AE with an appropriately protected ethanolamine under standard Buchwald conditions gives indole derivative AF. Intermediate AF can be converted to compounds of Formula (I) (1e) as described in Scheme 1.

Scheme 5.

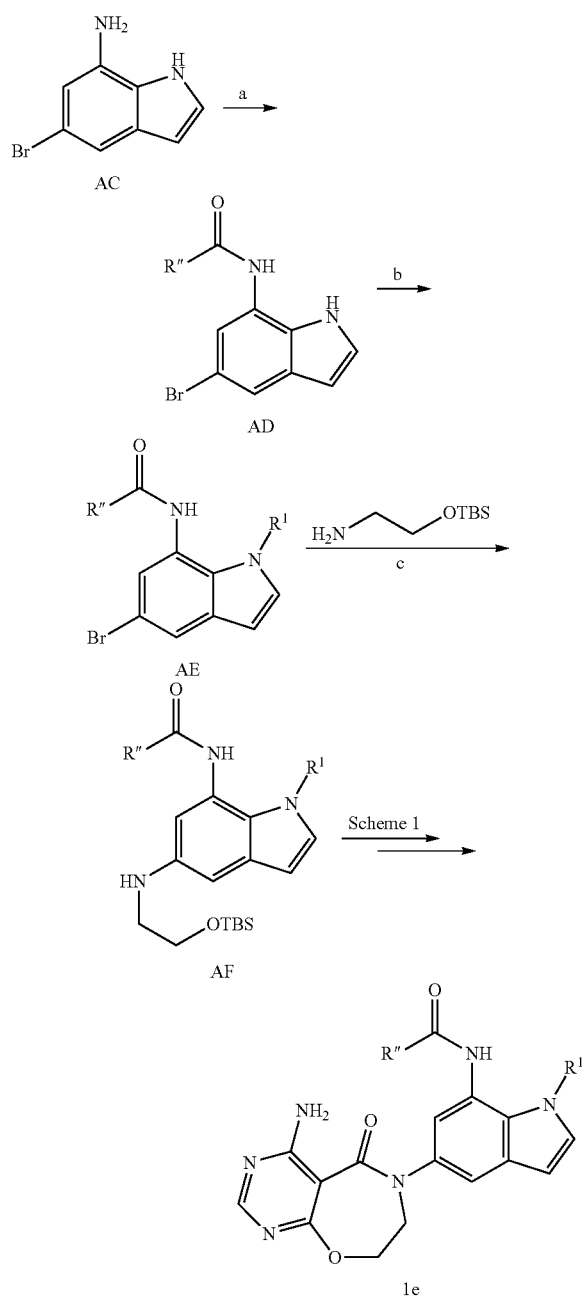

Reagents and conditions: a) R″COCl, DCM, Et₃N, RT; b) R¹—I/R¹—Br, CuBr, Cu(OAc)₂, K₂CO₃, NaOH, DMF, 140° C.; c) Pd(OAc)₂, X-Phos, Cs₂CO₃, toluene, 100° C.

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

The naming program used is ChemDraw®.

Abbreviations

Ac acetyl
ACN acetonitrile
AcOH acetic acid
Cs₂CO₃ cesium carbonate
DCE dichloroethane
DCM dichloromethane
DDQ 2,3-dichloro-5,6-dicyano-1,4-benzoquinone
DMF dimethylformamide
DMSO dimethylsulfoxide
Et₃N triethylamine
EtOH ethanol
g gram(s)
h hour(s)
m/z mass to charge ratio
MeOH methanol
mmol millimoles
NMR nuclear magnetic resonance
Oxz oxazepinones
Pd palladium
Pd/C palladium on carbon
Pd(Cl₂)dppf [1,1'-bis(diphenylphosphino)ferrocene] dichloropalladium(II)
Pd(OAc)₂ palladium acetate
Py pyridine
rt room temperature
TBAF tetrabutylammonium fluoride
TBDMS (TBS) tert-butyldimethylsilyl
Tf₂O trifluoromethanesulfonic anhydride
TFA trifluoroacetic acid
TFAA trifluoroacetic anhydride
THF tetrahydrofuran
X-Phos 2-dicyclohexylphosphino-2',4',6'-triisopropylbiphenyl

Example 1

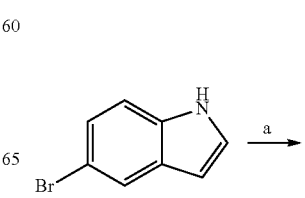

-continued

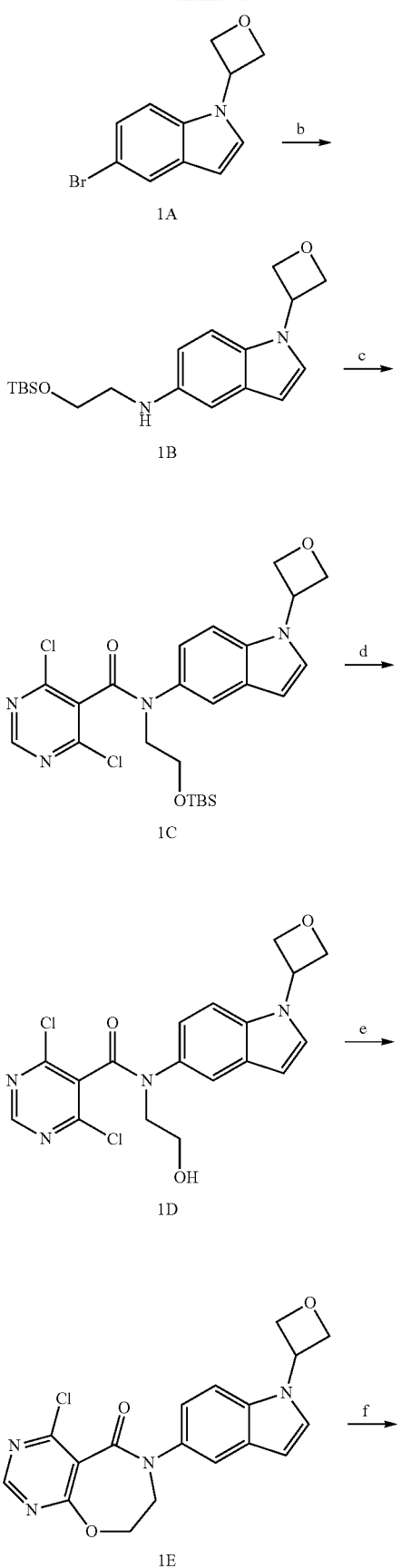

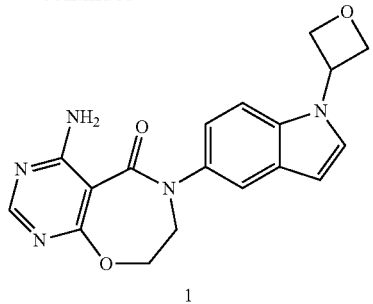

Reagents and conditions: a) Oxetan-3-yl-methanesulfonate, Cs$_2$CO$_3$, DMF, 70° C., 1 h; b) NH$_2$(CH$_2$)$_2$OTBDMS, Pd(OAc)$_2$, Cs$_2$CO$_3$, X-Phos, toluene, 110° C., 12 h; c) 4,6-dichloropyrimidine-5-carbonyl chloride, DCM, Et$_3$N, RT, 4 h; d) TBAF, THF, RT, 2 h e) CH$_3$CN, Et$_3$N, 80° C., 6 h; f) NH$_3$, dioxane, RT, 2 h.

Procedures

4-Amino-6-(1-(oxetan-3-yl)-1H-indol-5-yl)-7,8-dihydropyrimido[5,4-f][1,4]oxazepin-5(6H)-one 5-Bromo-1-(oxetan-3-yl)-1H-pyrrolo[2,3-b]pyridine (1A)

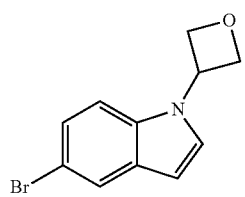 [SMILES: Brc1ccc2c(ccn2C2COC2)c1]

Oxetan-3-yl methanesulfonate (1.397 g, 9.18 mmol) was added to a solution of 5-bromo-1H-indole (1.5 g, 7.65 mmol) in DMF (15 mL) followed by cesium carbonate (3.74 g, 11.48 mmol), and the mixture was stirred at 70° C. for 1 h. Insoluble solids were filtered, the filtrate was concentrated and the residue was partitioned between ethyl acetate and water. Separated organic layer was dried over sodium sulfate and filtered. The filtrate was concentrated under reduced pressure and purified by flash chromatography using 5% ethyl acetate in hexanes to afford the title compound (0.6 g, 30.5%) as an oil. $^1$H NMR (400 MHz, CDCl$_3$): δ 7.77 (d, J=1.6 Hz, 1H), 7.42 (d, J=3.2 Hz, 1H), 7.35 (d, J=8.8 Hz, 1H), 7.30 (dd, J$_1$=2.0 Hz, J$_2$=8.8 Hz, 1H), 6.54 (d, J=2.8 Hz, 1H), 5.58-5.45 (m, 1H), 5.17 (t, J=7.2 Hz, 2H), 5.05 (t, J=6.8 Hz, 2H). ESI-MS m/z=252 (M+H)$^+$.

N-(2-(tert-Butyldimethylsilyloxy)ethyl)-1-(oxetan-3-yl)-1H-indol-5-amine (1B)

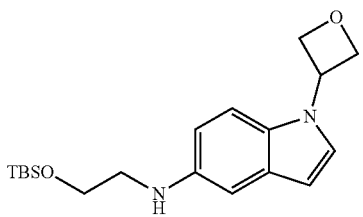 [SMILES: CC(C)(C)[Si](C)(C)OCCNc1ccc2c(ccn2C2COC2)c1]

A mixture of Example 1A (0.6 g, 2.38 mmol), 2-(tert-butyldimethylsilyloxy)ethanamine (0.501 g, 2.86 mmol), cesium carbonate (1.163 g, 3.57 mmol), palladium acetate (0.0534 g, 0.238 mmol) and X-Phos (0.113 g, 0.238 mmol) in toluene (20 mL) was refluxed at 110° C. under argon for 12 h. The reaction mixture was cooled, diluted with ethyl acetate, washed with water (2×20 mL). The separated organic layer was dried over sodium sulfate and filtered. The filtrate was concentrated in vacuo and purified by flash chromatography using 10% ethyl acetate in hexanes to afford the title compound (0.45 g, 33%) as an oil. $^1$H NMR (400 MHz, CDCl$_3$): δ 7.40 (d, J=3.2 Hz, 1H), 7.34-7.30 (m, 2H), 7.02-6.87 (m, 1H), 6.43 (d, J=2.4 Hz, 1H), 5.49 (m, 1H), 5.13 (t, J=6.8 Hz, 2H), 5.05 (t, J=6.8 Hz, 2H), 3.84 (t, J=5.6 Hz, 2H), 3.27 (t, J=5.2 Hz, 2H), 0.89 (s, 9H), 0.06 (s, 6H). ESI-MS m/z=347 (M+H)$^+$.

N-(2-(tert-Butyldimethylsilyloxy)ethyl)-4,6-dichloro-N-(1-(oxetan-3-yl)-1H-indol-5-yl)pyrimidine-5-carboxamide (1C)

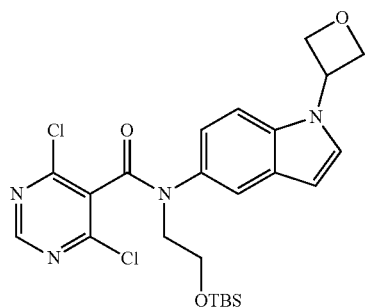 [SMILES: CC(C)(C)[Si](C)(C)OCCN(C(=O)c1c(Cl)ncnc1Cl)c1ccc2c(ccn2C2COC2)c1]

A solution of 4,6-dichloropyrimidine-5-carbonyl chloride (0.276 g, 1.558 mmol) in DCM (5 mL) was added dropwise to an ice-cold solution of Example 1B (0.45 g, 1.299 mmol) and triethylamine (0.543 mL, 3.90 mmol) in DCM (20 mL) and the mixture was stirred for 1 h. The reaction mixture was concentrated in vacuo, and the residue was partitioned between ethyl acetate and water. The separated organic layer was dried over sodium sulphate and filtered. The filtrate was concentrated in vacuo and purified by flash chromatography using 15% ethyl acetate in hexanes to afford the title compound (0.45 g, 62%) as a yellow solid. $^1$H NMR (400 MHz, CDCl$_3$): δ 8.46 (s, 1H), 7.68 (d, J=1.6 Hz, 1H), 7.43 (d, J=3.2 Hz, 1H), 7.27 (d, J=8.8 Hz, 1H), 7.23 (m, 1H), 6.50 (d, J=6.8 Hz, 1H), 5.47 (m, 1H), 5.12 (t, J=7.2 Hz, 2H), 4.97 (t, J=6.8 Hz, 2H), 4.03 (t, J=5.6 Hz, 2H), 3.89 (t, J=5.6 Hz, 2H), 0.85 (s, 9H), 0.05 (s, 6H). ESI-MS m/z=521 (M+H)$^+$.

4,6-Dichloro-N-(2-hydroxyethyl)-N-(1-(oxetan-3-yl)-1H-indol-5-yl)pyrimidine-5-carboxamide (1D)

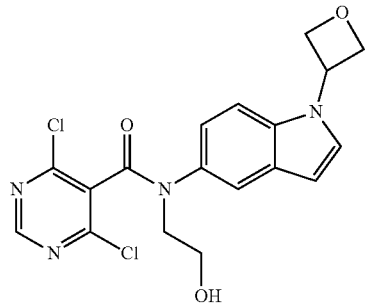 [SMILES: O=C(c1c(Cl)ncnc1Cl)N(CCO)c1ccc2c(ccn2C2COC2)c1]

TBAF (0.301 g, 1.151 mmol) in THF (10 mL) was added to a solution of Example 1C (0.3 g, 0.575 mmol) in THF (5 mL) and stirred at room temperature for 2 h. THF was removed in vacuo, and the residue was partitioned between ethyl acetate and water. The separated organic layer was dried over sodium sulfate and filtered. The filtrate was concentrated in vacuo to afford the title compound (0.21 g, 46%) as a solid. $^1$H NMR (400 MHz, CDCl$_3$): δ 8.49 (s, 1H), 7.69 (d, J=1.2 Hz, 1H), 7.46 (m, 1H), 7.33 (d, J=8.8 Hz, 1H), 7.23 (dd, J$_1$=2.0 Hz, J$_2$=10.4 Hz, 1H), 6.55 (d, J=3.6 Hz, 1H), 5.49 (m, 1H), 5.14 (t, J=8.0 Hz, 2H), 4.99 (t, J=6.8 Hz, 2H), 4.14 (t, J=5.2 Hz, 2H), 3.93 (t, J=5.2 Hz, 2H). ESI-MS m/z=407 (M+H)$^+$.

4-Chloro-6-(1-(oxetan-3-yl)-1H-indol-5-yl)-7,8-dihydropyrimido[5,4-f][1,4]oxazepin-5(6H)-one (1E)

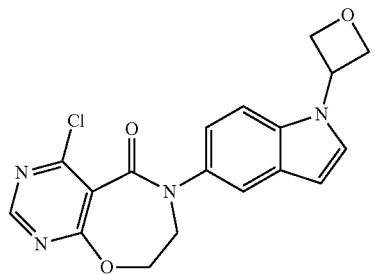 [SMILES: O=C1c2c(Cl)ncnc2OCCN1c1ccc2c(ccn2C2COC2)c1]

A slurry of Example 1D (0.21 g, 0.516 mmol) and triethylamine (0.216 mL, 1.547 mmol) in acetonitrile (8 mL) was stirred at 80° C. for 6 h. The reaction mixture was cooled, concentrated in vacuo and partitioned between ethyl acetate and water. The separated organic layer was dried over sodium sulfate and filtered, and the filtrate was concentrated in vacuo to afford the title compound (0.16 g, 73%) as a white solid. $^1$H NMR (400 MHz, CDCl$_3$): δ 8.77 (s, 1H), 7.63 (d, J=1.6 Hz, 1H), 7.58 (d, J=9.2 Hz, 1H), 7.48 (d, J=2.8 Hz, 1H), 7.22 (dd, J$_1$=1.6 Hz, J$_2$=8.8 Hz, 1H), 6.64 (d, J=3.6 Hz, 1H), 5.57 (m, 1H), 5.20 (t, J=7.2 Hz, 2H), 5.07 (t, J=6.8 Hz, 2H), 4.80 (t, J=4.8 Hz, 2H), 4.08 (t, J=5.2 Hz, 2H). ESI-MS m/z=371 (M+H)$^+$.

4-Amino-6-(1-(oxetan-3-yl)-1H-indol-5-yl)-7,8-dihydropyrimido[5,4-f][1,4]oxazepin-5(6H)-one (1)

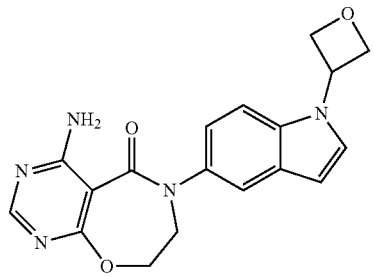 [SMILES: Nc1ncnc2c1C(=O)N(c1ccc3c(ccn3C3COC3)c1)CCO2]

A solution of Example 1E (0.15 g, 0.405 mmol), in 0.5M ammonia in 1,4-dioxane (8 mL) was stirred at room temperature for 2 h. The reaction mixture was concentrated in vacuo and partitioned between ethyl acetate and water. Separated organic layer was dried over sodium sulfate and filtered. The filtrate was concentrated in reduced pressure to afford the title compound (0.08 g, 52.3%) as an off-white solid. $^1$H NMR (300 MHz, DMSO-$d_6$): δ 8.17 (s, 1H), 7.81 (d, J=3.3 Hz, 1H), 7.65-7.58 (m, 3H), 7.55 (d, J=1.8 Hz, 1H), 7.13 (dd, $J_1$=1.8 Hz, $J_2$=9.0 Hz, 1H), 6.58 (d, J=3.0 Hz, 1H), 5.78 (m, 1H), 5.06 (t, J=7.5 Hz, 2H), 4.93 (t, J=6.6 Hz, 2H), 4.64 (t, J=4.5 Hz, 2H), 3.98 (t, J=4.5 Hz, 2H). ESI-MS m/z=352 (M+H)$^+$; HPLC purity: 94%.

Example 2

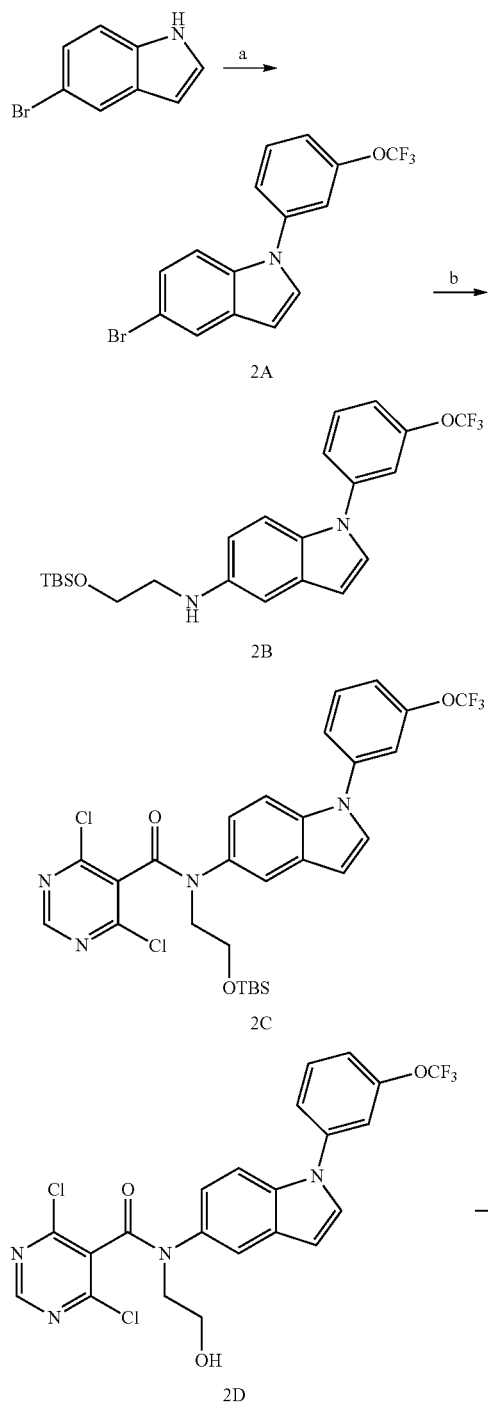

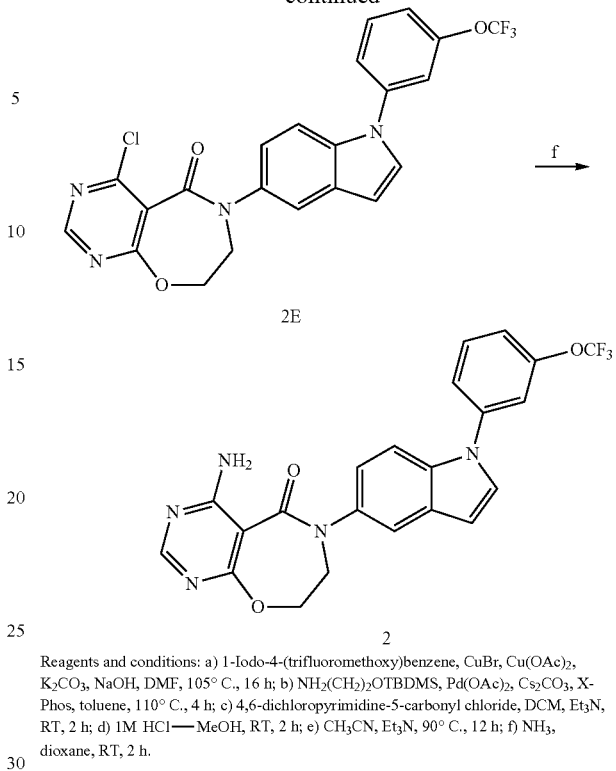

Reagents and conditions: a) 1-Iodo-4-(trifluoromethoxy)benzene, CuBr, Cu(OAc)$_2$, K$_2$CO$_3$, NaOH, DMF, 105° C., 16 h; b) NH$_2$(CH$_2$)$_2$OTBDMS, Pd(OAc)$_2$, Cs$_2$CO$_3$, X-Phos, toluene, 110° C., 4 h; c) 4,6-dichloropyrimidine-5-carbonyl chloride, DCM, Et$_3$N, RT, 2 h; d) 1M HCl—MeOH, RT, 2 h; e) CH$_3$CN, Et$_3$N, 90° C., 12 h; f) NH$_3$, dioxane, RT, 2 h.

Procedures

4-Amino-6-(1-(3-(trifluoromethoxy)phenyl)-1H-indol-5-yl)-7,8-dihydropyrimido[5,4-f][1,4]oxazepin-5(6H)-one 5-Bromo-1-(3-(trifluoromethoxy)phenyl)-1H-indole (2A)

1-Iodo-3-(trifluoromethyl)benzene (2.204 g, 7.65 mmol) was added to a solution of 5-bromo-1H-indole (1.5 g, 7.65 mmol) and copper(I) bromide (0.110 g, 0.765 mmol) in DMF (30 mL) followed by potassium carbonate (2.115 g, 15.30 mmol) and the mixture was stirred at 100° C. for 10 min. NaOH (0.0131 g, 0.765 mmol) and copper(II) acetate (0.138 g, 0.765 mmol) were then added at 110° C., and the reaction mixture was stirred for 16 h. Insoluble solids were filtered, the filtrate was concentrated, and the residue was partitioned between ethyl acetate and water. The separated organic layer was dried over sodium sulphate and filtered, and the filtrate was concentrated in vacuo to afford the title compound (0.8 g, 29%), which was carried on to the next step without any further purification. ESI-MS m/z=356 (M+H)+.

N-(2-(tert-Butyldimethylsilyloxy)ethyl)-1-(3-(trifluoromethoxy)phenyl)-1H-indol-5-amine (2B)

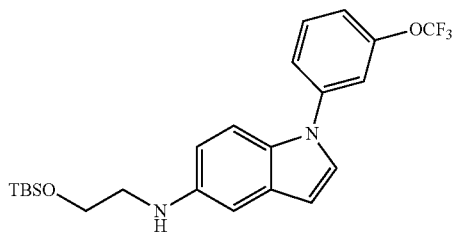 [SMILES: CC(C)(C)[Si](C)(C)OCCNc1ccc2c(ccn2-c2cccc(OC(F)(F)F)c2)c1]

A mixture of Example 2A (0.8 g, 2.246 mmol), 2-(tert-butyldimethylsilyloxy)ethanamine (0.394 g, 2.246 mmol), cesium carbonate (1.098 g, 3.37 mmol), palladium acetate (50.4 mg, 0.225 mmol) and X-Phos (0.107 g, 0.225 mmol) in toluene (20 mL) under argon was refluxed at 110° C. for 4 h. The reaction mixture was warmed to room temperature and partitioned between ethyl acetate and water. The separated organic layer was dried over sodium sulfate and filtered. The filtrate was concentrated in vacuo and purified by flash chromatography using 10% ethyl acetate in hexanes to afford the title compound (0.4 g, 39.5%) as a syrup. $^1$H NMR (400 MHz, CDCl$_3$): δ 7.50 (t, J=8.0 Hz, 1H), 7.44 (d, J=2.4 Hz, 1H), 7.41-7.36 (m, 2H), 7.24 (d, J=3.6 Hz, 1H), 7.15 (d, J=7.6 Hz, 1H), 6.89 (d, J=2.4 Hz, 1H), 6.68 (dd, J$_1$=1.6 Hz, J$_2$=8.8 Hz, 1H), 6.54 (d, J=3.2 Hz, 1H), 3.97 (bs, 1H), 3.86 (t, J=5.6 Hz, 2H), 3.27 (t, J=5.2 Hz, 2H), 0.94 (s, 9H), 0.07 (s, 6H). ESI-MS m/z=451 (M+H)+.

N-(2-(tert-Butyldimethylsilyloxy)ethyl)-4,6-dichloro-N-(1-(3-(trifluoromethoxy)phenyl)-1H-indol-5-yl)pyrimidine-5-carboxamide (2C)

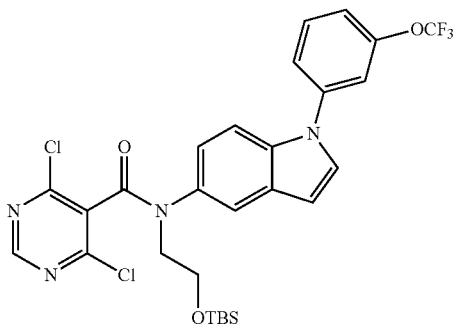 [SMILES: CC(C)(C)[Si](C)(C)OCCN(C(=O)c1c(Cl)ncnc1Cl)c1ccc2c(ccn2-c2cccc(OC(F)(F)F)c2)c1]

A solution of 4,6-dichloropyrimidine-5-carbonyl chloride (0.188 g, 0.888 mmol) in DCM (5 mL) was added dropwise to an ice-cold solution of Example 2B (0.4 g, 0.888 mmol) and triethyl amine (0.188 mL, 3.55 mmol) in DCM (25 mL), and the reaction mixture was stirred for 2 h. This was then concentrated in vacuo, and the residue was partitioned between ethyl acetate and water. The separated organic layer was dried over sodium sulphate and filtered. The filtrate was concentrated in vacuo and purified by flash chromatography using 12% ethyl acetate in hexane to afford the title compound (0.3 g, 54%) as a syrup. $^1$H NMR (400 MHz, CDCl$_3$): δ 8.50 (s, 1H), 7.75 (d, J=1.6 Hz, 1H), 7.54 (t, J=7.6 Hz, 1H), 738-7.30 (m, 5H), 7.22 (s, 1H), 6.62 (d, J=2.8 Hz, 1H), 4.06 (t, J=6.0 Hz, 2H), 3.93 (t, J=5.6 Hz, 2H), 0.88 (s, 9H), 0.07 (s, 6H). ESI-MS m/z=626 (M+H)+.

4,6-Dichloro-N-(2-hydroxyethyl)-N-(1-(3-(trifluoromethoxy)phenyl)-1H-indol-5-yl)pyrimidine-5-carboxamide (2D)

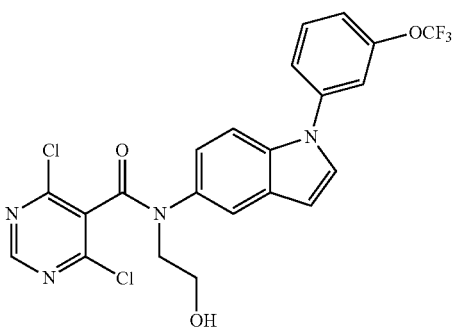 [SMILES: O=C(c1c(Cl)ncnc1Cl)N(CCO)c1ccc2c(ccn2-c2cccc(OC(F)(F)F)c2)c1]

HCl (0.12 mL, 3.29 mmol) was added to a solution of Example 2C (0.3 g, 0.480 mmol) in methanol (15 mL), and the mixture was stirred at room temperature for 1 h. Methanol was removed in vacuo, the residue dissolved in ethyl acetate, washed with saturated aqueous sodium bicarbonate and saturated aqueous brine. The separated organic layer was dried over sodium sulfate and filtered, and the filtrate was concentrated in vacuo to afford the title compound (0.2 g, 82%) as a solid, which was carried on to the next step without further purification. ESI-MS m/z=511 (M+H)+.

4-Chloro-6-(1-(3-(trifluoromethoxy)phenyl)-1H-indol-5-yl)-7,8-dihydropyrimido[5,4-f][1,4]oxazepin-5(6H)-one (2E)

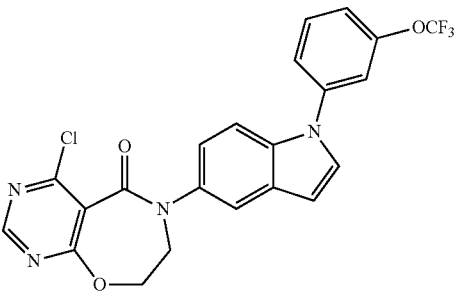 [SMILES: O=C1c2c(Cl)ncnc2OCCN1c1ccc2c(ccn2-c2cccc(OC(F)(F)F)c2)c1]

A slurry of Example 2D (0.2 g, 0.391 mmol) and triethylamine (0.156 mL, 1.565 mmol) in acetonitrile (20 mL) was stirred at 90° C. for 12 h. The reaction mixture was cooled and concentrated in vacuo, and the residue was partitioned between ethyl acetate and water. The separated organic layer was dried over sodium sulfate and filtered, and the filtrate was concentrated in vacuo to afford the title compound (0.15 g, 81%) as a white solid. $^1$H NMR (300 MHz, CDCl$_3$): δ 8.77 (s, 1H), 7.68 (d, J=1.8 Hz, 1H), 7.62-7.55 (m, 3H), 7.46-7.44 (m, 1H), 7.40-7.38 (m, 2H), 7.23 (d, J=2.4 Hz, 1H), 6.75 (d, J=3.3 Hz, 1H), 4.82 (t, J=4.8 Hz, 2H), 4.10 (t, J=4.8 Hz, 2H). ESI-MS m/z=475 (M+H)+.

4-Amino-6-(1-(3-(trifluoromethoxy)phenyl)-1H-indol-5-yl)-7,8-dihydropyrimido[5,4-f][1,4]oxazepin-5(6H)-one (2)

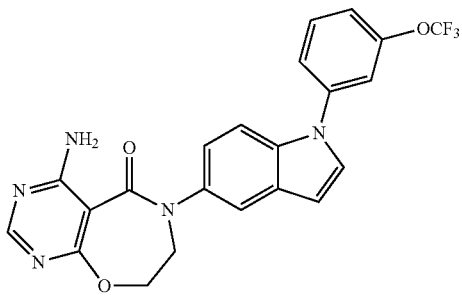 [SMILES: Nc1ncnc2c1C(=O)N(c1ccc3c(ccn3-c3cccc(OC(F)(F)F)c3)c1)CCO2]

A solution of Example 2E (0.15 g, 0.316 mmol) in 0.5 M ammonia in 1,4-dioxane (10 mL) was stirred at room temperature for 2 h. The reaction mixture was concentrated in vacuo, the residue was partitioned between ethyl acetate and water. Separated organic layer was dried over sodium sulfate and filtered. The filtrate was concentrated under reduced pressure to afford the title compound (0.095 g, 59%) as a white solid. $^1$H NMR (400 MHz, DMSO-$d_6$): δ 8.14 (s, 1H), 7.76 (d, J=3.6 Hz, 1H), 7.72-7.57 (m, 7H), 7.39 (d, J=8.0 Hz, 1H), 7.17 (dd, $J_1$=2.0 Hz, $J_2$=8.8 Hz, 1H), 6.74 (d, J=2.8 Hz, 1H), 4.62 (t, J=4.4 Hz, 2H), 3.97 (t, J=4.4 Hz, 2H). ESI-MS m/z=456 (M+H)$^+$; LCMS purity: 91%.

Examples 3-12 were prepared using procedures analogous to those described in Examples 1-2 with appropriate starting materials.

| Exp | Structure | Analytical Data | Mass/Purity |
| --- | --- | --- | --- |
| 3 | 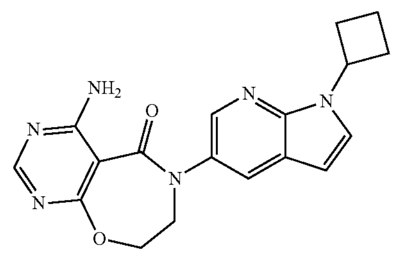 [SMILES: Nc1ncnc2c1C(=O)N(c1cnc3c(ccn3C3CCC3)c1)CCO2] | $^1$H NMR (300 MHz, DMSO-$d_6$): δ 8.22 (d, J = 2.4 Hz, 1H), 8.18 (s, 1H), 7.96 (d, J = 2.1 Hz, 1H), 7.86 (d, J = 3.3 Hz, 1H), 7.64 (bs, 2H), 6.53 (d, J = 3.6 Hz, 1H), 5.29 (m, 1H), 4.67 (t, J = 4.5 Hz, 2H), 4.01 (t, J = 4.8 Hz, 2H), 2.62-2.35 (m, 4H), 1.91-1.80 (m, 2H). | ESI-MS m/z = 351 (M + H)$^+$; HPLC purity: 93%. |
| 4 | 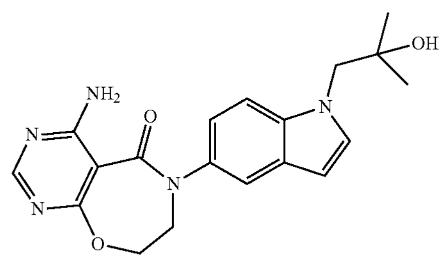 [SMILES: CC(C)(O)Cn1ccc2cc(N3CCOc4ncnc(N)c4C3=O)ccc21] | $^1$H NMR (400 MHz, DMSO-$d_6$): δ 8.17 (s, 1H), 7.60 (bs, 2H), 7.57 (d, J = 8.8 Hz, 1H), 7.47 (s, 1H), 7.38 (d, J = 1.6 Hz, 1H), 7.05 (d, J = 8.4 Hz, 1H), 6.44 (s, 1H), 4.64 (m, 3H), 4.08 (s, 2H), 3.98 (m, 2H), 1.09 (s, 6H). | ESI-MS m/z = 368 (M + H)$^+$; HPLC purity: 96.9%. |
| 5 | 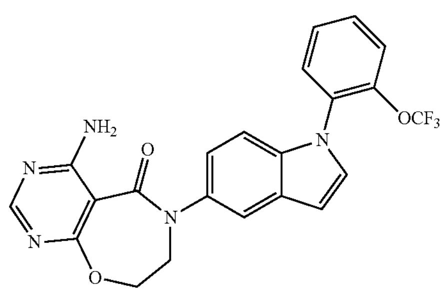 [SMILES: Nc1ncnc2c1C(=O)N(c1ccc3c(ccn3-c3ccccc3OC(F)(F)F)c1)CCO2] | $^1$H NMR (400 MHz, DMSO-$d_6$): δ 8.14 (s, 1H), 7.67-7.60 (m, 7H), 7.55 (d, J = 2.8 Hz, 1H), 7.14-7.10 (m, 2H), 6.72 (d, J = 3.2 Hz, 1H), 4.61 (t, J = 4.0 Hz, 2H), 3.98 (t, J = 4.4 Hz, 2H). | ESI-MS m/z = 456 (M + H)$^+$; HPLC purity: 94%. |
| 6 | 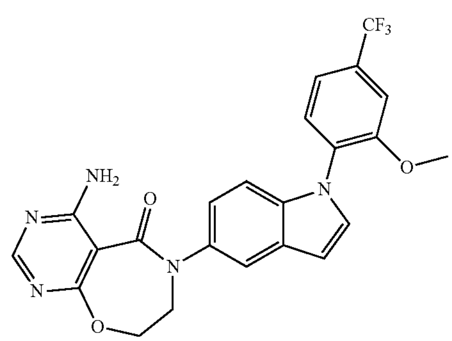 [SMILES: COc1cc(C(F)(F)F)ccc1-n1ccc2cc(N3CCOc4ncnc(N)c4C3=O)ccc21] | $^1$H NMR (400 MHz, DMSO-$d_6$): δ 8.18 (s, 1H), 7.68-7.58 (m, 5H), 7.56 (d, J = 2.8 Hz, 1H), 7.50 (d, J = 8.0 Hz, 1H), 7.18 (d, J = 8.4 Hz, 1H), 7.12 (dd, $J_1$ = 8.8 Hz, $J_2$ = 2.0 Hz, 1H), 6.71 (d, J = 2.8 Hz, 1H), 4.65 (t, J = 4.8 Hz, 2H), 3.99 (t, J = 4.4 Hz, 2H), 3.89 (s, 3H). | ESI-MS m/z = 470 (M + H)$^+$; LCMS purity: 93.7%. |

-continued

| Exp | Structure | Analytical Data | Mass/Purity |
|---|---|---|---|
| 7 | 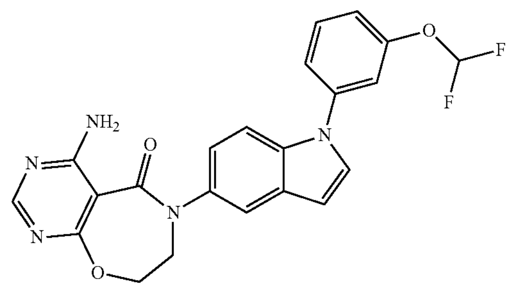 [SMILES: Nc1ncnc2c1C(=O)N(c1ccc3c(ccn3-c3cccc(OC(F)F)c3)c1)CCO2] | $^1$H NMR (400 MHz, DMSO-$d_6$): δ 8.18 (s, 1H), 7.77 (d, J = 3.6 Hz, 1H), 7.70-7.59 (m, 5H), 7.52 (dd, $J_1$ = 1.6 Hz, $J_2$ = 8.4 Hz, 1H), 7.43 (t, J = 2.0 Hz, 1H), 7.40 (s, 1H), 7.22 (dt, $J_1$ = 2.0 Hz, $J_2$ = 8.4 Hz, 2H), 6.75 (d, J = 3.2 Hz, 1H), 4.65 (t, J = 4.4 Hz, 2H), 4.01 (t, J = 4.4 Hz, 2H). | ESI-MS m/z = 438 (M + H)$^+$: HPLC purity: 96%. |
| 8 | 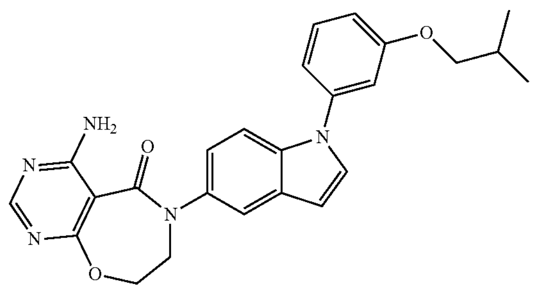 [SMILES: CC(C)COc1cccc(-n2ccc3cc(N4CCOc5ncnc(N)c5C4=O)ccc32)c1] | $^1$H NMR (300 MHz, DMSO-$d_6$): δ 8.18 (s, 1H), 7.73 (d, J = 3.0 Hz, 1H), 7.7-7.6 (m, 3H), 7.48 (t, J = 8.1 Hz, 1H), 7.2-7.1 (m, 4H), 6.99 (d, J = 8.4 Hz, 1H), 6.71 (d, J = 3.3 Hz, 1H), 4.64 (t, J = 4.5 Hz, 2H), 4.01 (t, J = 4.5 Hz, 2H), 3.85 (d, J = 6.6 Hz, 2H), 2.05 (m, 1H), 1.01 (d, J = 6.6 Hz, 6H). | ESI-MS m/z = 444 (M + H)$^+$; HPLC purity: 91.6%. |
| 9 | 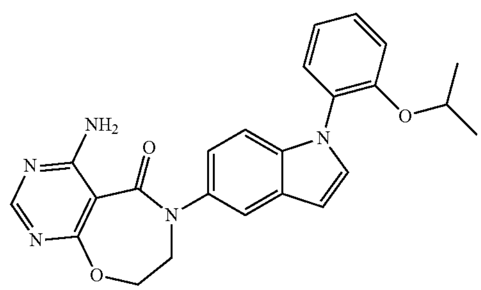 [SMILES: CC(C)Oc1ccccc1-n1ccc2cc(N3CCOc4ncnc(N)c4C3=O)ccc21] | $^1$H NMR (400 MHz, DMSO-$d_6$): δ 8.14 (s, 1H), 7.59 (bs, 2H), 7.55 (d, J = 2.0 Hz, 1H), 7.46 (d, J = 3.6 Hz, 1H), 7.45-7.35 (m, 2H), 7.27 (d, J = 7.6 Hz, 1H), 7.12 (t, J = 8.8 Hz, 1H), 7.05 (m, 2H), 6.62 (d, J = 3.2 Hz, 1H), 4.61 (t, J = 4.8 Hz, 2H), 4.52 (m, 1H), 3.97 (t, J = 4.4 Hz, 2H), 1.10 (d, J = 6.4 Hz, 6H). | ESI-MS m/z = 430 (M + H)$^+$. LCMS purity: 96.4%. |
| 10 | 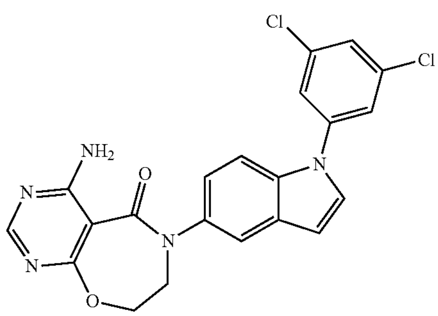 [SMILES: Nc1ncnc2c1C(=O)N(c1ccc3c(ccn3-c3cc(Cl)cc(Cl)c3)c1)CCO2] | $^1$H NMR (400 MHz, DMSO-$d_6$): δ 8.18 (s, 1H), 7.82 (d, J = 2.8 Hz, 1H), 7.74 (s, 2H), 7.70-7.55 (m, 5H), 7.22 (d, J = 8.8 Hz, 1H), 6.77 (d, J = 2.8 Hz, 1H), 4.65 (m, 2H), 4.01 (m, 2H). | ESI-MS m/z = 440 (M + H)$^+$. HPLC purity: 94.4%. |
| 11 | 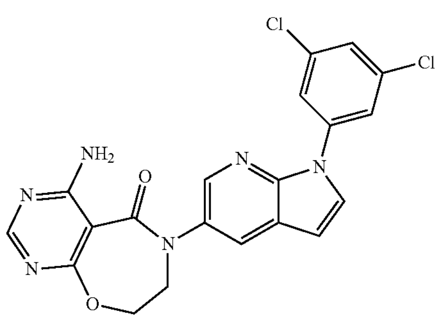 [SMILES: Nc1ncnc2c1C(=O)N(c1cnc3c(ccn3-c3cc(Cl)cc(Cl)c3)c1)CCO2] | $^1$H NMR (300 MHz, DMSO-$d_6$): δ 8.42 (d, J = 2.1 Hz, 1H), 8.22-8.15 (m, 5H), 7.67 (bs, 2H), 7.59 (t, J = 1.5 Hz, 1H), 6.83 (d, J = 3.6 Hz, 1H), 4.70 (t, J = 4.5 Hz, 2H), 4.07 (t, J = 6.9 Hz, 2H). | ESI-MS m/z = 441 (M + H)$^+$. HPLC purity: 97.8%. |

-continued

| Exp | Structure | Analytical Data | Mass/Purity |
|---|---|---|---|
| 12 | 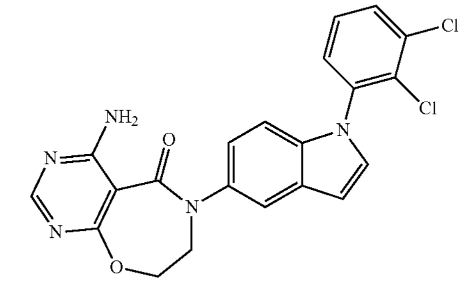 [SMILES: Nc1ncnc2c1C(=O)N(c1ccc3c(ccn3-c3cccc(Cl)c3Cl)c1)CCO2] | $^1$H NMR (300 MHz, DMSO-$d_6$): δ 8.18 (s, 1H), 7.86 (t, J = 5.4 Hz, 1H), 7.65-7.56 (m, 6H), 7.14 (d, $J_1$ = 8.7 Hz, $J_2$ = 1.8 Hz, 1H), 7.08 (d, J = 8.4 Hz, 1H), 6.75 (d, J = 3.3 Hz, 1H), 4.64 (t, J = 5.4 Hz, 2H), 4.02 (t, J = 5.1 Hz, 2H). | ESI-MS m/z: 440 (M + H)$^+$; LCMS purity: 95%. |

Example 13

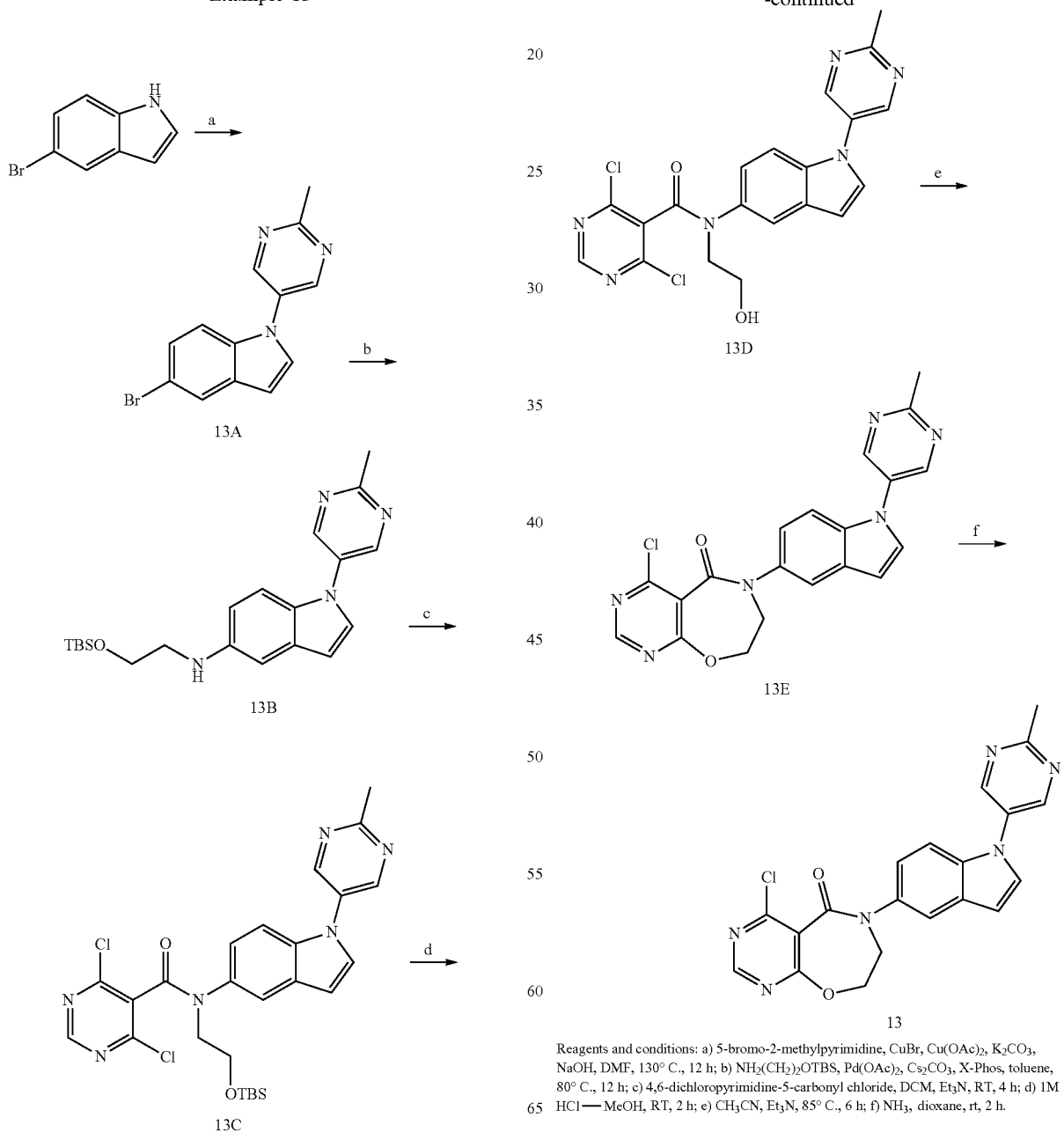

Reagents and conditions: a) 5-bromo-2-methylpyrimidine, CuBr, Cu(OAc)$_2$, K$_2$CO$_3$, NaOH, DMF, 130° C., 12 h; b) NH$_2$(CH$_2$)$_2$OTBS, Pd(OAc)$_2$, Cs$_2$CO$_3$, X-Phos, toluene, 80° C., 12 h; c) 4,6-dichloropyrimidine-5-carbonyl chloride, DCM, Et$_3$N, RT, 4 h; d) 1M HCl—MeOH, RT, 2 h; e) CH$_3$CN, Et$_3$N, 85° C., 6 h; f) NH$_3$, dioxane, rt, 2 h.

Procedures

4-Amino-6-(1-(2-methylpyrimidin-5-yl)-1H-indol-5-yl)-7,8-dihydropyrimido[5,4-f][1,4]oxazepin-5(6H)-one 5-Bromo-1-(2-methylpyrimidin-5-yl)-1H-indole (13A)

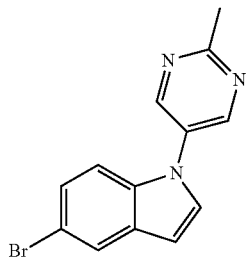 [SMILES: Cc1ncc(-n2ccc3cc(Br)ccc32)cn1]

5-Bromo-2-methyl pyrimidine (0.971 g, 5.61 mmol) was added to a solution of 5-bromo-1H-indole (1 g, 5.1 mmol) and copper(I) bromide (0.073 g, 0.51 mmol) in DMF (10 mL) followed by potassium carbonate (1.762 g, 12.75 mmol), and the resulting mixture was stirred at 100° C. for 10 min. NaOH (0.153 g, 3.83 mmol) and copper(II) acetate (0.009 g, 0.051 mmol) were added at 110° C., and the reaction mixture was stirred for 16 h. Insoluble solids were filtered, and the filtrate was concentrated. The residue was partitioned between ethyl acetate and water. Separated organic layer was dried over sodium sulphate and filtered. The filtrate was concentrated in vacuo and purified by flash chromatography using 10% ethyl acetate in hexane to afford the title compound (0.25 g, 16%) as an off-white solid. $^1$H NMR (300 MHz, CDCl$_3$): δ 8.81 (s, 2H), 7.83 (d, J=1.5 Hz, 1H), 7.36 (dd, J$_1$=1.8 Hz, J$_2$=8.7 Hz, 1H), 7.33-7.26 (m, 2H), 6.71 (d, J=3.3 Hz, 1H), 2.82 (s, 3H). ESI-MS m/z=288 (M+H)$^+$.

N-(2-(tert-Butyldimethylsilyloxy)ethyl)-1-(2-methylpyrimidin-5-yl)-1H-indol-5-amine (13B)

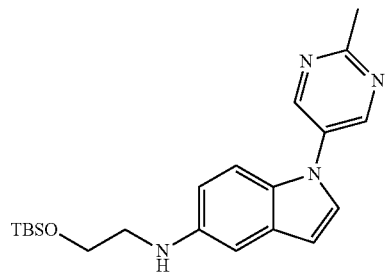 [SMILES: Cc1ncc(-n2ccc3cc(NCCO[Si](C)(C)C(C)(C)C)ccc32)cn1]

A mixture of Example 13A (0.25 g, 0.868 mmol), 2-(tert-butyldimethylsilyloxy)ethanamine (0.183 g, 1.041 mmol), cesium carbonate (0.424 g, 1.301 mmol), palladium acetate (0.019 g, 0.087 mmol) and X-Phos (0.0414 g, 0.087 mmol) in toluene (10 mL) under argon was refluxed at 110° C. for 12 h. The reaction mixture was warmed to room temperature and partitioned between ethyl acetate and water. Separated organic layer was dried over sodium sulfate and filtered. The filtrate was concentrated in vacuo and purified by flash chromatography using 15% ethyl acetate in hexane to afford the title compound (0.15 g, 32%) as a pale yellow syrup. $^1$H NMR (300 MHz, CDCl$_3$): δ 8.82 (s, 2H), 7.31 (d, J=8.7 Hz, 1H), 7.18 (d, J=3.3 Hz, 1H), 6.89 (d, J=2.1 Hz, 1H), 6.70 (dd, J$_1$=2.1 Hz, J$_2$=8.7 Hz, 1H), 6.60 (d, J=3.3 Hz, 1H), 4.0 (bs, 1H), 3.86 (t, J=5.1 Hz, 2H), 3.27 (t, J=5.1 Hz, 2H), 2.81 (s, 3H), 0.92 (s, 9H), 0.08 (s, 6H). ESI-MS m/z=383 (M+H)$^+$.

N-(2-(tert-Butyldimethylsilyloxy)ethyl)-4,6-dichloro-N-(1-(2-methylpyrimidin-5-yl)-1H-indol-5-yl)pyrimidine-5-carboxamide (13C)

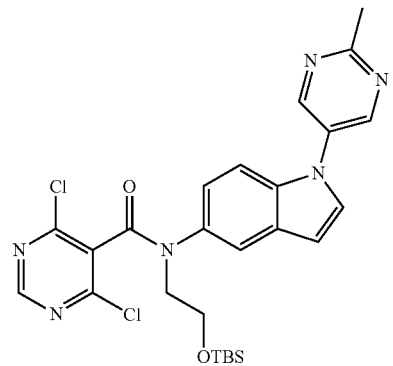 [SMILES: Cc1ncc(-n2ccc3cc(N(CCO[Si](C)(C)C(C)(C)C)C(=O)c4c(Cl)ncnc4Cl)ccc32)cn1]

A solution of 4,6-dichloropyrimidine-5-carbonyl chloride (0.099 g, 0.47 mmol) in DCM (3 mL) was added dropwise to an ice-cold solution of Example 13B (0.15 g, 0.392 mmol) and triethylamine (0.164 mL, 1.176 mmol) in DCM (8 mL), and the mixture was stirred for 4 h. The reaction mixture was concentrated in vacuo, diluted into ethyl acetate and washed with water (2×15 mL). The separated organic layer was dried over sodium sulphate and filtered. The filtrate was concentrated in vacuo and purified by flash chromatography using 15% ethyl acetate in hexanes to afford the title compound (0.1 g, 36%) as a pale yellow solid. $^1$H NMR (400 MHz, CDCl$_3$): δ 8.78 (s, 2H), 8.50 (s, 1H), 7.77 (d, J=2.0 Hz, 1H), 7.31 (dd, J$_1$=2.0 Hz, J$_2$=8.8 Hz, 1H), 7.28-7.26 (m, 2H), 6.68 (d, J=3.2 Hz, 1H), 4.06 (t, J=5.6 Hz, 2H), 3.93 (t, J=6.0 Hz, 2H), 2.83 (s, 3H), 0.88 (s, 9H), 0.07 (s, 6H). ESI-MS m/z=557 (M+H)$^+$.

4,6-Dichloro-N-(2-hydroxyethyl)-N-(1-(2-methylpyrimidin-5-yl)-1H-indol-5-yl)pyrimidine-5-carboxamide (13D)

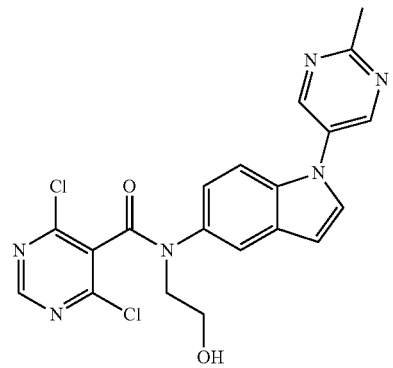 [SMILES: Cc1ncc(-n2ccc3cc(N(CCO)C(=O)c4c(Cl)ncnc4Cl)ccc32)cn1]

A solution of Example 13C (0.1 g, 0.179 mmol) in 5 mL of methanolic solution of HCl (1M) was stirred at room temperature for 2 h. Methanol was removed in vacuo, and the residue was dissolved in ethyl acetate and washed with saturated aqueous sodium bicarbonate and saturated aqueous brine. The separated organic layer was dried over sodium sulfate and filtered, and the filtrate was concentrated in vacuo to afford the title compound (0.07 g, 87%) as a white solid. $^1$H NMR (300 MHz, CDCl$_3$): δ 8.76 (s, 2H), 8.53 (s, 1H), 7.70 (s, 1H), 7.32-7.24 (m, 3H), 6.71 (d, J=3.3 Hz, 1H), 4.16 (t, J=5.1 Hz, 2H), 3.95 (t, J=5.1 Hz, 2H), 2.83 (s, 3H). ESI-MS m/z=443 (M+H)$^+$.

4-Chloro-6-(1-(2-methylpyrimidin-5-yl)-1H-indol-5-yl)-7,8-dihydropyrimido[5,4-f][1,4]oxazepin-5(6H)-one (13E)

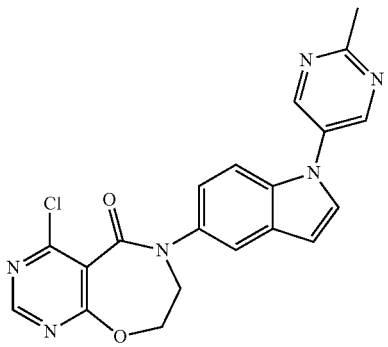 [SMILES: Cc1ncc(-n2ccc3cc(N4CCOc5ncnc(Cl)c5C4=O)ccc32)cn1]

A slurry of Example 13D (0.07 g, 0.158 mmol) and triethylamine (0.066 mL, 0.474 mmol) in acetonitrile (6 mL) was stirred at 85° C. for 6 h. The reaction mixture was cooled and concentrated in vacuo, and the residue was partitioned between ethyl acetate and water. Separated organic layer was dried over sodium sulfate and filtered, and the filtrate was concentrated in vacuo to afford the title compound (0.055 g, 86%) as a white solid. $^1$H NMR (400 MHz, CDCl$_3$): δ 8.85 (s, 2H), 8.77 (s, 1H), 7.71 (d, J=2.0 Hz, 1H), 7.51 (d, J=8.8 Hz, 1H), 7.35 (d, J=3.2 Hz, 1H), 7.27 (dd, J$_1$=2.0 Hz, J$_2$=8.8 Hz, 1H), 6.81 (d, J=3.6 Hz, 1H), 4.82 (t, J=4.4 Hz, 2H), 4.10 (t, J=4.4 Hz, 2H), 2.87 (s, 3H). ESI-MS m/z=407 (M+H)$^+$.

4-Amino-6-(1-(2-methylpyrimidin-5-yl)-1H-indol-5-yl)-7,8-dihydropyrimido[5,4-f][1,4]oxazepin-5(6H)-one (13)

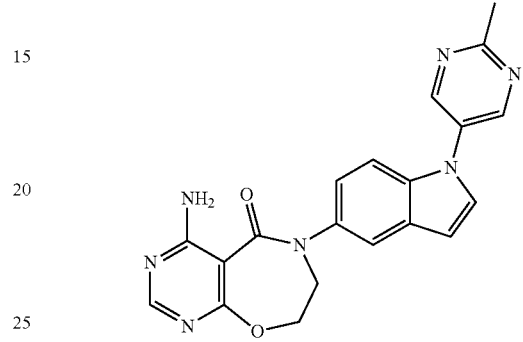

A solution of Example 13E (0.055 g, 0.135 mmol) in 0.5 M ammonia in 1,4-dioxane (6 mL) was stirred at room temperature for 2 h. The reaction mixture was concentrated in vacuo and partitioned between ethyl acetate and water. The separated organic layer was washed with saturated aqueous brine, dried over sodium sulfate and filtered. The filtrate was concentrated in vacuo to afford the title compound (0.035 g, 60%) as a white solid. $^1$H NMR (300 MHz, DMSO-d$_6$): δ 9.03 (s, 2H), 8.18 (s, 1H), 7.81 (d, J=2.7 Hz, 1H), 7.68-7.58 (m, 4H), 7.21 (dd, J$_1$=1.5 Hz, J$_2$=9.0 Hz, 1H), 6.81 (d, J=3.3 Hz, 1H), 4.65 (t, J=3.9 Hz, 2H), 4.01 (t, J=3.9 Hz, 2H), 2.73 (s, 3H). ESI-MS m/z=388 (M+H)$^+$; HPLC purity: 98.8%.

Examples 14-15 were prepared using procedures analogous to those described in Example 13 using appropriate starting materials.

| Exp | Structure | Analytical Data | Mass/Purity |
|---|---|---|---|
| 14 | 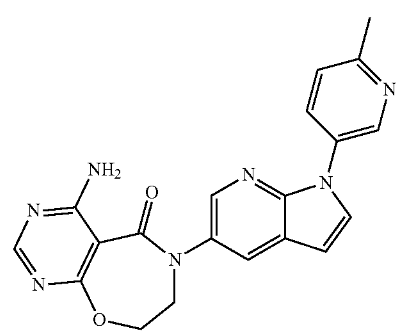 [SMILES: Cc1ccc(-n2ccc3cc(N4CCOc5ncnc(N)c5C4=O)cnc32)cn1] | $^1$H NMR (300 MHz, DMSO-d$_6$): δ 8.95 (d, J = 2.7 Hz, 1H), 8.31 (d, J = 2.1 Hz, 1H), 8.20 (dd, J$_1$ = 8.4 Hz, J$_2$ = 3.0 Hz, 1H), 8.16 (s, 1H), 8.10 (d, J = 2.4 Hz, 1H), 8.03 (d, J = 3.6 Hz, 1H), 7.64 (s, 2H), 7.43 (d, J = 8.7 Hz, 1H), 6.77 (d, J = 3.6 Hz, 1H), 4.66 ((t, J = 5.1 Hz, 2H), 4.03 (t, J = 4.2 Hz, 2H), 2.52 (s, 3H). | ESI-MS m/z = 388 (M + H)$^+$; HPLC purity: 99%. |

| Exp | Structure | Analytical Data | Mass/Purity |
|---|---|---|---|
| 15 | 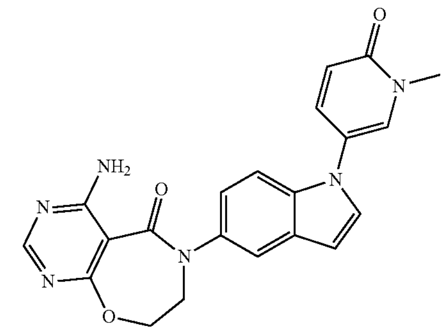 [SMILES: Cn1cc(-n2ccc3cc(N4CCOc5ncnc(N)c5C4=O)ccc32)ccc1=O] | $^1$H NMR (300 MHz, DMSO-d$_6$): δ 8.18 (s, 1H), 8.13 (d, J = 3.0 Hz, 1H), 7.67 (d, J = 3.0 Hz, 1H), 7.66-7.58 (m, 3H), 7.54 (d, J = 3.3 Hz, 1H), 7.42 (d, J = 8.4 Hz, 1H), 7.15 (dd, J$_1$ = 2.1 Hz, J$_2$ = 8.7 Hz, 1H), 6.67 (d, J = 3.0 Hz, 1H), 6.55 (d, J = 9.6 Hz, 1H), 4.65 (t, J = 4.8 Hz, 2H), 3.99 (t, J = 4.5 Hz, 2H), 3.51 (s, 3H). | ESI-MS m/z = 403 (M + H)$^+$; HPLC purity: 95.7%. |
Examples 16 & 17
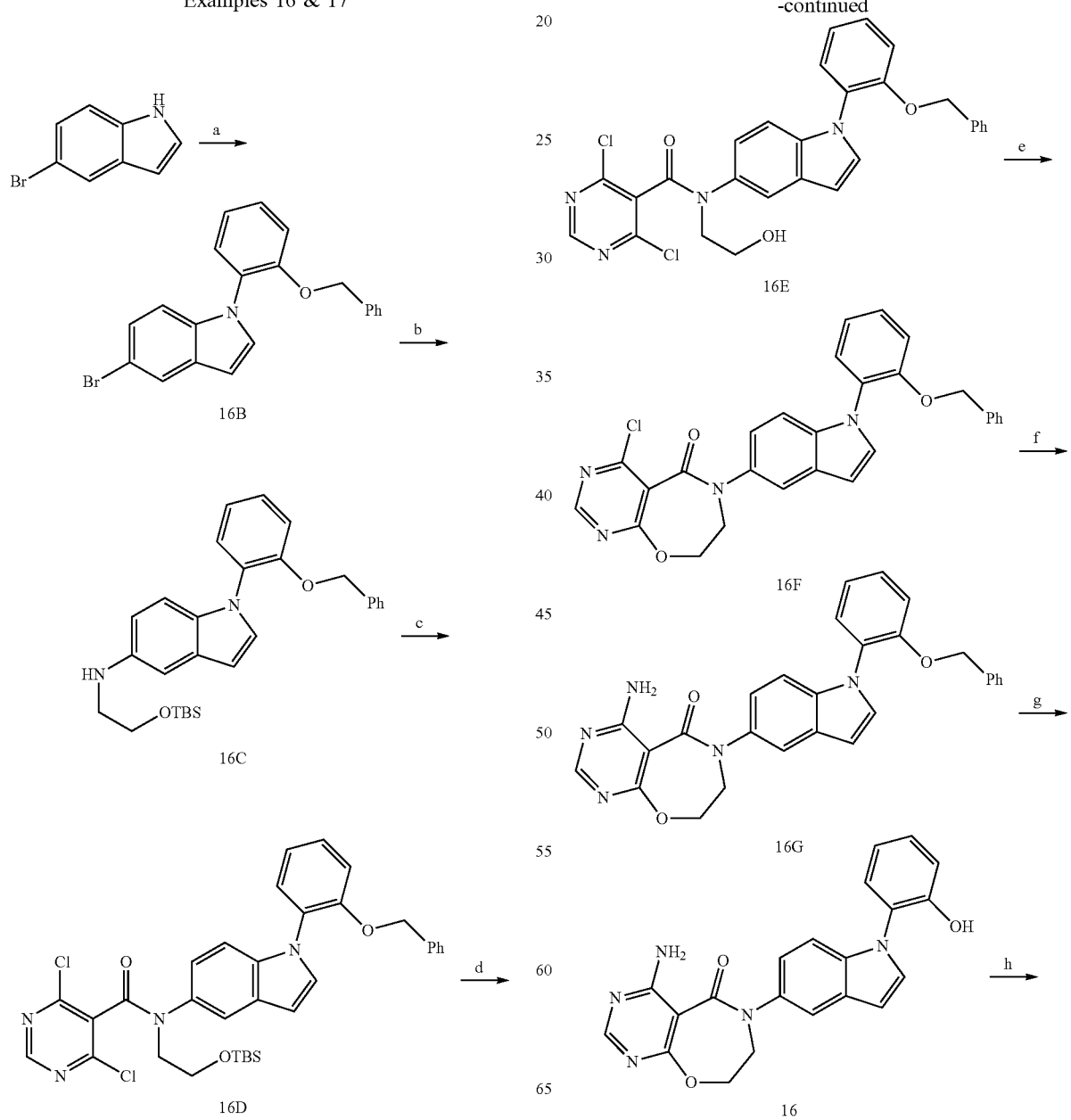

-continued

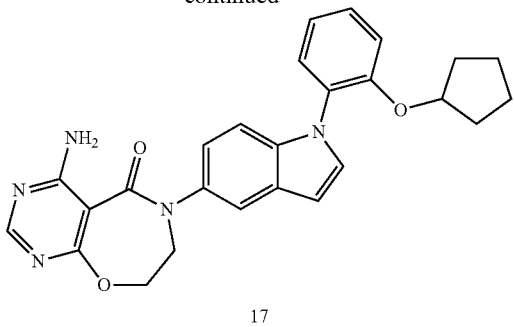

17

Reagents and conditions: a) 1-(Benzyloxy)-2-bromobenzene, CuBr, ethane-1,2-diamine, K₂CO₃, DMF, 100° C., 14 h; b) NH₂(CH₂)₂OTBDMS, Pd(OAc)₂, Cs₂CO₃, X-Phos, toluene, 100° C., 12 h; c) 4,6-dichloropyrimidine-5-carbonyl chloride, DCM, Et₃N, RT, 1 h; d) 3N HCl—MeOH, RT, 1 h; e) CH₃CN, Et₃N, 80° C., 16 h; f) NH₃, dioxane, RT, 2 h; g) MeOH, HCO₂NH₃, Pd/C, reflux, 3 h; h) DMF, Cs₂CO₃, RT, 12 h.

Procedures

4-Amino-6-(1-(2-(cyclopentyloxy)phenyl)-1H-indol-5-yl)-7,8-dihydropyrimido[5,4-f][1,4]oxazepin-5(6H)-one 1-(Benzyloxy)-2-bromobenzene (16A)

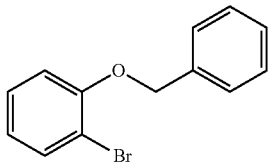 [SMILES: Brc1ccccc1OCc1ccccc1]

Potassium carbonate (47.9 g, 347 mmol) and benzyl bromide (21.75 g, 127 mmol) were added to an ice-cold solution of 2-bromophenol (20 g, 116 mmol) in DMF (200 mL), and the mixture was stirred at room temperature for 4 h. The reaction mixture was partitioned between ethyl acetate and water. Separated organic layer was washed with saturated brine, dried over sodium sulphate and filtered, and the filtrate was concentrated in vacuo to afford the title compound (26 g, 85%) as a syrup, which was carried on to the next step without further purification. ¹H NMR (300 MHz, DMSO-d₆): δ 7.59 (dd, J₁=7.5, J₂=1.2 Hz, 1H), 7.48 (d, J=6.6 Hz, 2H), 7.43-7.31 (m, 4H), 7.18 (dd, J₁=7.2 Hz, J₂=1.2 Hz, 1H), 6.91 (dt, J1=1.2 Hz, J₂=7.8 Hz, 1H), 5.21 (s, 2H). ESI-MS m/z=263 (M+H)⁺.

1-(2-(Benzyloxy)phenyl)-5-bromo-1H-indole (16B)

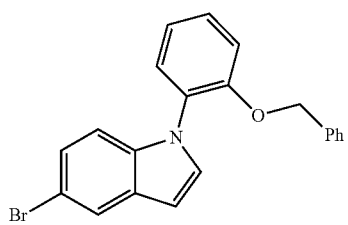 [SMILES: Brc1ccc2c(ccn2-c2ccccc2OCc2ccccc2)c1]

Potassium carbonate (21.15 g, 153 mmol), copper (I) bromide (1.463 g, 10.2 mmol) and ethane-1,2-diamine (0.307 g, 5.1 mmol) were added to a mixture of example 16A (17.45 g, 66.3 mmol) and 5-bromo-1H-indole (10 g, 51.0 mmol) in DMF (80 mL), and the resulting mixture was stirred at 100° C. for 14 h. Insoluble solids were filtered, and the filtrate was concentrated and partitioned between ethyl acetate and water. Separated organic layer was dried over sodium sulphate and filtered, and the filtrate was concentrated in vacuo. The crude product was purified by flash chromatography using 2% ethyl acetate in hexane to afford the title compound (4.5 g, 23%) as an off-white solid. ¹H NMR (300 MHz, DMSO-d₆): δ 7.81 (d, J=1.8 Hz, 1H), 7.54 (d, J=3.0 Hz, 1H), 7.50-7.36 (m, 3H), 7.28-7.08 (m, 8H), 6.63 (d, J=3.0 Hz, 1H), 5.12 (s, 2H). ESI-MS m/z=378 (M+H)⁺.

1-(2-(Benzyloxy)phenyl)-N-(2-(tert-butyldimethylsilyloxy)ethyl)-1H-indol-5-amine (16C)

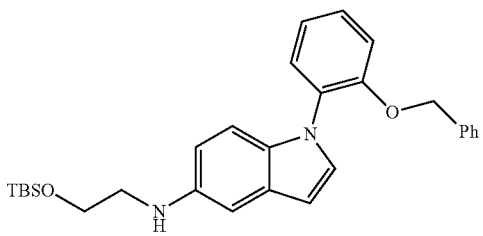 [SMILES: CC(C)(C)[Si](C)(C)OCCNc1ccc2c(ccn2-c2ccccc2OCc2ccccc2)c1]

A mixture of Example 16B (4.5 g, 11.90 mmol), 2-(tert-butyldimethylsilyloxy)ethanamine (4.17 g, 23.79 mmol) and cesium carbonate (11.63 g, 35.7 mmol) in toluene (30 mL) was degassed using argon for 15 min and then palladium acetate (0.40 g, 1.78 mmol) and X-Phos (0.85 g, 1.78 mmol) were added. The resulting mixture was stirred at 100° C. for 12 h. The reaction mixture was warmed to room temperature, diluted into ethyl acetate and washed with water. Separated organic layer was dried over sodium sulfate and filtered. The filtrate was concentrated in vacuo and purified by flash chromatography using 10% ethyl acetate in hexane to afford the title compound (2.6 g, 46%) as a syrup. ¹H NMR (300 MHz, DMSO-d₆): δ 7.40-7.34 (m, 3H), 7.31 (d, J=3.3 Hz, 1H), 7.28-7.20 (m, 5H), 7.10 (dt, J₁=1.5 Hz, J₂=7.5 Hz, 1H), 6.94 (d, J=8.7 Hz, 1H), 6.71 (d, J=1.8 Hz, 1H), 6.56 (dd, J₁=8.7 Hz, J₂=2.1 Hz, 1H), 6.39 (d, J=2.7 Hz, 1H), 5.11 (s, 2H), 4.93 (s, 1H), 3.76 (t, J=6.3 Hz, 2H), 3.16 (q, J=6.0 Hz, 2H), 0.88 (s, 9H), 0.02 (s, 6H). ESI-MS m/z=473 (M+H)⁺.

N-(1-(2-(Benzyloxy) phenyl)-1H-indol-5-yl)-N-(2-(tert-butyldimethylsilyloxy)ethyl)-4,6-dichloropyrimidine-5-carboxamide (16D)

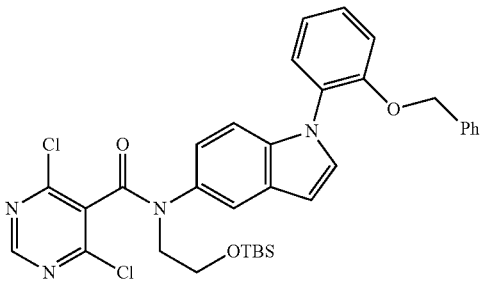 [SMILES: CC(C)(C)[Si](C)(C)OCCN(C(=O)c1c(Cl)ncnc1Cl)c1ccc2c(ccn2-c2ccccc2OCc2ccccc2)c1]

A solution of 4, 6-dichloropyrimidine-5-carbonyl chloride (1.39 g, 6.60 mmol) in DCM (5 mL) was added dropwise to an ice-cold solution of Example 16C (2.6 g, 5.50 mmol) and triethylamine (3.83 mL, 27.5 mmol) in DCM (30 mL), and the mixture was stirred for 1 h. This was then concentrated in vacuo, diluted into ethyl acetate and washed with water (2×20 mL). The separated organic layer was dried over sodium sulphate and filtered. The filtrate was concentrated in vacuo and purified by flash chromatography using 20% ethyl acetate in hexane to afford the title compound (2.8 g, 79%) as a yellow liquid. $^1$H NMR (300 MHz, DMSO-$d_6$): δ 8.70 (s, 1H), 7.71 (d, J=1.8 Hz, 1H), 7.52 (d, J=3.3 Hz, 1H), 7.44 (m, 1H), 7.36 (dd, $J_1$=7.5 Hz, $J_2$=1.2 Hz, 2H), 7.24-7.21 (m, 3H), 7.19-7.07 (m, 4H), 7.03 (d, J=9.0 Hz, 1H), 6.60 (d, J=3.3 Hz, 1H), 5.08 (s, 2H), 3.98 (t, J=5.7 Hz, 2H), 3.78 (t, J=5.7 Hz, 2H), 0.85 (s, 9H), 0.02 (s, 6H). ESI-MS m/z=647 (M+H)$^+$.

N-(1-(2-(Benzyloxy)phenyl)-1H-indol-5-yl)-4,6-dichloro-N-(2-hydroxyethyl)pyrimidine-5-carboxamide (16E)

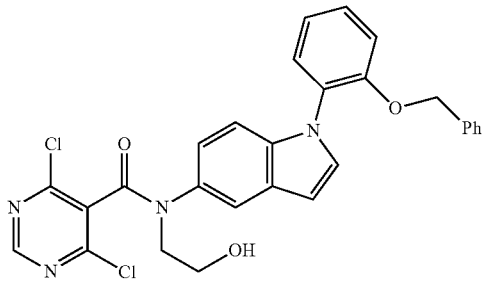 [SMILES: O=C(c1c(Cl)ncnc1Cl)N(CCO)c1ccc2c(ccn2-c2ccccc2OCc2ccccc2)c1]

A solution of Example 16D (2.8 g, 4.32 mmol) in 15 mL of methanolic solution of HCl (3N) was stirred at room temperature for 1 h. Methanol was removed in vacuo, the residue was dissolved in ethyl acetate, and washed with saturated aqueous sodium bicarbonate and saturated aqueous brine. The separated organic layer was dried over sodium sulfate and filtered, and the filtrate was concentrated in vacuo to afford the title compound (2.1 g, 91%) as an off-white solid, which was carried on to the next step without further purification. $^1$H NMR (300 MHz, DMSO-$d_6$): δ 8.70 (s, 1H), 7.71 (d, J=2.1 Hz, 1H), 7.52 (d, J=3.3 Hz, 1H), 7.42 (dd, $J_1$=7.5 Hz, $J_2$=1.5 Hz, 1H), 7.38 (s, 1H) 7.36 (d, J=1.5 Hz, 1H), 7.28-7.22 (m, 3H), 7.19-7.03 (m, 5H), 6.63 (d, J=3.3 Hz, 1H), 5.09 (s, 2H), 4.84 (s, 1H), 3.93 (t, J=6.0 Hz, 2H), 3.61 (q, J=4.8 Hz, 2H). ESI-MS m/z=533 (M+H)$^+$.

6-(1-(2-(Benzyloxy)phenyl)-1H-indol-5-yl)-4-chloro-7,8-dihydropyrimido[5,4-f][1,4]oxazepin-5(6H)-one (16F)

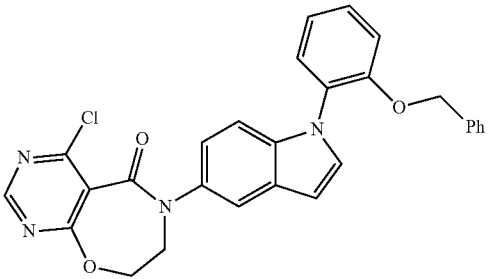 [SMILES: O=C1c2c(Cl)ncnc2OCCN1c1ccc2c(ccn2-c2ccccc2OCc2ccccc2)c1]

A solution of Example 16E (2.1 g, 3.94 mmol) and triethylamine (4.39 mL, 31.5 mmol) in acetonitrile (20 mL) was stirred at 80° C. for 8 h. The reaction mixture was cooled and concentrated in vacuo, and the residue was partitioned between ethyl acetate and water. Separated organic layer was dried over sodium sulfate and filtered, and the filtrate was concentrated in vacuo to afford the title compound (1.7 g, 87%) as an off-white solid. $^1$H NMR (300 MHz, DMSO-$d_6$): δ 8.83 (s, 1H), 7.67 (d, J=1.8 Hz, 1H), 7.58 (d, J=3.0 Hz, 1H), 7.46 (d, J=7.2 Hz, 2H), 7.39 (m, 1H), 7.31-7.13 (m, 8H), 6.70 (d, J=3.3 Hz, 1H), 5.15 (s, 2H), 4.76 (t, J=5.4 Hz, 2H), 4.16 (t, J=4.8 Hz, 2H). ESI-MS m/z=497 (M+H)$^+$.

4-Amino-6-(1-(2-(benzyloxy)phenyl)-1H-indol-5-yl)-7,8-dihydropyrimido[5,4-f][1,4]oxazepin-5(6H)-one (16G)

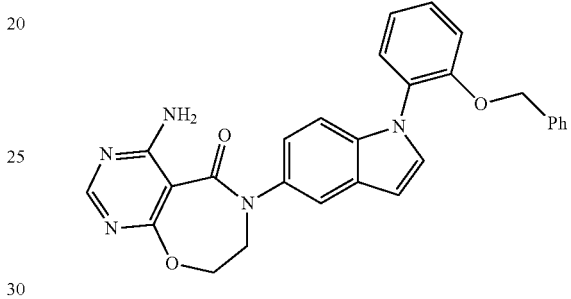

A solution of Example 16F (1.7 g, 3.19 mmol) in 0.5 M ammonia in 1,4-dioxane (20 mL) was stirred at room temperature for 2 h. The reaction mixture was concentrated in vacuo, and the residue was partitioned between ethyl acetate and water. Separated organic layer was dried over sodium sulfate and filtered, and the filtrate was concentrated in vacuo to afford the title compound (1.3 g, 85%) as an off-white solid. $^1$H NMR (400 MHz, DMSO-$d_6$): δ 8.15 (s, 1H), 7.59 (bs, 2H), 7.56 (d, J=1.6 Hz, 1H), 7.52 (d, J=3.2 Hz, 1H), 7.42 (d, J=7.6 Hz, 2H), 7.35 (d, J=8.4 Hz, 1H), 7.26-7.18 (m, 5H), 7.15-7.05 (m, 3H), 6.63 (d, J=2.8 Hz, 1H), 5.11 (s, 2H), 4.61 (t, J=4.4 Hz, 2H), 3.96 (t, J=4.4 Hz, 2H). ESI-MS m/z=478 (M+H)$^+$.

4-Amino-6-(1-(2-hydroxyphenyl)-1H-indol-5-yl)-7,8-dihydropyrimido[5,4-f][1,4]oxazepin-5(6H)-one (16)

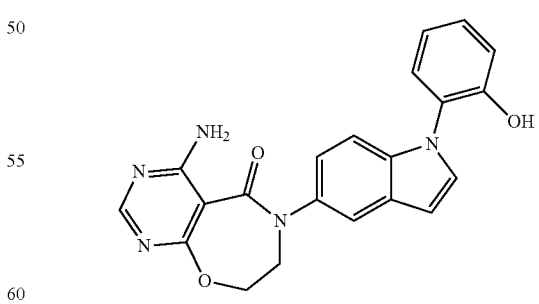

Ammonium formate (0.858 g, 13.6 mmol) and Pd/C (0.2 g, 1.879 mmol) were added to a solution of Example 16G (1.3 g, 2.72 mmol) in methanol (20 mL) and stirred at 80° C. for 3 h. The reaction mixture was allowed to warm to room temperature, filtered through a pad of celite, and the filtrate was concentrated in vacuo. The residue was diluted into ethyl acetate, washed with water, dried over sodium sulfate and filtered. The filtrate was concentrated in vacuo to afford the title compound (0.9 g, 85% yield) as an off-white solid. $^1$H NMR (300 MHz, DMSO-$d_6$): δ 9.98 (s, 1H), 8.18 (s, 1H), 7.62 (bs, 2H), 7.58 (d, J=1.2 Hz, 1H), 7.49 (d, J=3.0 Hz, 1H), 7.30 (t, J=7.5 Hz, 2H), 7.15-7.06 (m, 3H), 6.97 (t, J=7.2 Hz, 1H), 6.64 (d, J=3.3 Hz, 1H), 4.64 (t, J=4.5 Hz, 2H), 4.00 (t, J=4.5 Hz, 2H). ESI-MS m/z=388 (M+H)$^+$.

4-Amino-6-(1-(2-(cyclopentyloxy)phenyl)-1H-indol-5-yl)-7,8-dihydropyrimido[5,4-f][1,4]oxazepin-5(6H)-one (17)

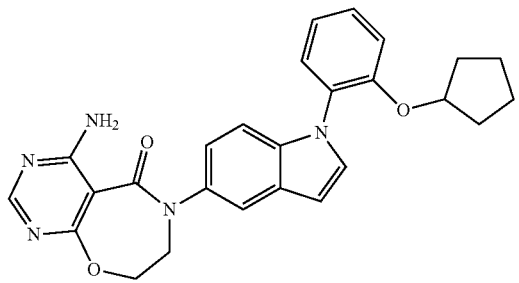 [SMILES: Nc1ncnc2c1C(=O)N(c1ccc3c(ccn3-c3ccccc3OC3CCCC3)c1)CCO2]

Cesium carbonate (0.5 g, 1.549 mmol) was added to a solution of Example 16 (0.2 g, 0.516 mmol) and bromocyclopentane (0.092 g, 0.620 mmol) in DMF (8 mL), and the mixture was stirred at room temperature for 12 h. The reaction mixture was diluted into ethyl acetate, washed with water, dried over sodium sulfate and filtered. The filtrate was concentrated in vacuo to afford the title compound (0.18 g, 73%) as off-white solid. $^1$H NMR (300 MHz, DMSO-$d_6$): δ 8.18 (s, 1H), 7.62 (bs, 2H), 7.58 (s, 1H), 7.47 (d, J=2.7 Hz, 1H), 7.43-7.39 (m, 2H), 7.27 (d, J=8.1 Hz, 1H), 7.16-7.10 (m, 3H), 6.65 (d, J=3.0 Hz, 1H), 4.84 (m, 1H), 4.64 (t, J=5.1 Hz, 2H), 4.0 (t, J=4.8 Hz, 2H), 1.78 (m, 2H), 1.57 (m, 2H), 1.50-1.40 (m, 4H). ESI-MS m/z=456 (M+H)$^+$; HPLC purity: 95.8%.

Examples 18-20 were prepared using procedures analogous to those described in Examples 16-17 with appropriate starting materials.

| Exp | Structure | Analytical Data | Mass/Purity |
|---|---|---|---|
| 18 | 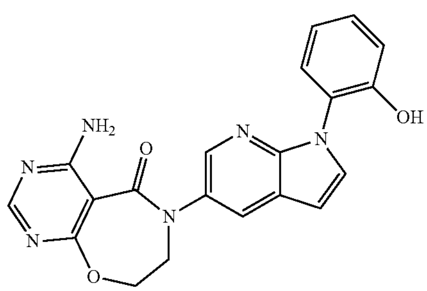 [SMILES: Nc1ncnc2c1C(=O)N(c1cnc3c(ccn3-c3ccccc3O)c1)CCO2] | $^1$H NMR (300 MHz, DMSO-$d_6$): δ 9.90 (s, 1H), 8.19 (d, J = 1.8 Hz, 2H), 8.05 (d, J = 2.1 Hz, 1H), 7.70-7.60 (m, 3H), 7.40 (dd, $J_1$ = 1.5 Hz, $J_2$ = 8.1 Hz, 1H), 7.23 (m, 1H), 7.07 (dd, $J_1$ = 1.2 Hz, $J_2$ = 8.1 Hz, 1H), 6.95 (dt, $J_1$ = 1.2 Hz, $J_2$= 7.2 Hz, 1H), 6.66 (d, J = 3.6 Hz, 1H), 4.68 (t, J = 4.8 Hz, 2H), 4.05 (t, J = 4.5 Hz, 2H). | ESI-MS m/z = 389 (M + H)$^+$; LCMS purity: 92.3%. |
| 19 | 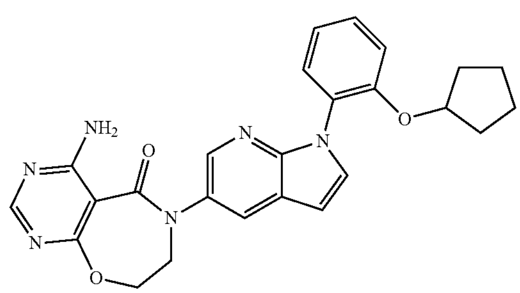 [SMILES: Nc1ncnc2c1C(=O)N(c1cnc3c(ccn3-c3ccccc3OC3CCCC3)c1)CCO2] | $^1$H NMR (400 MHz, DMSO-$d_6$): δ 8.18 (s, 2H), 8.04 (s, 1H), 7.64 (m, 3H), 7.50 (d, J = 6.8 Hz, 1H), 7.41 (d, J = 7.2 Hz, 1H), 7.24 (d, J = 7.6 Hz, 1H), 7.09 (t, J = 7.2 Hz, 1H), 6.66 (s, 1H), 4.84 (m, 1H), 4.67 (m, 2H), 4.03 (m, 2H), 1.76 (m, 2H), 1.59 (m, 2H), 1.43 (m, 4H). | ESI-MS m/z = 457 (M + H)$^+$; HPLC purity: 93%. |
| 20 | 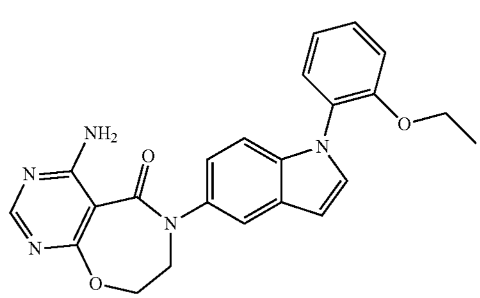 [SMILES: CCOc1ccccc1-n1ccc2cc(N3CCOc4ncnc(N)c4C3=O)ccc21] | $^1$H NMR (400 MHz, DMSO-$d_6$): δ 8.18 (s, 1H), 7.62 (bs, 2H), 7.59 (d, J = 2.0 Hz, 1H), 7.51 (d, J = 2.8 Hz, 1H), 7.46-7.38 (m, 2H), 7.29 (d, J = 7.6 Hz, 1H), 7.15-7.07 (m, 3H), 6.66 (d, J = 2.8 Hz, 1H), 4.64 (t, J = 4.8 Hz, 2H), 4.08 (q, J = 6.8 Hz, 2H), 4.0 (t, J = 4.4 Hz, 2H), 1.17 (t, J = 7.2 Hz, 3H). | ESI-MS m/z = 416 (M + H)$^+$; HPLC purity: 94.3%. |

Example 21

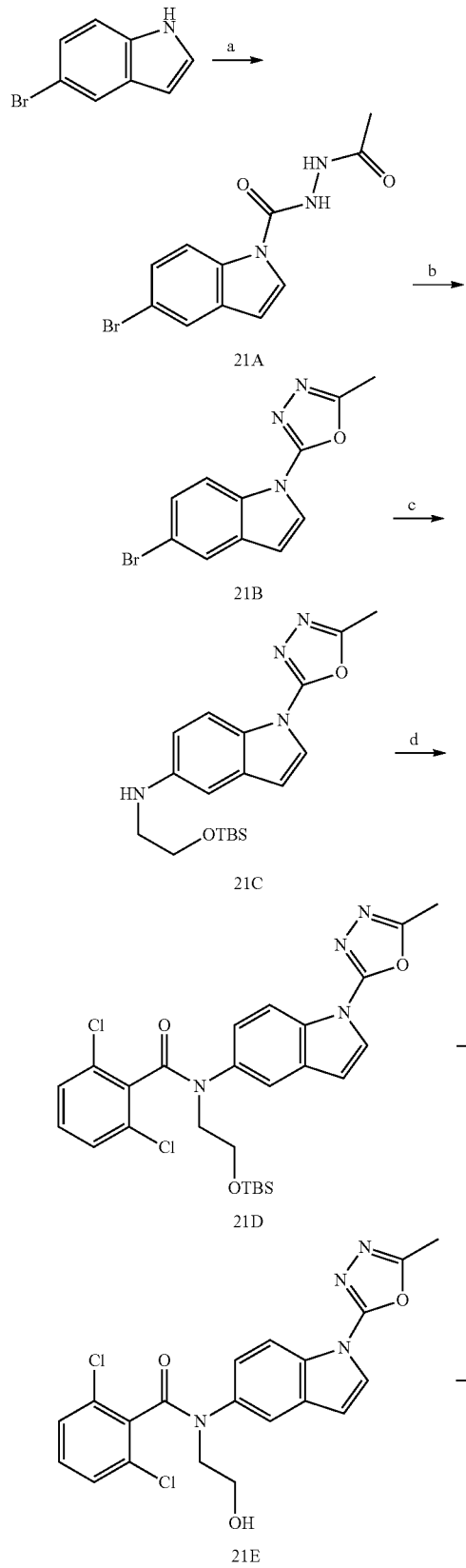

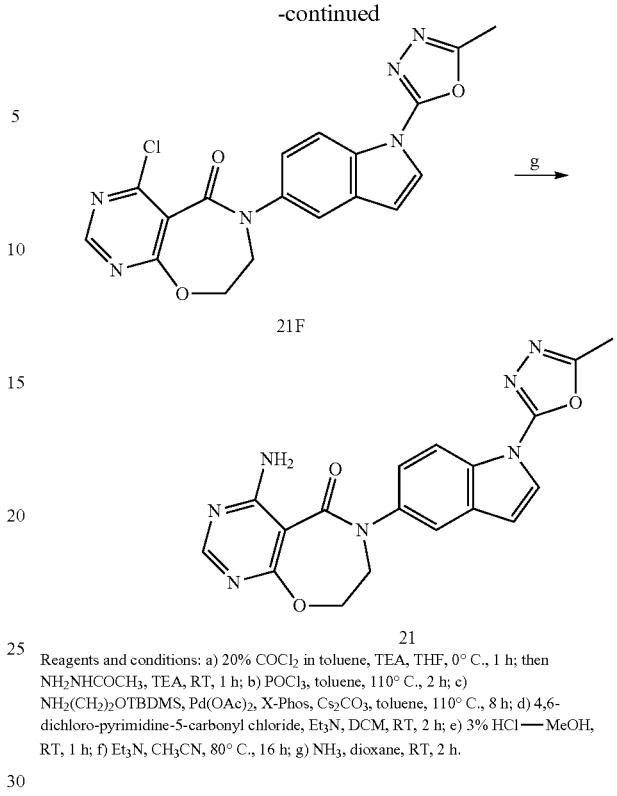

Reagents and conditions: a) 20% COCl₂ in toluene, TEA, THF, 0° C., 1 h; then NH₂NHCOCH₃, TEA, RT, 1 h; b) POCl₃, toluene, 110° C., 2 h; c) NH₂(CH₂)₂OTBDMS, Pd(OAc)₂, X-Phos, Cs₂CO₃, toluene, 110° C., 8 h; d) 4,6-dichloro-pyrimidine-5-carbonyl chloride, Et₃N, DCM, RT, 2 h; e) 3% HCl—MeOH, RT, 1 h; f) Et₃N, CH₃CN, 80° C., 16 h; g) NH₃, dioxane, RT, 2 h.

Procedures

4-Amino-6-(1-(5-methyl-1,3,4-oxadiazol-2-yl)-1H-indol-5-yl)-7,8-dihydropyrimido[5,4-f][1,4]oxazepin-5(6H)-one N'-Acetyl-5-bromo-1H-indole-1-carbohydrazide (21A)

Triethyl amine (8.89 mL, 63.8 mmol) and phosgene (20% in toluene) (18.92 g, 38.3 mmol) were added to an ice-cold solution of 5-bromo-1H-indole (5 g, 25.5 mmol) in THF (50 mL), and the mixture was stirred for 20 min. Acetohydrazide (2.267 g, 30.6 mmol) in THF (10 mL) was then added, and stirring was continued for 1 h at room temperature. The reaction mixture was then diluted with water and extracted with ethyl acetate. Separated organic layer was dried over sodium sulphate and filtered, and the filtrate was concentrated in vacuo to afford the title compound (3.8 g, 49%) as an off-white solid. ¹H NMR (400 MHz, DMSO-d₆): δ 10.15 (s, 1H), 10.01 (s, 1H), 8.14 (d, J=9.2 Hz, 1H), 7.90 (d, J=4.0

Hz, 1H), 7.85 (d, J=2.0 Hz, 1H), 7.43 (dd, J₁=8.8 Hz, J₂=2.0 Hz, 1H), 6.74 (d, J=3.6 Hz, 1H), 1.95 (s, 3H). ESI-MS m/z=296 (M−H)⁺.

2-(5-Bromo-1H-indol-1-yl)-5-methyl-1,3,4-oxadiazole (21B)

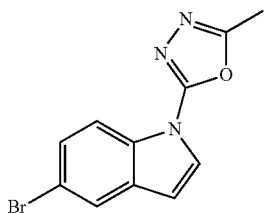 [SMILES: Cc1nnc(-n2ccc3cc(Br)ccc32)o1]

POCl₃ (0.944 mL, 10.13 mmol) was added to a solution of Example 21A (3.0 g, 10.13 mmol) in toluene (30 mL), and the mixture was stirred at 110° C. for 2 h. The reaction mixture was then warmed to room temperature, poured into ice-cold water and extracted into ethyl acetate. Separated organic layer was dried over sodium sulphate and filtered, and the filtrate was concentrated in vacuo to afford the title compound (2.1 g, 73%) as an off-white solid. ¹H NMR (400 MHz, DMSO-d₆): δ 8.13 (d, J=8.8 Hz, 1H), 7.95 (d, J=2.0 Hz, 1H), 7.88 (d, J=4.0 Hz, 1H), 7.56 (dd, J₁=8.4 Hz, J₂=1.6 Hz, 1H), 6.89 (d, J=3.2 Hz, 1H), 2.59 (s, 3H). ESI-MS m/z=278 (M+H)⁺.

N-(2-(tert-Butyldimethylsilyloxy)ethyl)-1-(5-methyl-1,3,4-oxadiazol-2-yl)-1H-indol-5-amine (21C)

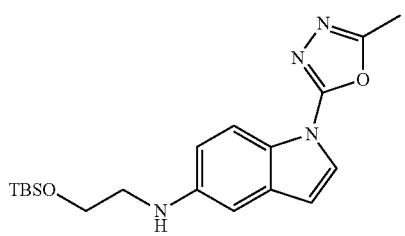 [SMILES: Cc1nnc(-n2ccc3cc(NCCO[Si](C)(C)C(C)(C)C)ccc32)o1]

A mixture of Example 21B (2.1 g, 7.55 mmol), 2-(tert-butyldimethylsilyloxy) ethanamine (1.98 g, 11.33 mmol) and cesium carbonate (4.91 g, 15.1 mmol) in toluene (30 mL) was degassed for 15 min under argon. Palladium acetate (0.339 g, 1.51 mmol) and X-Phos (0.719 g, 1.51 mmol) were then added and the reaction mixture was stirred at 120° C. for 16 h. The reaction mixture was cooled and partitioned between ethyl acetate and water. Separated organic layer was dried over sodium sulphate and filtered, and the filtrate was concentrated in vacuo. The residue was purified by flash chromatography using 30% dichloromethane in hexanes to afford the title compound (1 g, 29%) as an off-white solid. ¹H NMR (300 MHz, DMSO-d₆): δ 7.87 (d, J=9.0 Hz, 1H), 7.62 (d, J=3.6 Hz, 1H), 6.78-6.75 (m, 2H), 6.66 (d, J=3.3 Hz, 1H), 5.39 (t, J=5.4 Hz, 1H), 3.75 (t, J=6.3 Hz, 2H), 3.18 (q, J=6.0 Hz, 2H), 2.54 (s, 3H), 0.87 (s, 9H), 0.03 (s, 6H). ESI-MS m/z=373 (M+H)⁺.

N-(2-(tert-Butyldimethylsilyloxy)ethyl)-4,6-dichloro-N-(1-(5-methyl-1,3,4-oxadiazol-2-yl)-1H-indol-5-yl)pyrimidine-5-carboxamide (21D)

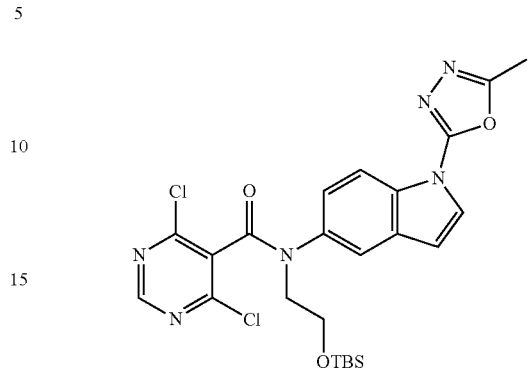

A solution of 4,6-dichloropyrimidine-5-carbonyl chloride (0.675 g, 3.21 mmol) in DCM (10 mL) was added dropwise to an ice-cold solution of Example 21C (1.0 g, 2.68 mmol) and triethylamine (0.374 mL, 4.02 mmol) in DCM (20 mL) and stirred for 1 h. The reaction mixture was concentrated in vacuo, diluted with ethyl acetate, washed with water (2×10 mL). Separated organic layer was dried over sodium sulphate and filtered, and the filtrate was concentrated in vacuo. The residue was purified by flash chromatography using 15% ethyl acetate in hexanes to afford the title compound (0.95 g, 53%) as a pale yellow solid. ¹H NMR (300 MHz, DMSO-d₆): δ 8.74 (s, 1H), 8.07 (d, J=8.7 Hz, 1H), 7.84 (d, J=3.9 Hz, 1H), 7.80 (s, 1H), 7.45 (d, J=8.7 Hz, 1H), 6.86 (d, J=3.6 Hz, 1H), 4.03 (t, J=4.5 Hz, 2H), 3.80 (t, J=5.1 Hz, 2H), 2.55 (s, 3H), 0.85 (s, 9H), 0.02 (s, 6H). ESI-MS m/z=547 (M+H)⁺.

4,6-Dichloro-N-(2-hydroxyethyl)-N-(1-(5-methyl-1,3,4-oxadiazol-2-yl)-1H-indol-5-yl)pyrimidine-5-carboxamide (21E)

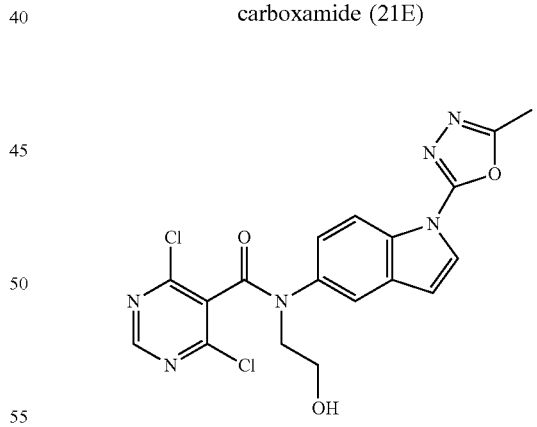

A solution of Example 21D (0.95 g, 1.735 mmol) in 20 mL of methanolic solution of HCl (3% HCl in MeOH) was stirred at room temperature for 1 h. Methanol was removed in vacuo, and the residue was dissolved in ethyl acetate, washed with saturated aqueous sodium bicarbonate and saturated aqueous brine. The separated organic layer was dried over sodium sulfate and filtered, and the filtrate was concentrated in vacuo to afford the title compound (0.5 g, 43%) as a pale yellow solid, which was carried on to the next step without further purification. ¹H NMR (300 MHz, DMSO-d₆): δ 8.73 (s, 1H), 8.08 (d, J=8.7 Hz, 1H), 7.84 (d, J=3.6 Hz, 1H), 7.83 (d, J=1.8 Hz, 1H), 7.46 (dd, J₁=9.0 Hz, J₂=1.8 Hz, 1H), 6.90 (d, J=3.3 Hz, 1H), 4.87 (bs, 1H), 3.96 (t, J=6.3 Hz, 2H), 3.63 (q, J=5.1 Hz, 2H), 2.55 (s, 3H). ESI-MS m/z=433 (M+H)⁺.

4-Chloro-6-(1-(5-methyl-1,3,4-oxadiazol-2-yl)-1H-indol-5-yl)-7,8-dihydropyrimido[5,4-f][1,4]oxazepin-5(6H)-one (21F)

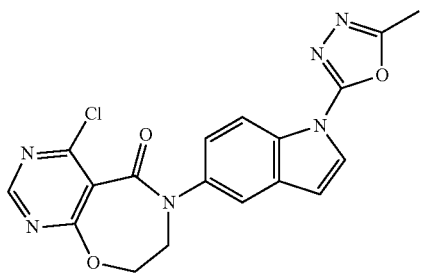 [SMILES: Cc1nnc(-n2ccc3cc(N4CCOc5ncnc(Cl)c5C4=O)ccc32)o1]

A solution of Example 21E (0.5 g, 1.154 mmol) and TEA (0.8 mL, 5.77 mmol) in acetonitrile (20 mL) was stirred at 80° C. for 16 h. The reaction mixture was cooled and concentrated in vacuo, and the residue was partitioned between ethyl acetate and water. Separated organic layer was dried over sodium sulfate and filtered, and the filtrate was concentrated in vacuo to afford the title compound (0.3 g, 65%) as a pale yellow solid that was carried on to the next step without further purification.

4-Amino-6-(1-(5-methyl-1,3,4-oxadiazol-2-yl)-1H-indol-5-yl)-7,8-dihydropyrimido[5,4-f][1,4]oxazepin-5(6H)-one (21)

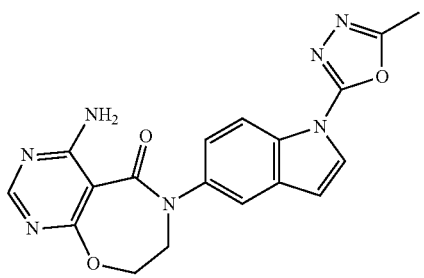 [SMILES: Cc1nnc(-n2ccc3cc(N4CCOc5ncnc(N)c5C4=O)ccc32)o1]

A solution of Example 21F (0.3 g, 0.756 mmol) in 0.5 M ammonia in 1, 4-dioxane (15 mL) was stirred at room temperature for 3 h. The reaction mixture was concentrated in vacuo, and the residue was partitioned between ethyl acetate and water. Separated organic layer was dried over sodium sulfate and filtered, and the filtrate was concentrated in vacuo to give a solid mass. This solid material was triturated with diethyl ether to afford the title compound (0.12 g, 40%) as a white solid. ¹H NMR (400 MHz, DMSO-d₆): δ 8.21 (d, J=8.8 Hz, 1H), 8.18 (s, 1H), 7.89 (d, J=3.2 Hz, 1H), 7.73 (d, J=2.0 Hz, 1H), 7.64 (bs, 2H), 7.41 (dd, J₁=8.8 Hz, J₂=2.0 Hz, 1H), 6.93 (d, J=3.2 Hz, 1H), 4.66 (t, J=4.0 Hz, 2H), 4.04 (t, J=4.8 Hz, 2H), 2.58 (s, 3H). ESI-MS m/z=378 (M+H)⁺; LCMS purity: 95%; HPLC purity: 94%.

Example 22

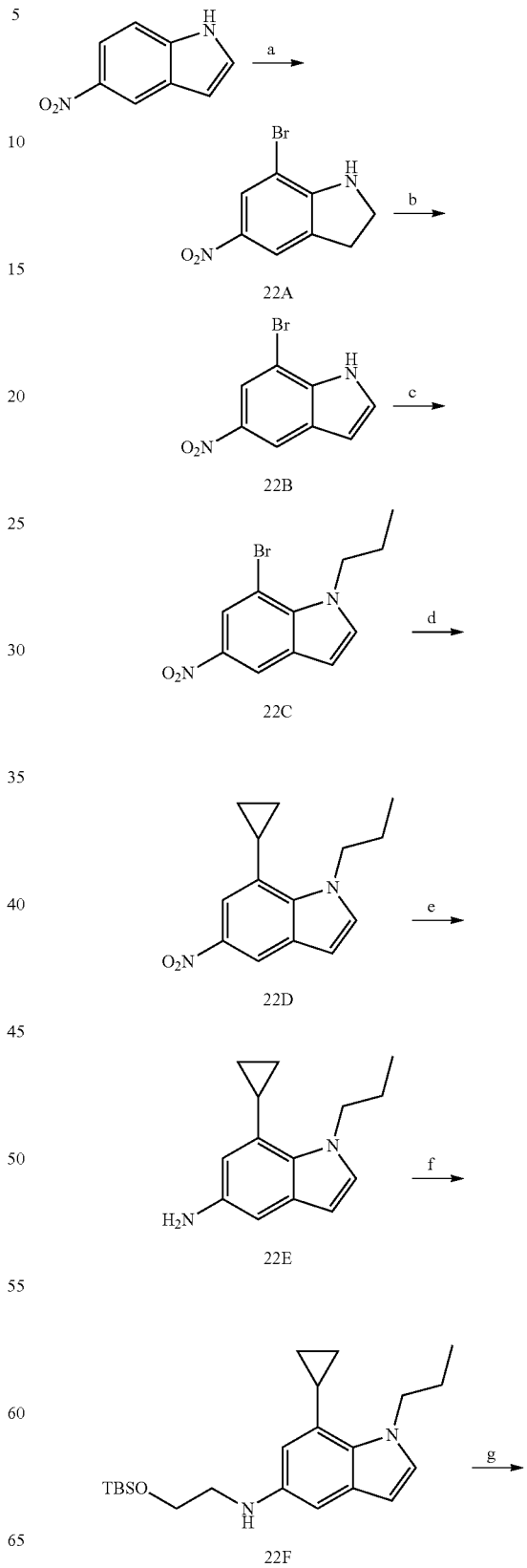

59
-continued

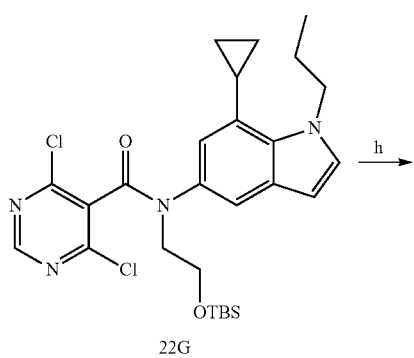
22G

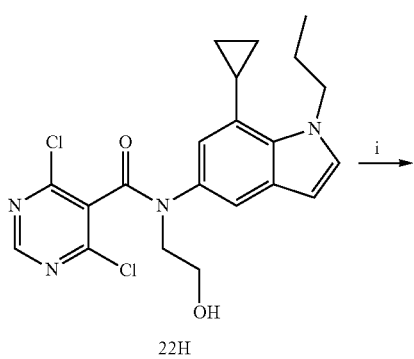
22H

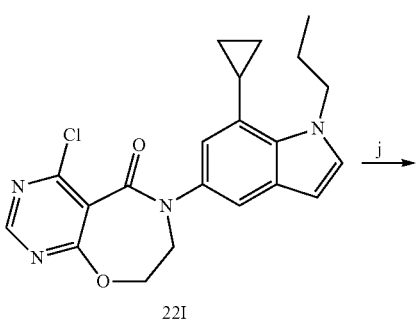
22I

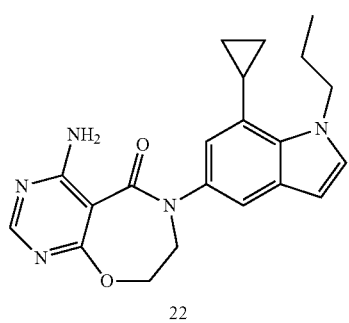
22

Reagents and conditions: a) Br₂, AcOH, 0° C., 1 h; b) DDQ, EtOH, IPA, 80° C., 2 h; c) 1-bromopropane, Cs₂CO₃, DMF, 70° C., 1 h; d) Cyclopropyl boronic acid, Cs₂CO₃, PdCl₂(dppf), Toluene- H₂O, 100° C., 2 h; e) Pd/C, EtOH, H₂, RT, 16 h; f) TBDMSO(CH₂)₂Br, K₂CO₃, CH₃CN, 80° C., 24 h; g) 4,6-dichloropyrimidine-5-carbonyl chloride, Et₃N, DCM, RT, 1 h; h) 3% HCl—MeOH, RT, 1 h; i) Et₃N, CH₃CN, 80° C., 16 h; j) NH₃, dioxane, RT, 3 h.

60
Procedures

4-Amino-6-(7-cyclopropyl-1-propyl-1H-indol-5-yl)-7,8-dihydropyrimido[5,4-f][1,4]oxazepin-5(6H)-one 7-Bromo-5-nitroindoline (22A)

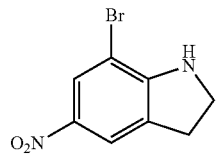

Bromine (1.569 mL, 30.5 mmol) was added dropwise to an ice-cold solution of 5-nitro indoline (5 g, 30.5 mmol) in acetic acid (50 mL), and the mixture was stirred for 1 h. Acetic acid was concentrated under reduced pressure, and the resulting solid was triturated with water to afford the title compound (6 g, 80%) as a yellow solid, which was carried on to the next step without further purification. ¹H NMR (300 MHz, DMSO-d₆): δ 8.07 (d, J=2.1 Hz, 1H), 7.84 (d, J=2.1 Hz, 1H), 7.3 (bs, 1H), 3.7 (t, J=8.7 Hz, 2H), 3.17 (t, J=8.4 Hz, 2H). ESI-MS m/z=243 (M+H)⁺.

7-Bromo-5-nitro-1H-indole (22B)

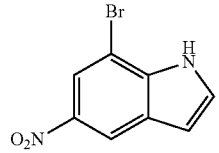

DDQ (5.6 g, 24.69 mmol) and isopropanol (2 mL) were added to a solution of Example 22A (3 g, 12.34 mmol) in ethanol (30 mL), and the mixture was stirred at 80° C. for 48 h. The reaction mixture was concentrated under reduced pressure, and the residue was partitioned between ethyl acetate and water. Separated organic layer was washed with water, dried over sodium sulphate, filtered and the filtrate was concentrated in vacuo. The crude product was purified by flash chromatography using 20% ethyl acetate in hexane to afford the title compound (2.5 g, 84%) as a yellow solid. ¹H NMR (300 MHz, DMSO-d₆): δ 12.13 (bs, 1H), 8.62 (d, J=1.8 Hz, 1H), 8.18 (d, J=1.8 Hz, 1H), 7.67 (t, J=3.0 Hz, 1H), 6.89 (m, 1H). ESI-MS m/z=241 (M+H)⁺.

7-Bromo-5-nitro-1-propyl-1H-indole (22C)

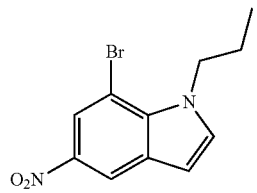 [SMILES: CCCn1ccc2cc([N+](=O)[O-])cc(Br)c21]

1-Bromopropane (1.53 g, 12.45 mmol) and cesium carbonate (10.14 g, 31.1 mmol) were added to a solution of Example 22B (2.5 g, 10.37 mmol) in DMF (5 mL), and the mixture was stirred at 70° C. for 1 h. DMF was removed under reduced pressure, and the residue was partitioned between ethyl acetate and water. Separated organic layer was washed with water, dried over sodium sulphate and filtered, and the filtrate was concentrated in vacuo. The crude product was purified by flash chromatography using 10% ethyl acetate in hexane to afford the title compound (2 g, 64%) as a yellow solid. $^1$H NMR (400 MHz, DMSO-$d_6$): δ 8.56 (d, J=2.0 Hz, 1H), 8.12 (d, J=2.4 Hz, 1H), 7.69 (d, J=3.2 Hz, 1H), 6.81 (d, J=2.8 Hz, 1H), 4.5 (t, J=7.6 Hz, 2H), 1.77 (m, 2H), 0.83 (t, J=7.6 Hz, 3H). ESI-MS m/z=283 (M+H)$^+$.

7-Cyclopropyl-5-nitro-1-propyl-1H-indole (22D)

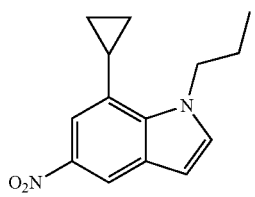

PdCl$_2$(dppf)-CH$_2$Cl$_2$ adduct (0.517 g, 0.706 mmol) was added to a solution of 22C (2 g, 7.06 mmol) in 15 mL of toluene kept under argon, followed by addition of cesium carbonate (6.90 g, 21.19 mmol) and cyclopropyl boronic acid (0.728 g, 8.48 mmol). The mixture was then degassed for 5 min and stirred at 100° C. for 2 h. The reaction mixture was warmed to room temperature and partitioned between ethyl acetate and water. Separated organic layer was washed with water, dried over sodium sulphate and filtered, and the filtrate was concentrated in vacuo. The crude product was purified by flash chromatography using 10% ethyl acetate in hexane to afford the title compound (1.8 g, 69%) as yellow solid. $^1$H NMR (400 MHz, DMSO-$d_6$): δ 8.41 (d, J=2.4 Hz, 1H), 7.68 (d, J=1.2 Hz, 1H), 7.62 (d, J=3.6 Hz, 1H), 6.76 (d, J=3.6 Hz, 1H), 4.6 (t, J=7.2 Hz, 2H), 2.45 (m, 1H), 1.85-1.76 (m, 2H), 1.16-1.02 (m, 2H), 0.93-0.85 (m, 5H). ESI-MS m/z=245.2 (M+H)$^+$.

7-Cyclopropyl-1-propyl-1H-indol-5-amine (22E)

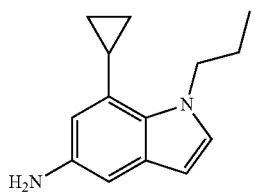 [SMILES: CCCn1ccc2cc([N+](=O)[O-])cc(C3CC3)c21]

Palladium on carbon (0.157 g, 1.474 mmol) was added to a solution of Example 22D (1.8 g, 7.37 mmol) in ethanol (20 mL), and the mixture was stirred under hydrogen atmosphere for 16 h at room temperature. The reaction mixture was then filtered through a pad of celite, and the filtrate was concentrated under reduced pressure. The crude residue was purified by flash chromatography using 25% ethyl acetate in hexane to afford the title compound (1 g, 57%) as an off-white solid. $^1$H NMR (400 MHz, DMSO-$d_6$): δ 7.08 (d, J=2.4 Hz, 1H), 6.49 (d, J=1.6 Hz, 1H), 6.26 (d, J=1.6 Hz, 1H), 6.08 (d, J=2.8 Hz, 1H), 4.42-4.28 (m, 4H), 2.22 (m, 1H), 1.76-1.62 (m, 2H), 0.94-0.88 (m, 2H), 0.84 (t, J=7.2 Hz, 3H), 0.70 (q, J=5.6 Hz, 2H). ESI-MS m/z=215 (M+H)$^+$.

N-(2-((tert-Butyldimethylsilyl)oxy)ethyl)-7-cyclopropyl-1-propyl-1H-indol-5-amine (22F)

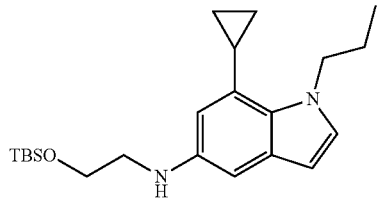 [SMILES: CCCn1ccc2cc(NCCO[Si](C)(C)C(C)(C)C)cc(C3CC3)c21]

(2-Bromoethoxy) (tert-butyl) dimethylsilane (1.116 g, 4.67 mmol) and potassium carbonate (2.58 g, 18.66 mmol) were added to a solution of Example 22E (1 g, 4.67 mmol) in acetonitrile (10 mL), and the mixture was stirred at 80° C. for 24 h. Acetonitrile was removed under vacuum, and the residue was partitioned between ethyl acetate and water. Separated organic layer was dried over sodium sulphate and filtered, and the filtrate was concentrated in vacuo. The crude product was purified by flash column chromatography using 5% ethyl acetate in hexane to afford the title compound (0.6 g, 34%) as a colorless syrup. $^1$H NMR (300 MHz, DMSO-$d_6$): δ 7.10 (d, J=3.0 Hz, 1H), 6.46 (d, J=1.8 Hz, 1H), 6.29 (d, J=1.8 Hz, 1H), 6.14 (d, J=3.0 Hz, 1H), 4.73 (t, J=5.7 Hz, 1H), 4.38 (t, J=7.2 Hz, 2H), 3.71 (t, J=6.3 Hz, 2H), 3.09 (q, J=6.3 Hz, 2H), 2.26-2.22 (m, 1H), 1.76-1.68 (m, 2H), 0.98-0.82 (m, 14H), 0.75-0.68 (m, 2H), 0.04 (s, 6H). ESI-MS m/z=373 (M+H)$^+$.

N-(2-((tert-Butyldimethylsilyl)oxy)ethyl)-4,6-dichloro-N-(7-cyclopropyl-1-propyl-1H-indol-5-yl)pyrimidine-5-carboxamide (22G)

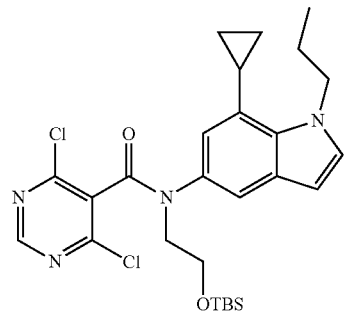 [SMILES: CCCn1ccc2cc(N(CCO[Si](C)(C)C(C)(C)C)C(=O)c3c(Cl)ncnc3Cl)cc(C3CC3)c21]

A solution of 4,6-dichloropyrimidine-5-carbonyl chloride (0.849 g, 4.5 mmol) in DCM (10 mL) was added dropwise to an ice-cold solution of Example 22F (0.47 g, 2.415 mmol) and triethylamine (1.87 mL, 13.4 mmol) in DCM (30 mL), and the mixture was stirred for 1 h. The reaction was diluted with dichloromethane and washed with water. Separated organic layer was dried over sodium sulphate and filtered, and the filtrate was concentrated in vacuo. The residue was purified by flash chromatography using 20% ethyl acetate in hexanes to afford the title compound (0.5 g, 57%) as an off-white solid. $^1$H NMR (300 MHz, DMSO-$d_6$): δ 8.7 (s, 1H), 7.48 (d, J=1.8 Hz, 1H), 7.35 (d, J=3.3 Hz, 1H), 6.8 (d, J=1.8 Hz, 1H), 6.38 (d, J=3.3 Hz, 1H), 4.42 (t, J=7.5 Hz, 2H), 3.96 (t, J=2.1 Hz, 2H), 3.76 (t, J=5.4 Hz, 2H), 2.31-2.22 (m, 1H), 1.71 (q, J=7.8 Hz, 2H), 0.98-0.72 (m, 2H), 0.88-0.78 (m, 12H), 0.62-0.56 (m, 2H), 0.023 (s, 6H). ESI-MS m/z=547 (M+H)+.

4,6-Dichloro-N-(7-cyclopropyl-1-propyl-1H-indol-5-yl)-N-(2-hydroxyethyl)pyrimidine-5-carboxamide (22H)

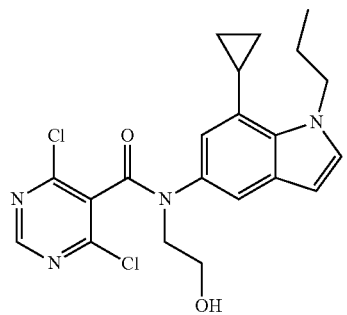 [SMILES: CCCn1ccc2cc(N(CCO)C(=O)c3c(Cl)ncnc3Cl)cc(C3CC3)c21]

A solution of Example 22G (0.5 g, 0.913 mmol) in 20 mL of methanolic solution of HCl (3% HCl in MeOH) was stirred at room temperature for 1 h. Methanol was removed in vacuo, the residue dissolved in ethyl acetate, and washed with saturated aqueous sodium bicarbonate and saturated aqueous brine. The separated organic layer was dried over sodium sulfate and filtered, and the filtrate was concentrated in vacuo to afford the title compound (0.3 g, 61%) as an off-white solid, which was carried on to the next step without further purification. $^1$H NMR (300 MHz, DMSO-$d_6$): δ 8.7 (s, 1H), 7.47 (d, J=1.8 Hz, 1H), 7.35 (d, J=3.3 Hz, 1H), 6.81 (d, J=1.8 Hz, 1H), 6.41 (d, J=2.7 Hz, 1H), 4.82 (t, J=5.4 Hz, 1H), 4.43 (t, J=7.2 Hz, 2H), 3.89 (t, J=6.6 Hz, 2H), 3.60 (q, J=6.0 Hz, 2H), 2.38-2.22 (m, 1H), 1.76-1.68 (m, 2H), 1.02-0.92 (m, 2H), 0.84 (t, J=7.5 Hz, 3H), 0.65-0.58 (m, 2H). ESI-MS m/z=433 (M+H)+.

4-Chloro-6-(7-cyclopropyl-1-propyl-1H-indol-5-yl)-7,8-dihydropyrimido[5, 4-f][1,4]oxazepin-5(6H)-one (22I)

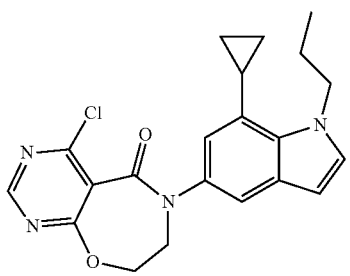 [SMILES: CCCn1ccc2cc(N3CCOc4ncnc(Cl)c4C3=O)cc(C3CC3)c21]

A solution of Example 22H (0.3 g, 0.692 mmol) and triethylamine (0.8 mL, 5.77 mmol) in acetonitrile (20 mL) was stirred at 80° C. for 16 h. The reaction mixture was cooled and concentrated in vacuo, and the residue was partitioned between ethyl acetate and water. Separated organic layer was dried over sodium sulfate and filtered, and the filtrate was concentrated in vacuo. The residue was purified by flash chromatography using 20% ethyl acetate in hexane to afford the title compound (0.22 g, 72%) as an off-white solid. $^1$H NMR (300 MHz, DMSO-$d_6$): δ 8.81 (s, 1H), 7.41 (m, 2H), 6.83 (s, 1H), 6.48 (d, J=3.0 Hz, 1H), 4.72 (t, J=4.5 Hz, 2H), 4.55 (t, J=7.5 Hz, 2H), 4.11 (t, J=4.8 Hz, 2H), 2.42-2.30 (m, 1H), 1.88-1.72 (m, 2H), 1.04-0.85 (m, 2H), 0.89 (t, J=7.2 Hz, 3H), 0.82 (m, 2H). ESI-MS m/z=397.1 (M+H)+.

4-Amino-6-(7-cyclopropyl-1-propyl-1H-indol-5-yl)-7,8-dihydropyrimido[5,4-f][1, 4]oxazepin-5(6H)-one (22)

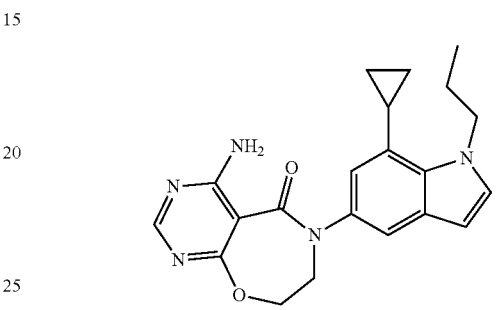

A solution of Example 22I (0.25 g, 0.630 mmol) in 0.5 M ammonia in 1, 4-dioxane (15 mL) was stirred at room temperature for 3 h. The reaction mixture was concentrated in vacuo, and the residue was partitioned between ethyl acetate and water. Separated organic layer was dried over sodium sulfate and filtered, and the filtrate was concentrated in vacuo to give a solid mass, which was triturated with diethyl ether to afford the title compound (0.19 g, 76%) as a white solid. $^1$H NMR (400 MHz, DMSO-$d_6$): δ 8.16 (s, 1H), 7.60 (bs, 2H), 7.38 (d, J=3.2 Hz, 1H), 7.33 (d, J=2.0 Hz, 1H), 6.79 (d, J=1.2 Hz, 1H), 6.44 (d, J=3.2 Hz, 1H), 4.61 (t, J=4.4 Hz, 2H), 4.53 (t, J=7.2 Hz, 2H), 3.95 (t, J=4.4 Hz, 2H), 2.40-2.32 (m, 1H), 1.80-1.76 (m, 2H), 0.99 (m, 2H), 0.88 (t, J=7.6 Hz, 3H), 0.84-0.80 (m, 2H). ESI-MS m/z=378.1 (M+H)+; LCMS purity: 94%.

Example 23

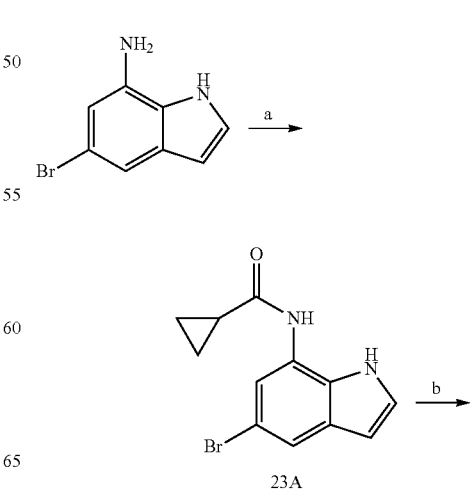

65
-continued

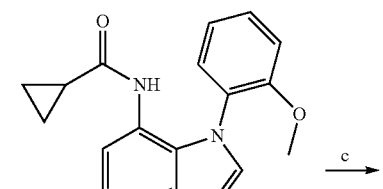
23B

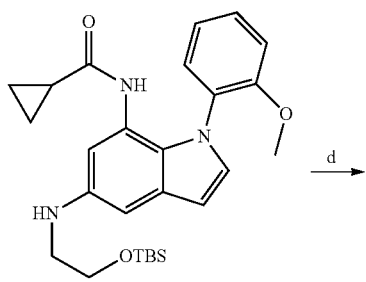
23C

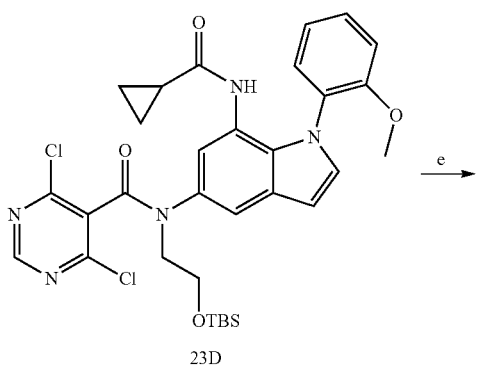
23D

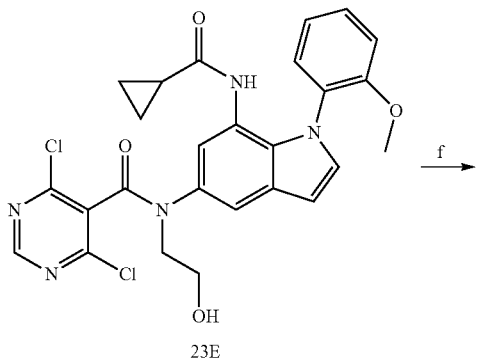
23E

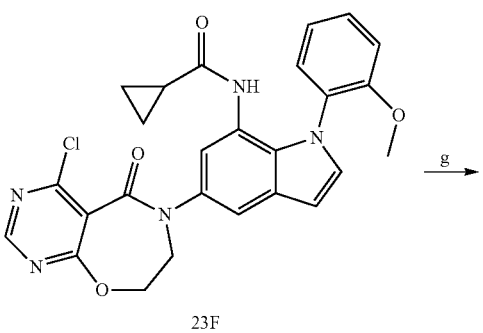
23F

66
-continued

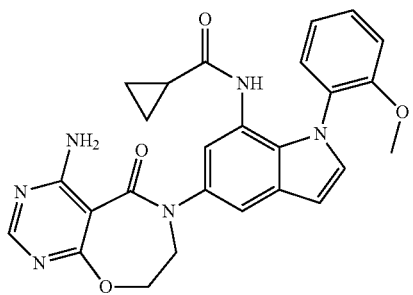
23

Reagents and conditions: a) Cyclopropane carbonyl chloride, DCM, Et₃N, RT, 2 h; b) 2-Iodoanisole, CuBr, Cu(OAc)₂, K₂CO₃, NaOH, DMF, 140° C., 6 h; c) NH₂(CH₂)₂OTBS, Pd(OAc)₂, X-Phos, Cs₂CO₃, toluene, 100° C., 7 h; d) 4,6-dichloropyrimidine-5-carbonyl chloride, Et₃N, DCM, RT, 2 h; e) TBAF, THF, RT, 2 h; f) Et₃N, CH₃CN, 70° C., 3 h; g) NH₃, dioxane, RT, 2 h.

Procedures

N-(5-(4-Amino-5-oxo-7,8-dihydropyrimido[5,4-f][1,4]oxazepin-6(5H)-yl)-1-(2-methoxyphenyl)-1H-indol-7-yl)cyclopropanecarboxamide N-(5-Bromo-1H-indol-7-yl)cyclopropanecarboxamide (23A)

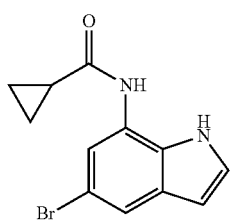 [SMILES: O=C(Nc1cc(Br)cc2cc[nH]c12)C1CC1]

A solution of cyclopropanecarbonyl chloride (0.54 g, 5.21 mmol) in DCM (10 mL) was added dropwise to an ice-cold solution of 5-bromo-1H-indol-7-amine (1.0 g, 4.74 mmol) and triethylamine (0.991 mL, 7.11 mmol) in DCM (20 mL), and the mixture was stirred for 2 h. The reaction mixture was concentrated in vacuo and partitioned between ethyl acetate and water. Separated organic layer was dried over sodium sulphate and filtered, and the filtrate was concentrated in vacuo. The residue was purified by flash chromatography using 20% ethyl acetate in hexanes to afford the title compound (1.1 g, 76%) as a red solid. $^1$H NMR (300 MHz, DMSO-d₆): δ 11.0 (s, 1H), 10.08 (s, 1H), 7.72 (s, 1H), 7.48 (s, 1H), 7.41 (t, J=3.0 Hz, 1H), 6.43 (t, J=2.4 Hz, 1H), 1.90-1.86 (m, 1H), 0.88-0.82 (m, 4H). ESI-MS m/z=279 (M+H)⁺.

N-(5-Bromo-1-(2-methoxyphenyl)-1H-indol-7-yl)cyclopropanecarboxamide (23B)

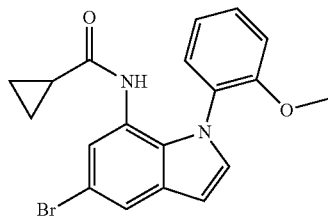 [SMILES: COc1ccccc1-n1ccc2cc(Br)cc(NC(=O)C3CC3)c21]

1-Iodo-2-methoxybenzene (1.06 g, 4.30 mmol) was added to a solution of Example 23A (1.0 g, 3.58 mmol) and copper(I) bromide (0.051 g, 0.358 mmol) in toluene (20 mL), followed by addition of potassium carbonate (0.99 g, 7.17 mmol), and the mixture was stirred at 100° C. for 10 min. NaOH (100 mg, 2.69 mmol) and copper(II) acetate (65.0 mg, 0.358 mmol) were then added at 100° C., and the reaction mixture was stirred for 6 h. Insoluble solids were filtered, the filtrate was concentrated, and the residue was partitioned between ethyl acetate and water. Separated organic layer was dried over sodium sulphate and filtered. The filtrate was concentrated in vacuo and purified by flash chromatography using 10% ethyl acetate in hexanes to afford the title compound (0.4 g, 29%) as a red solid. $^1$H NMR (400 MHz, DMSO-$d_6$): δ 9.14 (s, 1H), 7.69 (d, J=1.6 Hz, 1H), 7.41 (dt, $J_1$=1.6 Hz, $J_2$=8.8 Hz, 1H), 7.28 (d, J=3.2 Hz, 1H), 7.19 (d, J=6.4 Hz, 1H), 7.11 (d, J=8.0 Hz, 1H), 7.01-6.97 (m, 2H), 6.60 (d, J=2.8 Hz, 1H), 3.64 (s, 3H), 1.08 (m, 1H), 0.47-0.32 (m, 4H). ESI-MS m/z=385 (M+H)$^+$.

N-(5-(2-(tert-Butyldimethylsilyloxy)ethylamino)-1-(2-methoxyphenyl)-1H-indol-7-yl)cyclopropanecarboxamide (23C)

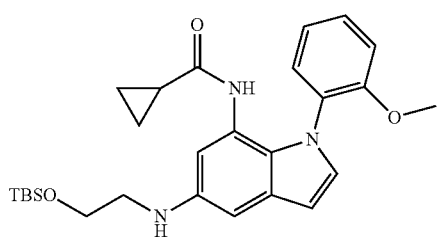 [SMILES: COc1ccccc1-n1ccc2cc(NCCO[Si](C)(C)C(C)(C)C)cc(NC(=O)C3CC3)c21]

A mixture of Example 23B (0.4 g, 1.038 mmol), 2-(tert-butyldimethylsilyloxy)ethanamine (0.21 g, 1.246 mmol), cesium carbonate (0.677 g, 2.077 mmol), palladium acetate (0.0233 g, 0.104 mmol) and X-Phos (0.0495 g, 0.104 mmol) in toluene (15 mL) under argon was stirred at 100° C. for 7 h. The reaction was warmed to room temperature, diluted into ethyl acetate and washed with water. Separated organic layer was dried over sodium sulfate and filtered, and the filtrate was concentrated under vacuum to obtain dark oil. The residue was purified by flash chromatography using 15% ethyl acetate in hexanes to afford the title compound (0.15 g, 22%) as a syrup. $^1$H NMR (300 MHz, DMSO-$d_6$): δ 8.85 (s, 1H), 7.33 (t, J=10 Hz, 1H), 7.13-6.92 (m, 4H), 6.60 (s, 1H), 6.37 (d, J=2.0 Hz, 1H), 6.35 (d, J=4.0 Hz, 1H), 4.97 (t, J=5.7 Hz, 1H), 3.75 (t, J=6.0 Hz, 2H), 3.65 (s, 3H), 3.16 (q, J=6.3 Hz, 2H), 1.09 (m, 1H), 0.88 (s, 9H), 0.39-0.35 (m, 4H), 0.06 (s, 6H). ESI-MS m/z=480 (M+H)$^+$.

N-(2-(tert-Butyldimethylsilyloxy)ethyl)-4,6-dichloro-N-(7-(cyclopropanecarboxamido)-1-(2-methoxyphenyl)-1H-indol-5-yl)pyrimidine-5-carboxamide (23D)

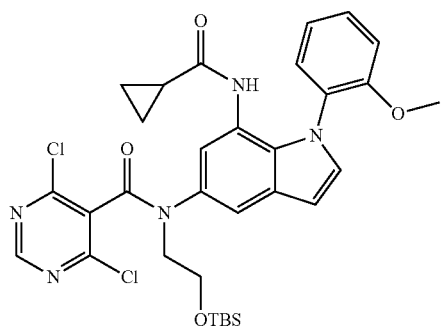 [SMILES: COc1ccccc1-n1ccc2cc(N(CCO[Si](C)(C)C(C)(C)C)C(=O)c3c(Cl)ncnc3Cl)cc(NC(=O)C3CC3)c21]

A solution of 4,6-dichloropyrimidine-5-carbonyl chloride (0.079 g, 0.375 mmol) in DCM (2 mL) was added dropwise to an ice-cold solution of Example 23C (0.15 g, 0.313 mmol) and triethylamine (0.29 mL, 2.06 mmol) in DCM (20 mL), and the mixture was stirred for 2 h. The reaction mixture was concentrated in vacuo, and the residue was partitioned between ethyl acetate and water. Separated organic layer was dried over sodium sulphate and filtered, and the filtrate was concentrated in vacuo. The residue was purified by flash chromatography using 20% ethyl acetate in hexane to afford the title compound (0.19 g, 85%) as a yellow solid. $^1$H NMR (400 MHz, DMSO-$d_6$): δ 9.00 (s, 1H), 8.77 (s, 1H), 7.58 (s, 1H), 7.38 (dt, $J_1$=1.2 Hz, $J_2$=8.8 Hz, 1H), 7.25 (d, J=3.2 Hz, 1H), 7.12 (d, J=7.2 Hz, 1H), 7.07 (d, J=8.0 Hz, 1H), 6.99-6.94 (m, 2H), 6.56 (d, J=2.8 Hz, 1H), 3.97 (m, 2H), 3.82 (t, J=5.6 Hz, 2H), 3.58 (s, 3H), 1.07 (m, 1H), 0.87 (s, 9H), 0.42-0.36 (m, 4H), 0.049 (s, 6H).

4,6-Dichloro-N-(7-(cyclopropanecarboxamido)-1-(2-methoxyphenyl)-1H-indol-5-yl)-N-(2-hydroxyethyl)pyrimidine-5-carboxamide (23E)

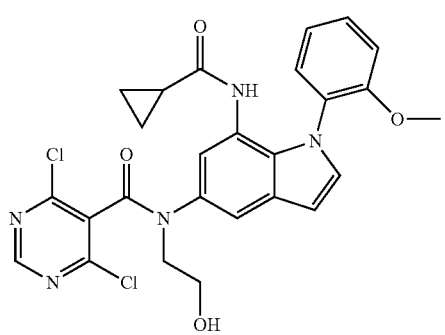 [SMILES: COc1ccccc1-n1ccc2cc(N(CCO)C(=O)c3c(Cl)ncnc3Cl)cc(NC(=O)C3CC3)c21]

TBAF (0.152 g, 0.58 mmol) in THF (10 mL) was added to a solution of Example 23D (0.3 g, 0.575 mmol) in THF (5 mL), and the mixture was stirred at room temperature for 2 h. THF was removed in vacuo and the residue was partitioned between ethyl acetate and water. The separated organic layer was dried over sodium sulfate and filtered, and the filtrate was concentrated in vacuo to afford the title compound (0.13 g, 78%) as a yellow syrup, which was carried on to the next step without further purification. $^1$H NMR (400 MHz, DMSO-d$_6$): δ 9.02 (s, 1H), 8.76 (s, 1H), 7.59 (s, 1H), 7.36 (dt, J$_1$=1.6 Hz, J$_2$=8.8 Hz, 1H), 7.26 (d, J=3.2 Hz, 1H), 7.13 (d, J=7.6 Hz, 1H), 7.07 (d, J=7.6 Hz, 1H), 7.00-6.94 (m, 2H), 6.59 (d, J=2.8 Hz, 1H), 4.87 (bs, 1H), 3.92 (t, J=6.8 Hz, 2H), 3.64 (t, J=4.8 Hz, 2H), 3.59 (s, 3H), 1.08 (m, 1H), 0.43-0.36 (m, 4H). ESI-MS m/z=540 (M+H)$^+$.

N-(5-(4-Chloro-5-oxo-7,8-dihydropyrimido[5,4-f][1,4]oxazepin-6(5H)-yl)-1-(2-methoxyphenyl)-1H-indol-7-yl)cyclopropanecarboxamide (23F)

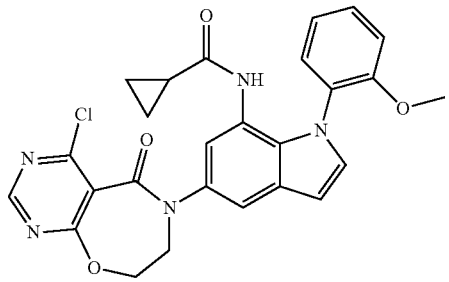 [SMILES: COc1ccccc1-n1ccc2cc(N3CCOc4ncnc(Cl)c4C3=O)cc(NC(=O)C3CC3)c21]

A slurry of Example 23E (0.13 g, 0.241 mmol) and triethylamine (0.067 mL, 0.481 mmol) in acetonitrile (20 mL) was stirred at 80° C. for 3 h. The reaction mixture was cooled and concentrated in vacuo, and the residue was partitioned between ethyl acetate and water. Separated organic layer was dried over sodium sulfate and filtered, and the filtrate was concentrated in vacuo to afford the title compound (0.09 g, 68.3%) as a thick syrup. $^1$H NMR (300 MHz, DMSO-d$_6$): δ 9.21 (s, 1H), 8.80 (s, 1H), 7.58 (d, J=1.8 Hz, 1H), 7.41 (dt, J$_1$=1.5 Hz, J$_2$=9.3 Hz, 1H), 7.31 (d, J=3.0 Hz, 1H), 7.19 (d, J=6.6 Hz, 1H), 7.13 (d, J=7.5 Hz, 1H), 7.00 (t, J=7.2 Hz, 1H), 6.93 (d, J=1.5 Hz, 1H), 6.67 (d, J=3.3 Hz, 1H), 4.78 (t, J=4.2 Hz, 2H), 4.16 (t, J=4.5 Hz, 2H), 3.68 (s, 3H), 1.14 (m, 1H), 0.46-0.32 (m, 4H). ESI-MS m/z=504 (M+H)$^+$.

N-(5-(4-Amino-5-oxo-7,8-dihydropyrimido[5,4-f][1,4]oxazepin-6(5H)-yl)-1-(2-methoxyphenyl)-1H-indol-7-yl)cyclopropanecarboxamide (23)

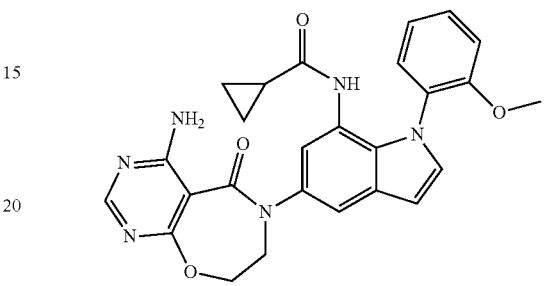

A solution of product of Example 23F (0.090 g, 0.179 mmol), in 0.5 M ammonia in 1,4-dioxane (2 mL) was stirred at room temperature for 2 h. The reaction mixture was concentrated in vacuo, and the residue was partitioned between ethyl acetate and water. Separated organic layer was dried over sodium sulfate and filtered, and the filtrate was concentrated in vacuo to give a solid mass, which was triturated with diethyl ether to afford the title compound (0.07 g, 65%) as a white solid. $^1$H NMR (400 MHz, DMSO-d$_6$): δ 9.18 (s, 1H), 8.18 (s, 1H), 7.63 (bs, 2H), 7.50 (s, 1H), 7.41 (t, J=7.2 Hz, 1H), 7.28 (d, J=2.8 Hz, 1H), 7.19 (d, J=7.6 Hz, 1H), 7.12 (d, J=8.0 Hz, 1H), 7.00 (t, J=7.2 Hz, 1H), 6.89 (d, J=1.2 Hz, 1H), 6.63 (d, J=3.2 Hz, 1H), 4.65 (t, J=4.4 Hz, 2H), 4.00 (t, J=3.6 Hz, 2H), 3.68 (s, 3H), 1.10 (m, 1H), 0.45-0.31 (m, 4H). ESI-MS m/z=485 (M+H)$^+$; HPLC purity: 95%.

Examples 24-25 were prepared using procedures analogous to those described in Examples 21-23 using appropriate starting materials.

| Exp | Structure | Analytical Data | Mass/Purity |
|---|---|---|---|
| 24 | 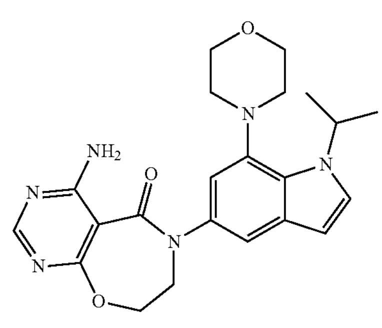 [SMILES: CC(C)n1ccc2cc(N3CCOc4ncnc(N)c4C3=O)cc(N3CCOCC3)c21] | $^1$H NMR (400 MHz, DMSO-d$_6$): δ 8.13 (s, 1H), 7.58 (bs, 2H), 7.52 (d, J = 3.6 Hz, 1H), 7.24 (d, J = 2.0 Hz, 1H), 6.87 (d, J = 1.6 Hz, 1H), 6.47 (d, J = 3.2 Hz, 1H), 5.72 (m, 1H), 4.59 (t, J = 4.4 Hz, 2H), 3.94 (t, J = 4.4 Hz, 2H), 3.86 (d, J = 10.8 Hz, 2H), 3.66 (dt, J$_1$ = 2.4 Hz, J$_2$ = 10.8 Hz, 2H), 2.96-2.82 (m, 4H), 1.38 (d, J = 6.4 Hz, 6H). | ESI-MS m/z = 423 (M + H)$^+$: HPLC purity 92%. |

| Exp | Structure | Analytical Data | Mass/Purity |
|---|---|---|---|
| 25 | 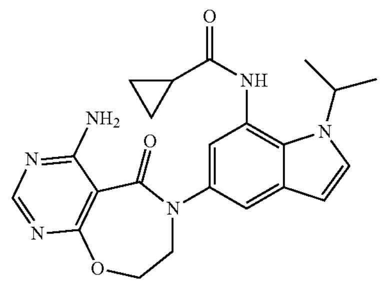 [SMILES: CC(C)n1ccc2cc(N3CCOc4ncnc(N)c4C3=O)cc(NC(=O)C3CC3)c21] | $^1$H NMR (300 MHz, DMSO-$d_6$): δ 10.05 (s, 1H), 8.17 (s, 1H), 7.62 (bs, 2H), 7.55 (d, J = 3.3 Hz, 1H), 7.43 (d, J = 1.2 Hz, 1H), 6.84 (s, 1H), 6.53 (d, J = 3.3 Hz, 1H), 5.03 (m, 1H), 4.63 (t, J = 4.5 Hz, 2H), 3.97 (m, 2H), 1.85 (m, 1H), 1.39 (d, J = 6.6 Hz, 6H), 0.90-0.72 (m, 4H). | ESI-MS m/z 421 (M + H)$^+$; HPLC purity 99.48%. |
Example 26
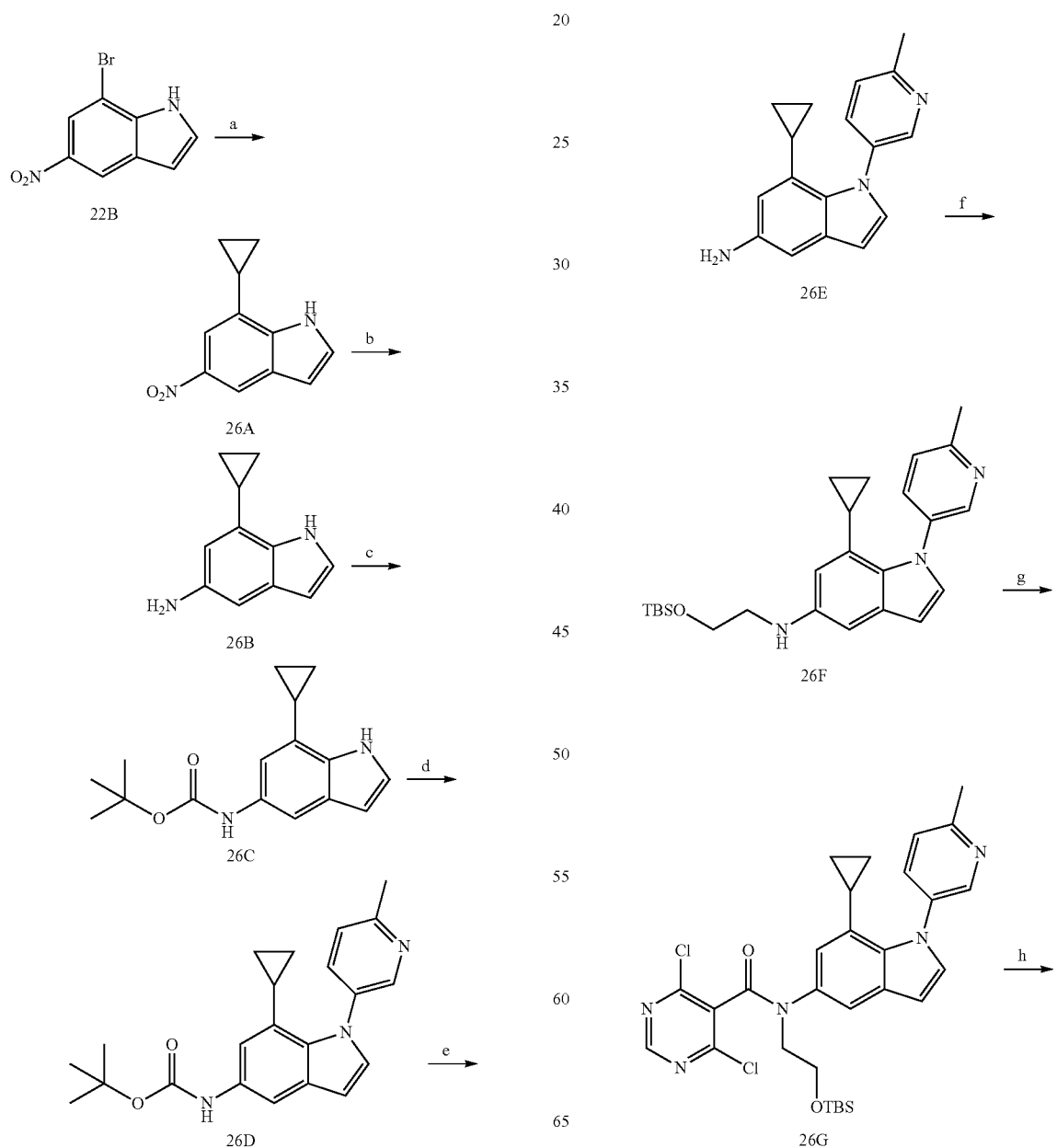

-continued

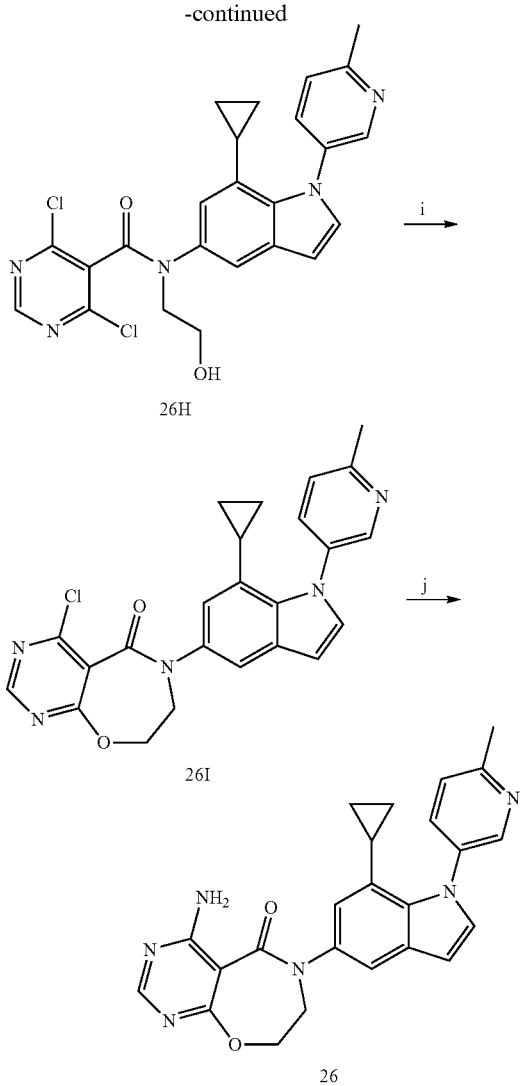

Reagents and conditions: a) Cyclopropyl boronic acid, Cs₂CO₃, PdCl₂(dppf), Toluene-H₂O 100° C., 2 h; b) Pd/C, EtOH, H₂, RT, 16 h; c) (Boc)₂O, Et₃N, THF, RT, 2 h; d) 5-Bromo-2-methylpyridine, K₃PO₄, (R,R)-N,N'-dimethyl-1,2-cyclohexanediamine, CuI, Dioxane, 110° C., 24 h; e) 2M HCl in Dioxane, RT, 2 h; f) TBDMSO(CH₂)₂Br, K₂CO₃, CH₃CN, 80° C., 24 h; g) 4,6-dichloropyrimidine-5-carbonyl chloride, Et₃N, DCM, RT, 1 h; h) 5% HCl—MeOH, RT, 1 h; i) Et₃N, CH₃CN, 80° C., 16 h; j) NH₃, Dioxane, RT, 3 h.

Procedures

4-Amino-6-(7-cyclopropyl-1-(6-methylpyridin-3-yl)-1H-indol-5-yl)-7,8-dihydropyrimido[5,4-f][1,4]oxazepin-5(6H)-one 7-Cyclopropyl-5-nitro-1H-indole (26A)

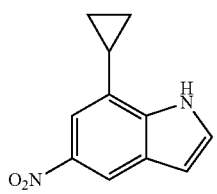

PdCl₂ (dppf)-CH₂Cl₂ adduct (7.59 g, 10.37 mmol) was added to a solution of 22B (25 g, 104 mmol) in 500 mL of toluene and water (1:1) kept under argon atmosphere. Cesium carbonate (40.6 g, 124 mmol) and cyclopropyl boronic acid (17.82 g, 207 mmol) were then added. The mixture was degassed for 5 min and stirred at 100° C. for 16 h. The reaction mixture was allowed to room temperature and partitioned between ethyl acetate and water. Separated organic layer was washed with water, dried over sodium sulphate, and filtered. The filtrate was concentrated in vacuo. The crude product was purified by flash chromatography using 20% ethyl acetate in hexane to afford title compound (17 g, 79%) as a yellow solid. ¹H NMR (300 MHz, DMSO-d₆): δ 11.98 (s, 1H), 8.40 (d, J=1.8 Hz, 1H), 7.62 (t, J=3.0 Hz, 1H), 7.49 (d, J=2.1 Hz, 1H), 6.75 (dd, J₁=1.8 Hz, J₂=3.0 Hz, 1H), 2.35 (m, 1H), 1.13-1.05 (m, 2H), 0.87-0.80 (m, 2H). ESI-MS m/z=201 (M–H)⁻.

7-Cyclopropyl-1H-indol-5-amine (26B)

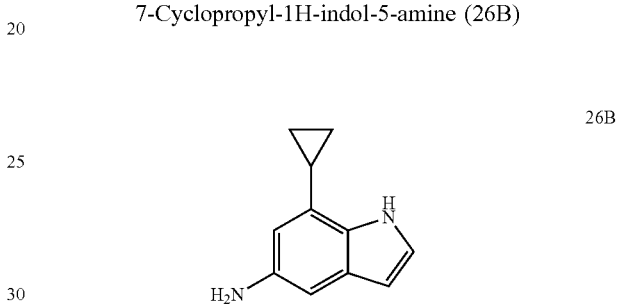

Palladium on carbon (3 g, 28.2 mmol) was added to a solution of 26A (15 g, 74.2 mmol) in ethanol (200 mL), and the mixture was stirred under hydrogen atmosphere for 16 h at room temperature. The reaction mixture was filtered through a pad of celite, and the filtrate was concentrated under reduced pressure. The crude product was purified by flash chromatography using 30% ethyl acetate in hexane to afford title compound (12 g, 93%) as a pale yellow viscous liquid. ¹H NMR (300 MHz, DMSO-d₆): δ 10.62 (s, 1H), 7.11 (t, J=2.7 Hz, 1H), 6.48 (d, J=2.1 Hz, 1H), 6.12 (dd, J₁=2.1 Hz, J₂=3.0 Hz, 1H), 6.04 (d, J=1.8 Hz, 1H), 4.30 (s, 2H), 2.14 (m, 1H), 0.96-0.90 (m, 2H), 0.65-0.60 (m, 2H). ESI-MS m/z=173 (M+H)⁺.

tert-Butyl 7-cyclopropyl-1H-indol-5-ylcarbamate (26C)

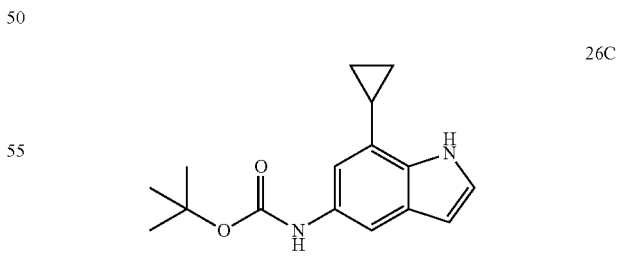

Triethylamine (14.57 g, 105 mmol) was added to a solution of 26B (12 g, 69.7 mmol) in methanol (150 mL) followed by di-tert-butyl dicarbonate (17.79 g, 77 mmol), and the mixture was stirred for 2 h at 0° C. MeOH was removed in vacuo, and the residue was partitioned between ethyl acetate and water. The separated organic layer was dried over sodium sulfate and filtered, and the filtrate was concentrated in vacuo to afford title compound (18 g, 95%) as an off white solid. ¹H NMR (300 MHz, DMSO-d₆): δ 10.99 (s, 1H), 8.86 (s, 1H), 7.44 (s, 1H), 7.26 (t, J=2.7 Hz, 1H), 6.71 (d, J=1.2 Hz, 1H), 6.32 (dd, J₁=1.8 Hz, J₂=3.0 Hz, 1H), 2.20 (m, 1H), 1.46 (s, 9H), 1.01-0.94 (m, 2H), 0.66-0.61 (m, 2H). ESI-MS m/z=273 (M+H)⁺.

tert-Butyl 7-cyclopropyl-1-(6-methylpyridin-3-yl)-1H-indol-5-ylcarbamate (26D)

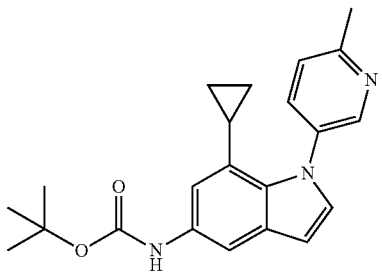

Copper (I) iodide (0.28 g, 1.46 mmol) and (R,R)—N,N'-dimethyl-1,2-cyclohexanediamine (0.208 g, 1.46 mmol) were added to a solution of 26C (2 g, 7.35 mmol) in 1,4-dioxane (20 mL) under argon atmosphere, followed by 5-bromo-2-methylpyridine (1.9 g, 11.02 mmol) and potassium phosphate (3.12 g, 14.7 mmol). The mixture was then degassed for 5 min and stirred at 110° C. for 16 h. Insoluble solids were filtered, the filtrate was concentrated, and the residue was partitioned between ethyl acetate and water. Separated organic layer was dried over sodium sulphate and filtered, and the filtrate was concentrated in vacuo. The crude product was purified by flash chromatography using 15% ethyl acetate in hexane to afford title compound (0.26 g, 9.7%) as an off white solid. ¹H NMR (300 MHz, DMSO-d₆): δ 9.04 (s, 1H), 8.55 (d, J=2.1 Hz, 1H), 7.80 (dd, J₁=2.4 Hz, J₂=8.1 Hz, 1H), 7.63 (bs, 1H), 7.37 (d, J=8.4 Hz, 1H), 7.31 (d, J=3.3 Hz, 1H), 6.95 (s, 1H), 6.57 (d, J=2.7 Hz, 1H), 2.55 (s, 3H), 1.47 (s, 9H), 1.46 (m, 1H), 0.45-0.30 (m, 4H). ESI-MS m/z=363 (M+H)⁺.

7-Cyclopropyl-1-(6-methylpyridin-3-yl)-1H-indol-5-amine (26E)

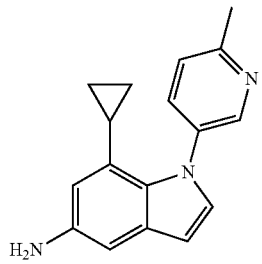

A solution of 26D (1.6 g, 4.4 mmol) and 4 N HCl in 1,4-dioxane solution (20 mL) was stirred at room temperature for 2 h. 1,4-Dioxane was then removed in vacuo, the residue dissolved in ethyl acetate and sequentially washed with saturated aqueous sodium bicarbonate and brine. The separated organic layer was dried over sodium sulfate and filtered, and the filtrate was concentrated in vacuo to afford title compound (1 g, 83%) as a colorless liquid, which was carried on to the next step without further purification. ¹H NMR (300 MHz, DMSO-d₆): δ 8.51 (d, J=2.1 Hz, 1H), 7.75 (dd, J₁=2.7 Hz, J₂=8.1 Hz, 1H), 7.34 (d, J=8.1 Hz, 1H), 7.15 (d, J=3.3 Hz, 1H), 6.60 (d, J=1.8 Hz, 1H), 6.37 (d, J=3.3 Hz, 1H), 6.28 (d, J=1.2 Hz, 1H), 4.54 (bs, 2H), 2.53 (s, 3H), 1.40 (m, 1H), 0.46-0.28 (m, 4H). ESI-MS m/z=264 (M+H)⁺.

N-(2-(tert-Butyldimethylsilyloxy)ethyl)-7-cyclopropyl-1-(6-methylpyridin-3-yl)-1H-indol-5-amine (26F)

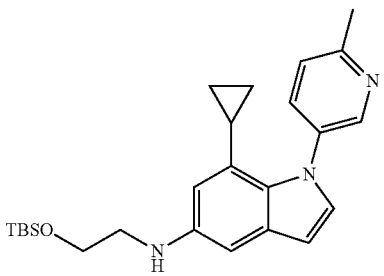

(2-Bromoethoxy) (tert-butyl) dimethylsilane (0.908 g, 3.8 mmol) and potassium carbonate (1.57 g, 11.39 mmol) were added to a solution of 26E (1 g, 3.8 mmol) in acetonitrile (20 mL), and the mixture was stirred at 80° C. for 16 h. Acetonitrile was removed in vacuo, and the residue was partitioned between ethyl acetate and water. Separated organic layer was dried over sodium sulphate and filtered, and the filtrate was concentrated in vacuo. The crude product was purified by flash column chromatography using 10% ethyl acetate in hexane to afford title compound (1.2 g, 73.3%) as an off white solid. ¹H NMR (300 MHz, DMSO-d₆): δ 8.52 (d, J=2.4 Hz, 1H), 7.77 (dd, J₁=2.7 Hz, J₂=7.8 Hz, 1H), 7.36 (d, J=8.1 Hz, 1H), 7.17 (d, J=3.3 Hz, 1H), 6.57 (d, J=2.1 Hz, 1H), 6.42 (d, J=3.3 Hz, 1H), 6.32 (s, 1H), 4.95 (t, J=6.3 Hz, 1H), 3.75 (t, J=6.0 Hz, 2H), 3.16 (q, J=6.3 Hz, 2H), 2.53 (s, 3H), 1.42 (m, 1H), 0.86 (s, 9H), 0.45-0.28 (m, 4H), 0.02 (s, 6H). ESI-MS m/z=422 (M+H)⁺.

N-(2-(tert-Butyldimethylsilyloxy)ethyl)-4,6-dichloro-N-(7-cyclopropyl-1-(6-methylpyridin-3-yl)-1H-indol-5-yl)pyrimidine-5-carboxamide (26G)

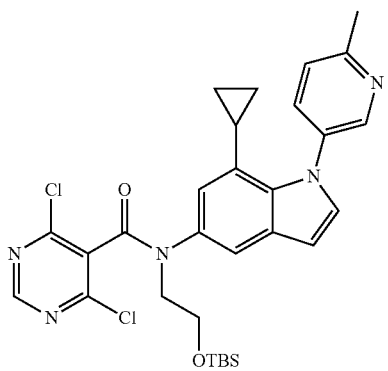

A solution of 4,6-dichloropyrimidine-5-carbonyl chloride (0.824 g, 4.27 mmol) in DCM (20 mL) was added drop-wise to an ice-cold solution of 26F (1.2 g, 2.85 mmol) and triethylamine (1.19 ml, 8.54 mmol) in DCM (25 mL), and the mixture was stirred for 1 h. The reaction was diluted with dichloromethane and washed with water. The separated organic layer was dried over sodium sulphate and filtered, and the filtrate was concentrated in vacuo. The residue was purified by flash chromatography using 20% ethyl acetate in hexane to afford title compound (1.3 g, 77%) as an off white solid. $^1$H NMR (300 MHz, DMSO-$d_6$): δ 8.74 (s, 1H), 8.51 (d, J=2.7 Hz, 1H), 7.79 (dd, $J_1$=2.7 Hz, $J_2$=8.7 Hz, 1H), 7.62 (d, J=1.8 Hz, 1H), 7.42 (d, J=3.3 Hz, 1H), 7.36 (d, J=8.1 Hz, 1H), 6.85 (d, J=1.2 Hz, 1H), 6.64 (d, J=3.3 Hz, 1H), 3.99 (t, J=5.4 Hz, 2H), 3.78 (t, J=5.7 Hz, 2H), 2.54 (s, 3H), 1.36 (m, 1H), 0.88 (s, 9H), 0.38-0.26 (m, 4H), 0.03 (s, 6H). ESI-MS m/z=597 (M+H)$^+$.

4, 6-Dichloro-N-(7-cyclopropyl-1-(6-methylpyridin-3-yl)-1H-indol-5-yl)-N-(2-hydroxyethyl)pyrimidine-5-carboxamide (26H)

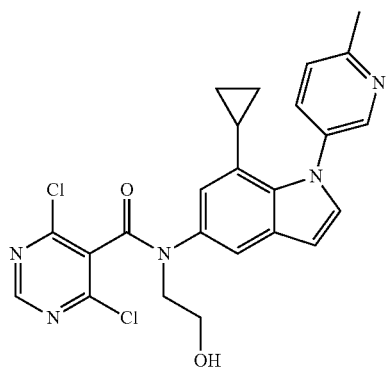

26H

A solution of 26G (1.3 g, 2.17 mmol) in 20 mL of methanolic solution of HCl (5% HCl in MeOH) was stirred at room temperature for 1 h. Methanol was removed in vacuo, and the residue was dissolved in ethyl acetate. The mixture was washed with saturated aqueous sodium bicarbonate and saturated aqueous brine. The separated organic layer was dried over sodium sulfate and filtered, and the filtrate was concentrated in vacuo to afford title compound (0.9 g, 86%) as an off-white solid, which was carried on to the next step without further purification. $^1$H NMR (300 MHz, DMSO-$d_6$): δ 8.74 (s, 1H), 8.53 (d, J=2.4 Hz, 1H), 7.81 (dd, $J_1$=2.7 Hz, $J_2$=8.1 Hz, 1H), 7.61 (d, J=2.4 Hz, 1H), 7.42 (d, J=3.3 Hz, 1H), 7.36 (d, J=8.1 Hz, 1H), 6.87 (d, J=1.8 Hz, 1H), 6.67 (d, J=3.3 Hz, 1H), 4.84 (t, J=5.3 Hz, 1H), 3.92 (t, J=6.0 Hz, 2H), 3.62 (q, J=5.7 Hz, 2H), 2.54 (s, 3H), 1.38 (m, 1H), 0.35-0.30 (m, 4H). ESI-MS m/z=484 (M+H)$^+$.

4-Chloro-6-(7-cyclopropyl-1-(6-methylpyridin-3-yl)-1H-indol-5-yl)-7,8-dihydropyrimido[5,4-f][1,4]oxazepin-5(6H)-one (26I)

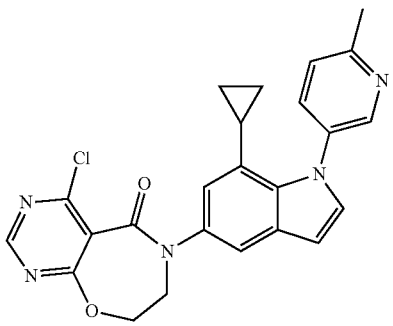

26I

A solution of 26H (0.9 g, 1.86 mmol) and triethylamine (0.78 mL, 5.6 mmol) in acetonitrile (20 mL) was stirred at 80° C. for 16 h. The reaction was cooled to room temperature, concentrated in vacuo and partitioned between ethyl acetate and water. The separated organic layer was dried over sodium sulfate and filtered, and the filtrate was concentrated in vacuo to afford title compound (0.7 g, 84%) as an off-white solid. $^1$H NMR (400 MHz, DMSO-$d_6$): δ 8.83 (s, 1H), 8.60 (d, J=2.4 Hz, 1H), 7.87 (dd, $J_1$=2.8 Hz, $J_2$=8.0 Hz, 1H), 7.56 (d, J=2.0 Hz, 1H), 7.47 (d, J=3.2 Hz, 1H), 7.41 (d, J=8.4 Hz, 1H), 6.88 (d, J=1.6 Hz, 1H), 6.73 (d, J=3.2 Hz, 1H), 4.74 (t, J=4.8 Hz, 2H), 4.14 (t, J=4.8 Hz, 2H), 2.57 (s, 3H), 1.51 (m, 1H), 0.54-0.50 (m, 2H), 0.38-0.30 (m, 2H). ESI-MS m/z=446 (M+H)$^+$.

4-Amino-6-(7-cyclopropyl-1-(6-methylpyridin-3-yl)-1H-indol-5-yl)-7,8-dihydropyrimido[5,4-f][1,4]oxazepin-5(6H)-one (26)

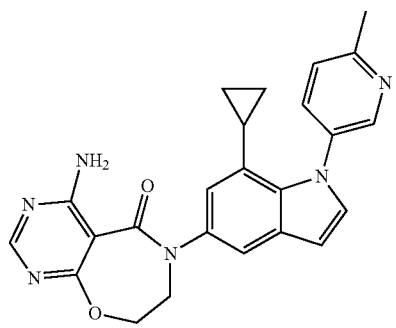

26

A solution of 26I (0.7 g, 1.57 mmol) in 0.5 M ammonia in 1, 4-dioxane (20 mL) was stirred at room temperature for 3 h. The reaction mixture was concentrated in vacuo, and the residue was partitioned between ethyl acetate and water. Separated organic layer was dried over sodium sulfate and filtered, and the filtrate was concentrated in vacuo to give a solid mass, which was triturated with diethyl ether to afford title compound (0.5 g, 68%) as a white solid. $^1$H NMR (300 MHz, DMSO-$d_6$): δ 8.60 (d, J=2.4 Hz, 1H), 8.17 (s, 1H), 7.86 (dd, $J_1$=4.0 Hz, $J_2$=8.4 Hz, 1H), 7.63 (bs, 2H), 7.47 (d, J=1.8 Hz, 1H), 7.44 (d, J=3.0 Hz, 1H), 7.41 (d, J=8.4 Hz, 1H), 6.84 (s, 1H), 6.70 (d, J=3.3 Hz, 1H), 4.64 (t, J=3.9 Hz, 2H), 3.97 (t, J=4.5 Hz, 2H), 2.57 (s, 3H), 1.49 (m, 1H), 0.56-0.50 (m, 2H), 0.38-0.30 (m, 2H). ESI-MS m/z=427 (M+H)⁺.

Examples 27-36 were prepared using procedures analogous to those described in Examples 1, 2, 13, 21 and 26 using appropriate starting materials.

| Exp | Structure | Analytical Data | Mass/Purity |
|---|---|---|---|
| 27 | 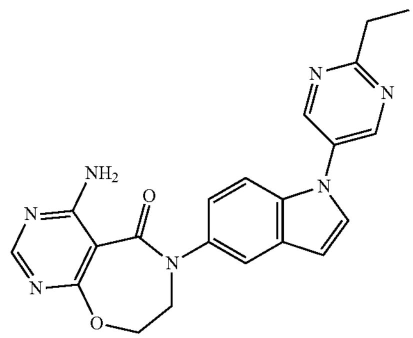 [SMILES: CCc1ncc(-n2ccc3cc(N4CCOc5ncnc(N)c5C4=O)ccc32)cn1] | $^1$H NMR (300 MHz, DMSO-d$_6$): δ 9.06 (s, 2H), 8.18 (s, 1H), 7.82 (d, J = 3.3 Hz, 1H), 7.7-7.6 (m, 4H), 7.2 (dd, J$_1$ = 2.4 Hz, J$_2$ = 9.0 Hz, 1H), 6.81 (d, J = 3.0 Hz, 1H),. 4.65 (t, J = 5.1 Hz, 2H), 4.01 (t, J = 5.1 Hz, 2H), 3.02 (q, J = 7.8 Hz, 2H), 1.36 (t, J = 7.8 Hz, 3H). | ESI-MS m/z = 402 (M + H)⁺. HPLC purity: 95% |
| 28 | 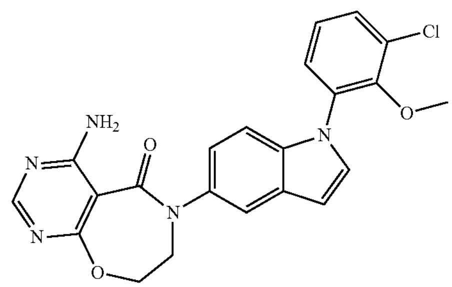 [SMILES: COc1c(Cl)cccc1-n1ccc2cc(N3CCOc4ncnc(N)c4C3=O)ccc21] | $^1$H NMR (400 MHz, DMSO-d$_6$): δ 8.18 (s, 1H), 7.59-7.65 (m, 5H), 7.5 (dd, J$_1$ = 8.0 Hz, J$_2$ = 1.6 Hz, 1H), 7.37 (t, J = 8.4 Hz, 1H), 7.22 (d, J = 8.8 Hz, 1H), 7.15 (dd, J$_1$ = 8.8 Hz, J$_2$ = 2.0 Hz, 1H), 6.76 (d, J = 2.8 Hz, 1H), 4.65 (t, J = 4.8 Hz, 2H), 4.02 (t, J = 4.4 Hz, 2H), 3.31 (s, 3H). | ESI-MS m/z = 436 (M + H)⁺; LCMS purity 98%. |
| 29 | 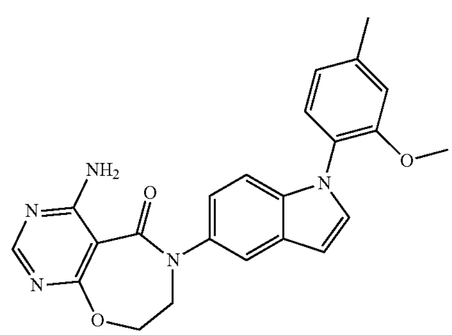 [SMILES: COc1cc(C)ccc1-n1ccc2cc(N3CCOc4ncnc(N)c4C3=O)ccc21] | $^1$H NMR (300 MHz, DMSO-d$_6$): δ 8.18 (s, 1H), 7.63 (bs, 2H), 7.57 (s, 1H), 7.44 (d, J = 3.3 Hz, 1H), 7.25 (d, J = 7.5 Hz, 1H), 7.12 (s, 1H), 7.06 (s, 2H), 6.93 (d, J = 6.9 Hz, 1H), 6.63 (d, J = 3.3 Hz, 1H), 4.64 (t, J = 3.9 Hz, 2H), 4.00 (t, J = 3.9 Hz, 2H), 3.74 (s, 3H), 2.42 (s, 3H). | ESI-MS m/z = 416 (M + H)⁺; LCMS purity 96%. |
| 30 | 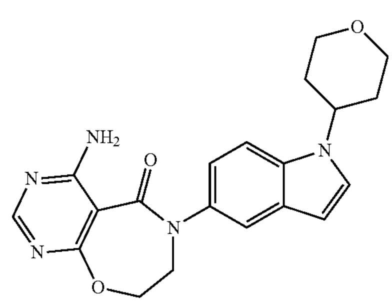 [SMILES: Nc1ncnc2c1C(=O)N(c1ccc3c(ccn3C3CCOCC3)c1)CCO2] | $^1$H NMR (400 MHz, DMSO-d$_6$): δ 8.17 (s, 1H), 7.65-7.58 (m, 4H), 7.51 (d, J = 2.0 Hz, 1H), 7.10 (dd, J$_1$ = 2.0 Hz, J$_2$ = 8.8 Hz, 1H), 6.48 (d, J = 2.8 Hz, 1H), 4.68-4.60 (m, 3H), 4.05-3.96 (m, 4H), 3.63-3.54 (m, 2H), 2.08-1.86 (m, 4H). | ESI-MS m/z: 380 (M + H)⁺; HPLC purity: 95%. |

| Exp | Structure | Analytical Data | Mass/Purity |
|---|---|---|---|
| 31 | 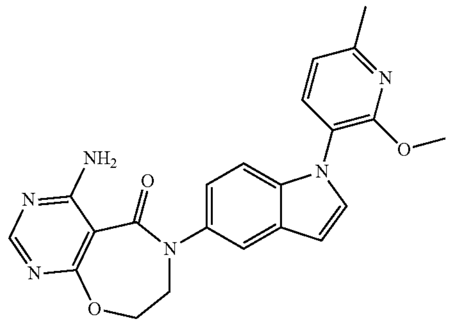 [SMILES: COc1nc(C)ccc1-n1ccc2cc(N3CCOc4ncnc(N)c4C3=O)ccc21] | ¹H NMR (400 MHz, DMSO-d₆): δ 8.17 (s, 1H), 7.74 (d, J = 7.6 Hz, 1H), 7.62 (bs, 2H), 7.59 (s, 1H), 7.50 (d, J = 3.2 Hz, 1H), 7.10 (s, 2H), 7.05 (d, J = 8.0 Hz, 1H), 6.67 (d, J = 2.8 Hz, 1H), 4.64 (t, J = 4.0 Hz, 2H), 4.0 (t, J = 4.4 Hz, 2H), 3.85 (s, 3H), 2.49 (s, 3H). | ESI-MS m/z: 417 (M + H)⁺; LCMS purity: 96%. |
| 32 | 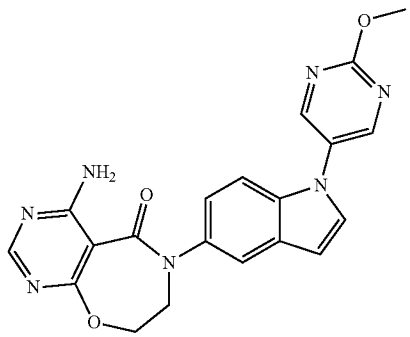 [SMILES: COc1ncc(-n2ccc3cc(N4CCOc5ncnc(N)c5C4=O)ccc32)cn1] | ¹H NMR (300 MHz, DMSO-d₆): δ 8.91 (s, 2H), 8.18 (s, 1H), 7.72 (d, J = 3.3 Hz, 1H), 7.68-7.58 (m, 3H), 7.51 (d, J = 9.0 Hz, 1H), 7.20 (dd, J₁ = 1.8 Hz, J₂ = 8.4 Hz, 1H), 6.78 (d, J = 3.0 Hz, 1H), 4.65 (t, J = 3.9 Hz, 2H), 4.06-3.98 (m, 5H). | ESI-MS m/z = 404 (M + H)⁺. HPLC purity: 95% |
| 33 | 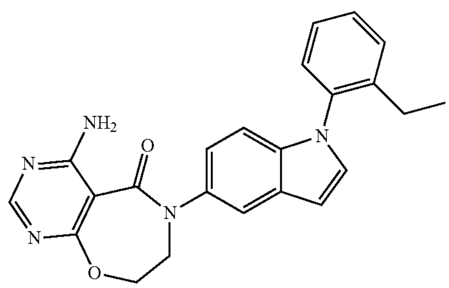 [SMILES: CCc1ccccc1-n1ccc2cc(N3CCOc4ncnc(N)c4C3=O)ccc21] | ¹H NMR (400 MHz, DMSO-d₆): δ 8.18 (s, 1H), 7.64-7.58 (m, 3H), 7.54-7.48 (m, 3H), 7.41 (dt, J₁ = 2.0 Hz, J₂ = 7.2 Hz, 1H), 7.31 (d, J = 7.2 Hz, 1H), 7.10 (dd, J₁ = 2.0 Hz, J₂ = 8.8 Hz, 1H), 6.96 (d, J = 8.8 Hz, 1H), 6.70 (d, J = 2.8 Hz, 1H), 4.64 (t, J = 4.4 Hz, 2H), 4.01 (t, J = 4.4 Hz, 2H), 2.30-2.39 (m, 2H), 0.95 (t, J = 7.2 Hz, 3H). | ESI-MS m/z = 400 (M + H)⁺; HPLC purity: 99% |
| 34 | 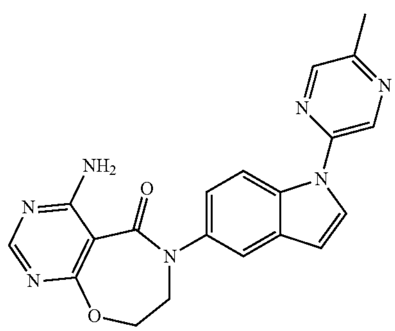 [SMILES: Cc1cnc(-n2ccc3cc(N4CCOc5ncnc(N)c5C4=O)ccc32)cn1] | ¹H NMR (400 MHz, DMSO-d₆): δ 9.05 (d, J = 1.2 Hz, 1H), 8.52 (s, 1H), 8.37 (d, J = 8.8 Hz, 1H), 8.18 (d, J = 2.4 Hz, 2H), 7.66 (d, J = 2.0 Hz, 1H), 7.63 (bs, 2H), 7.26 (dd, J₁ = 2.0 Hz, J₂ = 8.8 Hz, 1H), 6.84 (d, J = 3.6 Hz, 1H), 4.65 (t, J = 4.4 Hz, 2H), 4.03 (t, J = 4.4 Hz, 2H), 2.56 (s, 3H). | ESI-MS m/z = 388 (M + H)+. HPLC purity: 94% |
| 35 | 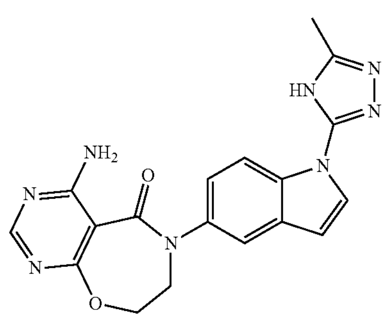 [SMILES: Cc1nnc(-n2ccc3cc(N4CCOc5ncnc(N)c5C4=O)ccc32)[nH]1] | ¹H NMR (300 MHz, DMSO-d₆): δ 8.33 (d, J = 8.7 Hz, 1H), 8.18 (s, 1H), 7.95 (d, J = 3.3 Hz, 1H), 7.72-7.60 (m, 4H), 7.27 (dd, J₁ = 1.8 Hz, J₂ = 8.7 Hz, 1H), 6.73 (d, J = 3.6 Hz, 1H), 4.65 (t, J = 5.4 Hz, 2H), 4.02 (t, J = 4.5 Hz, 2H), 2.45 (s, 3H). | ESI-MS m/z = 377 (M + H)+. LCMS purity: 87%. |

-continued

| Exp | Structure | Analytical Data | Mass/Purity |
|---|---|---|---|
| 36 | 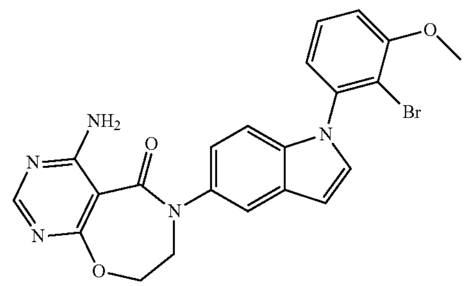 [SMILES: COc1cccc(-n2ccc3cc(N4CCOc5ncnc(N)c5C4=O)ccc32)c1Br] | $^1$H NMR (300 MHz, DMSO-$d_6$): δ 8.18 (s, 1H), 7.65-7.60 (m, 3H), 7.55 (d, J = 8.1 Hz, 1H), 7.51 (d, J = 3.3 Hz, 1H), 7.3 (d, J = 7.5 Hz, 1H), 7.13-7.09 (m, 2H), 7.0 (d, J = 8.7 Hz, 1H), 6.7 (d, J = 3.3 Hz, 1H), 4.64 (t, J = 4.2 Hz, 2H), 4.01 (t, J = 4.5 Hz, 2H), 3.96 (s, 3H). | ESI-MS m/z = 480 (M + H)+. LCMS purity: 95%. |

Biological Assay
Inhibition of Human DGAT1 Activity In Vitro

Human DGAT1 was expressed in Sf9 insect cells using a baculovirus expression system. Microsomes were prepared and used as enzyme for in vitro inhibition testing in either of two formats measuring production of coenzyme A or tridecanoylglycerol product, respectively. All steps were performed at 21-23° C. All data for DGAT1 inhibition by test compounds were collected under conditions where product formation was linear with reaction time.

CPM Assay:

For inhibition of CoA product formation, test compounds were prepared in 100% DMSO, diluted 100-fold into assay buffer, and 10 uL added to 96-well half-area plates (Greiner 675076). An equal volume (10 uL) of 3× enzyme in buffer was added and the components incubated for 30 minutes pre-reaction incubation to allow enzyme and test compounds to attain binding equilibrium. The 3× enzyme mixture contained 30 uM {4-[4-(4-amino-7,7-dimethyl-7H-pyrimido[4,5-b][1,4]oxazin-6-yl)phenyl]cyclohexyl}acetic acid for fully inhibited control wells. Some assays were performed with inclusion of didecanoylglycerol in the pre-reaction incubation of test compound and enzyme. DGAT reactions (30 uL) were initiated upon addition of 10 uL of 3× substrate solution. Final reaction conditions consisted of 20 mM HEPES pH 7.5, 2 mM MgCl$_2$, 1 mM CHAPS, 50 uM didecanoylglycerol, 3 uM decanoyl-CoA, 1 ug/mL microsomal protein, and 1% DMSO. Following a 60 minute reaction incubation, reactions were stopped and CoA product derivatized with 30 uL of buffer containing 10 uM {4-[4-(4-amino-7,7-dimethyl-7H-pyrimido[4,5-b][1,4]oxazin-6-yl)phenyl]cyclohexyl}acetic acid and 50 uM 7-diethylamino-3-(4'-maleimidylphenyl)-4-methylcoumarin (CPM). Fluorescence was read using Envision reader at Ex 405 nm/Em 480 nm about 30 minutes after addition of final solution. Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. IC$_{50}$s were fitted using GraphPad Prism to a sigmoidal dose response.

LE Assay:

For inhibition of triacylglycerol product formation, 11 uL reactions were run in white Polyplate-384 (PerkinElmer6007300) starting with a 30 minute pre-reaction incubation of 5 uL of 2.2× enzyme and 1 uL of 100% DMSO containing test compound or control compound, {4-[4-(4-amino-7,7-dimethyl-7H-pyrimido[4,5-b][1,4]oxazin-6-yl) phenyl]cyclohexyl}acetic acid. Some assays were performed with inclusion of didecanoylglycerol in the pre-reaction incubation of test compounds and enzyme. Reactions were initiated after 30 minute pre-reaction incubation via addition of 5 uL of 2.2× substrate. Final reaction conditions consisted of 50 mM HEPES pH 7.5, 2 mM MgCl$_2$, 1 mM CHAPS, 25 uM didecanoylglycerol, 0.5 uM decanoyl-CoA, 0.3 nCi/uL [$^{14}$C]-decanoyl-CoA or 0.5 nCi/uL [$^3$H]-decanoyl-CoA, 0.05-4 ug/mL microsomal protein, and 1% DMSO. Following 60 minute reaction incubation, reactions were stopped with 40 uL of 45% isopropanol and 50 mM sodium carbonate in water and mixed. Extraction of tridecanoylglycerol product was accomplished via addition of 30 uL Microscint-E (Perkin Elmer) and 2 hours of incubation (sealed). Plates were read on a Microbeta Microplate reader. Inhibition was normalized to controls containing DMSO or 10 uM {4-[4-(4-amino-7,7-dimethyl-7H-pyrimido[4,5-b][1,4]oxazin-6-yl)phenyl] cyclohexyl}acetic acid. IC$_{50}$s were fitted using GraphPad Prism to a sigmoidal dose response.

Biological Data

Exemplified compounds of the present invention were tested in one or more DGAT assays described above and were found to be inhibitors of DGAT1 with IC$_{50}$<10 μM. Data for specific examples tested in the human DGAT1 lipid extraction (LE) assays are listed below in Table 1.

TABLE 1

| Example # | hDGAT LE IC$_{50}$ (nM) |
|---|---|
| 1 | 39.1 |
| 2 | 0.5 |
| 3 | 14.7 |
| 4 | 31.3 |
| 5 | 6.8 |
| 6 | 25 |
| 7 | 3.2 |
| 8 | 2.9 |
| 9 | 9.7 |
| 10 | 7.9 |
| 11 | 13.3 |
| 12 | 1.8 |
| 13 | 101.1 |
| 14 | 14.5 |
| 15 | 6.8 |
| 16 | 4.8 |
| 17 | 0.3 |
| 18 | 24.1 |
| 19 | 11.2 |
| 20 | 4.2 |
| 21 | 16.3 |
| 22 | 1.8 |
| 23 | 16.1 |
| 24 | 82.2 |
| 25 | 93 |
| 26 | 3.4 |

TABLE 1-continued
| Example # | hDGAT LE IC$_{50}$ (nM) |
|---|---|
| 27 | 49.7 |
| 28 | 1.7 |
| 29 | 8.5 |
| 30 | 6.1 |
| 31 | 14.6 |
| 32 | 38.1 |
| 33 | 2.5 |
| 34 | 15.8 |
| 35 | 75 |
| 36 | 1.8 |
The invention claimed is:
1. A compound which is:
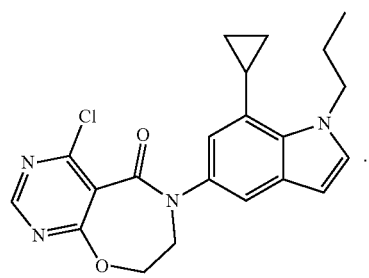 [SMILES: CCCn1ccc2cc(N3CCOc4ncnc(Cl)c4C3=O)cc(C3CC3)c21]
2. A compound which is:
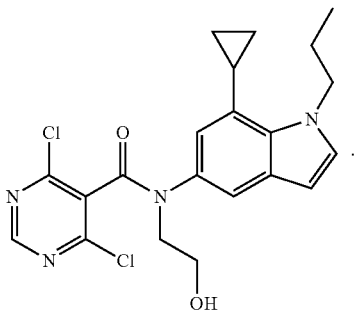 [SMILES: CCCn1ccc2cc(N(CCO)C(=O)c3c(Cl)ncnc3Cl)cc(C3CC3)c21]
3. A compound which is:
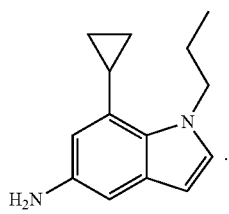
* * * * *